US007622658B2

(12) United States Patent
Cahoon et al.

(10) Patent No.: US 7,622,658 B2
(45) Date of Patent: Nov. 24, 2009

(54) COMPOSITIONS AND METHODS FOR ALTERING TOCOTRIENOL CONTENT

(75) Inventors: Edgar B. Cahoon, Webster Groves, MO (US); Sean J. Coughlan, Hockessin, DE (US); Rebecca E. Cahoon, Webster Groves, MO (US); Karlene H. Butler, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 155 days.

(21) Appl. No.: 11/558,961

(22) Filed: Nov. 13, 2006

(65) Prior Publication Data

US 2008/0005812 A1 Jan. 3, 2008

Related U.S. Application Data

(63) Continuation of application No. 10/373,406, filed on Feb. 24, 2003, now Pat. No. 7,154,029.

(60) Provisional application No. 60/366,757, filed on Mar. 22, 2002.

(51) Int. Cl.
*C12N 15/29* (2006.01)
*C12N 15/54* (2006.01)
*C12N 15/63* (2006.01)
*C12N 15/82* (2006.01)
*A01H 5/00* (2006.01)
*A01H 5/10* (2006.01)

(52) U.S. Cl. .................. 800/320; 800/287; 800/298; 800/306; 800/312; 800/317.2; 800/322; 536/23.1; 536/23.2; 536/23.6; 435/320.1; 435/419

(58) Field of Classification Search .................. None
See application file for complete search history.

(56) References Cited

FOREIGN PATENT DOCUMENTS

WO 02/13624 A1 2/2002

OTHER PUBLICATIONS

Cahoon et al. Nature Biotechnology; Sep. 2003, vol. 21, No. 9 pp. 1082-1087.*
Cahoon et al., Metabolic redesign of vitamin E biosynthesis in plants for tocotrienol production and increased antioxidant content, Nature Biotechnology (2003) 21(9):1082-1087.

* cited by examiner

*Primary Examiner*—Russell Kallis
(74) *Attorney, Agent, or Firm*—Pioneer Hi-Bred International, Inc.; Kathryn K. Lappegard

(57) ABSTRACT

The invention provides isolated nucleic acids and their encoded polypeptides that alter tocotrienol content in seeds. The invention further provides expression cassettes, host cells and transformed plants containing the nucleic acids. The present invention further provides methods for altering tocotrienol content in seeds.

20 Claims, No Drawings

COMPOSITIONS AND METHODS FOR ALTERING TOCOTRIENOL CONTENT

CROSS-REFERENCE TO RELATED APPLICATIONS

This application is a continuation of U.S. application Ser. No. 10/373,406 filed Feb. 24, 2003 now U.S. Pat. No. 7,154,029 which claims the benefit of U.S. Application Ser. No. 60/366,757 filed Mar. 22, 2002, which is herein incorporated by reference in its entirety.

FIELD OF THE INVENTION

The present invention relates to the field of plant molecular biology, particularly to the isolation of genes. The invention further relates to the use of the genes to host cells. More specifically, this invention pertains to nucleic acid fragments encoding homogentisate geranylgeranyl transferase in plants.

BACKGROUND OF THE INVENTION

Tocotrienols are vitamin E-related compounds whose occurrence in plants is limited primarily to the seeds and fruits of most monocot species (e.g., palm, wheat, rice and barley). Tocotrienols are structurally similar to tocopherols, including α-tocopherol or vitamin E, which occur ubiquitously in the plant kingdom as well as in photosynthetic microbes such as *Synechocystis*. Tocotrienols and tocopherols both contain a chromanol head group that is linked to a hydrocarbon side chain. The only structural difference between these molecules is the presence of three double bonds in the hydrocarbon side chain of tocotrienols. This difference is related to the biosynthetic origins of the side chains. Tocopherol side chains are derived from phytyl-pyrophosphate (PP), and the tocotrienol side chains are believed to be derived from geranylgeranyl-PP (Soll, J. et al. (1980) *Arch. Biochem. Biophys.* 204:544-550).

Four forms or molecular species of tocopherols and tocotrienols occur in nature: α, β, γ and δ. These molecular species contain different numbers of methyl groups that are bound to the aromatic portion of the chromanol head. Like tocopherols, tocotrienols are potent lipid-soluble antioxidants and therefore have considerable nutritive value in human and animal diets (Packer, L. et al. (2001) *J. Nutr.* 131:369S-373S). In addition, tocotrienols are believed to have therapeutic properties including a demonstrated ability to down regulate cholesterol biosynthesis (Theriault, A. et al. (1999) *Clin. Biochem.* 32:309-319; Qureshii, A. A. et al. (1986) *J. Biol. Chem.* 261:10544-10550).

It has been speculated that the first committed step in the biosynthesis of tocotrienols involves the condensation of geranylgeranyl-PP and homogentisate to form 2-methyl-6-geranylgeranylbenzoquinol (Soll, J. et al. (1980) *Arch. Biochem. Biophys.* 204:544-550). The enzyme that catalyzes this reaction can thus be functionally described as a homogentisate geranylgeranyl transferase (HGGT).

Functional identification of genes or cDNAs encoding HGGT polypeptides has yet to be reported. The lack of these nucleic acids limits efforts to manipulate the biosynthesis of the nutritionally important tocotrienols in plants and microbial hosts. The problem to be solved, therefore, is in identifying the nucleic acids that encode polypeptides required for tocotrienol biosynthesis in plants.

SUMMARY OF THE INVENTION

Compositions and methods for the alteration of the tocol content and composition of plants are provided. The compositions comprise novel nucleotide molecules comprising nucleotide sequences for HGGT. The compositions can be used to transform plants to manipulate the synthetic pathway for tocol compounds.

Transformed plants, plant cells, plant tissues, seed and grain are provided. Transformed plants of the invention find use in methods for improving grain or seed characteristics including, but not limited to, antioxidant level or activity.

Expression cassettes comprising sequences of the invention are provided. Isolated polypeptides encoded by the nucleotide sequences of the invention are also provided.

DETAILED DESCRIPTION

The problem to be solved is identifying the nucleic acids that encode polypeptides required for tocotrienol biosynthesis in plants. These polynucleotides may be used in plant cells and photosynthetic microbes to alter the tocols, such as tocotrienols, produced in the cells. More specifically, the polynucleotides of the instant invention may be used to significantly increase the content of vitamin E-related antioxidants such as tocotrienol in edible tissues of vegetable, fruit, and agronomic crop plants, including grains such as corn and soybean seed. The availability of nucleic acid sequences encoding all or a portion of the enzyme homogentisate geranylgeranyl transferase (HGGT) would facilitate studies to better understand tocotrienol biosynthesis in plants and provide genetic tools to alter tocotrienol metabolism. The present invention has solved this problem by providing nucleotide and deduced amino acid sequences corresponding to novel HGGT polynucleotides and corresponding polypeptides from barley (*Hordeum vulgare*), corn (*Zea mays*), rice (*Oryza sativa*) and wheat (*Triticum aestivum*).

The HGGT-catalyzed reaction is analogous to the first step in tocopherol biosynthesis, which involves the condensation of homogentisate and phytyl-PP to form 2-methyl-6-phytyl-benzoquinol (Soll, J. et al., supra). The latter reaction is catalyzed by the enzyme homogentisate phytyltransferase (HPT). cDNAs encoding HPT from a number of plant species have previously been disclosed in World Patent Application WO 00/68393. Given the similarity in their substrates and activity, one can hypothesize that HGGT is a divergent, but related form of HPT. It is likely that HGGT is the only specialized enzyme in the tocotrienol biosynthetic pathway. Methylation and cyclization reactions that convert the HGGT product 2-methyl-6-geranylgeranylbenzoquinol into tocotrienols are likely catalyzed by enzymes that are shared between the tocopherol and tocotrienol biosynthetic pathways (Schultz, G. et al. (1985) *Physiol. Plant.* 64:123-129). As such, expression of HGGT will be sufficient to confer tocotrienol biosynthesis to a plant, plant tissue, a cell from plant tissue or a photosynthetic microbe that does not normally produce tocotrienols.

Recently, genes or cDNAs for HPT have been identified and characterized from the cyanobacterium *Synechocystis* sp. PCC 6803 and *Arabidopsis thaliana* based on their sequence similarity to chlorophyll synthases (Schledz, M. et al. (2001) FEBS499:15-20; Collakova, E. and DellaPenna, D. (2001) *Plant Physiol.* 127:1113-1124). cDNAs for homologs of the *Arabidopsis* HPT have also been identified from wheat, rice, corn and soybean (Collakova, E. and DellaPenna, D. (2001) *Plant Physiol.* 127:1113-1124).

The invention is drawn to compositions and methods for altering tocols. The compositions and methods find use in improving the antioxidant quality of grain for use as food for humans and feed for livestock. Furthermore, the tocols can be extracted, purified or further altered via processing. As used herein, "grain" means the mature seed produced by commercial growers for purposes other than reproducing the species and/or immature seed as an integral part of whole plant corn harvested for silage. As used herein, grain includes plant parts commonly categorized as a fruit, nut or vegetable.

As used herein, "wild-type" refers to untransformed organisms and descendants of untransformed organisms.

The term "tocol" refers generally to any of the tocopherol and tocotrienol molecular species (e.g., α-, β-, γ-, and δ-) that are known to occur in biological systems. The term "tocol content" refers to the total amount of tocopherol and tocotrienol in a whole plant, tissue, or cell or in a microbial host. The term "tocol composition" refers both to the ratio of the various tocols produced in any given biological system and to altered characteristics, such as antioxidant activity, of any one tocol compound. When the alteration of tocols is taught or claimed herein, such alteration can be to tocol content and/or tocol composition. When an increase of tocols is taught or claimed herein, such increase refers to an increase of tocol content and/or an increase of tocol activity.

The term "tocotrienol" refers generally to any of the tocotrienol molecular species (e.g., α-, β-, γ-, and δ-) that are known to occur in biological systems. The term "tocotrienol content" refers to the total amount of tocotrienol in a whole plant, tissue, or cell or in a microbial host. The term "tocotrienol composition" refers both to the ratio of the various tocotrienols produced in any given biological system and to altered characteristics, such as antioxidant activity, of any one tocotrienol compound. When the alteration of a tocotrienol is taught or claimed herein, such alteration can be to tocotrienol content and/or tocotrienol composition. When an increase of tocotrienols is taught or claimed herein, such increase refers to an increase of tocotrienol content and/or an increase of tocotrienol activity.

The term "homogentisate phytyltransferase" or "HPT" refers to the enzyme that catalyzes the condensation of homogentisate (or homogentisic acid) and phytyl pyrophosphate (or phytyl diphosphate). This reaction is believed to be the committed step in tocopherol biosynthesis. Other names that have been used to refer to this enzyme include "homogentisate phytyl pyrophosphate prenyltransferase" and "homogentisate phytyl diphosphate prenyltransferase". The shortened version phytyl/prenyl transferase is also used.

The term "homogentisate geranylgeranyl transferase" or "HGGT" refers to the enzyme that catalyzes the condensation of homogentisate (or homogentisic acid) and geranylgeranyl pyrophosphate (or geranylgeranyl diphosphate). This reaction is an important step in tocotrienol biosynthesis and can result in the alteration of the tocol content and/or composition.

The invention provides isolated nucleotide molecules comprising nucleotide sequences encoding HGGT. Also provided are isolated polypeptides encoded by such nucleotide sequences. The nucleotide sequences find use in methods for altering tocols and tocotrienols in a biological system such as a plant. The methods include improving the antioxidant activity of grain, altering tocotrienols in a plant or part thereof, and improving tocols in a host. The methods comprise transforming a plant or host with at least one nucleotide construct comprising at least a portion of at least one nucleotide sequence of the invention. If desired, the nucleotide construct may additionally comprise an operably linked promoter that drives expression in the plant of interest. Such a nucleotide construct can be used to increase the expression of HGGT.

Among the many applications of improved tocols, tocotrienols and antioxidant activity are improved storage of grain, improved stability of oil extracted from grain, health benefits to humans and animals consuming the grain, and the production of novel tocols or tocotrienols for cosmetic, industrial and/or nutraceutical use. It is also known that the presence of tocols in plant vegetative green tissue such as leaf tissue is necessary to protect the plant from the photo-oxidative damage induced directly and indirectly by the production of free oxygen radicals in the chloroplast during oxygenic photosynthesis. It is therefore likely that ectopic expression of tocotrienols in green plant tissue, such as leaf tissue, in addition to the normal tocopherol content of the leaf will lead to an increase ability to withstand such photo-oxidative damage, and thus lead to an increase in the photosynthetic capacity of the plant. This would translate to an increase in harvestable yield for the plant over the entire growing season.

The nucleotide constructs of the invention comprise at least a portion of a nucleotide sequence of the invention. The nucleotide construct of the invention may additionally comprise at least one promoter that drives expression in a host or plant. Preferred promoters include, for corn, an embryo specific promoter such as promoters for the 16 kDa and 18 kDa oleosin genes, an endosperm specific promoter, such as the promoter for the 10 kDa zein gene, and a vegetative promoter such as promoters for ubiquitin genes.

A nucleotide construct of the invention comprises at least a portion of one nucleotide sequence of the invention. Preferably, such a nucleotide construct additionally comprises an operably linked promoter that drives expression in a plant. If desired, two or more of such nucleotide sequences may be linked or joined together to form one polynucleotide molecule, and such a polynucleotide may be used to transform a plant. For example, a nucleotide construct comprising a nucleotide sequence encoding a HGGT can be linked with another nucleotide sequence encoding the same or another HGGT. Nucleotide sequences encoding both HGGT and HPT may also be linked in a nucleotide construct. Similarly, the two nucleotide sequences can be provided on different nucleotide constructs, and each of the separate nucleotide sequences can be operably linked to a promoter that drives expression in a plant. For example, a construct may be used that increases total HGGT activity and decreases total HPT activity, thereby resulting in shunting the pathway towards the production of tocotrienols and decreased production of tocopherols. The alternative strategy may also be used. If separate nucleotide constructs are employed for the HGGT nucleotide sequence and an HPT nucleotide sequence, two individual plants may be transformed with the nucleotide constructs, and the plants may then be crossed to produce progeny having the desired genotype of both the HGGT and HPT nucleotide sequences.

Similarly, a construct to down-regulate the geranylgeranyl reductase responsible for producing phytol pyrophosphosphate, one of the precursors for tocopherol biosynthesis, may be linked in cis with a construct to express HGGT. The result of this manipulation would be an increased pool size of geranylgeranyl-pyrophosphate and a corresponding increase of flux into the tocotrienol biosynthetic pathway.

The methods of the present invention can be employed to alter tocols or tocotrienols in any plant or part thereof, and antioxidant activity may thereby be altered. Plants that may be used in the invention include field crops (e.g., alfalfa, barley, bean, maize, cotton, flax, pea, rape, rice, rye, safflower, sorghum, oats, millet, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); and fruit and nut crops (e.g., almond, apple, apricot, banana, blackberry, blueberry, cacao, cherry, coconut, cranberry, date, fajoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon) and *Arabidopsis*. Some methods of the invention involve altering the antioxidant levels in grain and other parts of a plant that may be subjected to post-harvest processing or can be used as food source for humans, livestock and other animals, such as pets. With post-harvest processing, the tocols or tocotrienols so produced can be a valuable source of recovery for millers and other processors.

Methods for assessing tocopherol content and tocopherol composition (including tocopherol activity) are known in the art. Tocopherol content and composition may be measured by HPLC in combination with fluorescence detection. Such methods are described in Example 2 and in numerous literature references (e.g., Kamal-Eldi A., Gorgen S., Pettersson J., Lampi A. M. (2000) J Chromatogr A 881:217-227; Bonvehi J. S., Coll F. V., Rius I. A. (2000) J. AOAC Intl. 83:627-634; Goffman F. D. and Böhme T. (2001) J Agric. Food Chem. 49:4990-4994). Such methods typically involve the resolution of tocopherol molecular species contained in complex mixtures by use of a normal or reverse phase HPLC matrix. Eluted tocopherol molecular species are then detected by fluorescence of the chromanol head group with an excitation wavelength typically in the range of 290 to 295 nm and an emission wavelength typically in the range of 325 to 335 nm. Using this methodology, the composition of a tocopherol mixture can be determined by comparing the retention times of separated molecular species with those of known standards. The content of each tocopherol molecular species can be measured by the relative intensity of its fluorescence emission at the selected wavelength. The absolute amount of each tocopherol species can be determined by measuring the intensity of fluorescence emission relative to that of an internal standard, which is added in a known amount to the tocopherol mixture prior to HPLC analysis. A suitable internal standard can include a tocopherol analog that is not normally found in nature (e.g., 5,7-dimethyltocol) or a naturally occurring tocopherol molecular species that is not present in a given tocopherol mixture. The total tocopherol content of a complex mixture of compounds can be derived by summing the absolute amount of each of the component tocopherol molecular species as determined by HPLC analysis.

Methods for assessing tocotrienol content and tocotrienol composition (including tocotrienol activity) are known in the art. Tocotrienol content and composition may be measured by HPLC using methods described above for the analysis of tocopherol content and composition. Using HPLC techniques described in Example 2 and elsewhere (e.g., Podda M., Weber C., Traber M. G., Packer L. (1996) J. Lipid Res. 37:893-901), tocotrienol molecular species can be readily resolved from tocopherol molecular species in a complex mixture. The occurrence and structural identification of tocotrienols in a complex mixture can be determined by gas chromatography-mass spectrometry as described by Frega N., Mozzon M., and Bocci F. (1998) J. Amer. Oil Chem. Soc. 75:1723-1728.

In addition, lipophilic antioxidant activity may be measured by assays including the inhibition of the coupled auto-oxidation of linoleic acid and β-carotene and oxygen radical absorbance capacity (ORAC) as described elsewhere (Serbinova E. A. and Packer L. (1994) Meth. Enzymol. 234: 354-366; Emmons C. L., Peterson D. M., Paul G. L. (1999) J. Agric. Food Chem. 47:4894-4898); Huang D et al (2002) J.Agric. Food Chem.) in the press. Such methods typically involve measuring the ability of antioxidant compounds (i.e., tocols) in test materials to inhibit the decline of fluorescence of a model substrate (fluorescein, phycoerythrin) induced by a peroxyl radical generator (2',2'-azobis[20amidinopropane] dihydrochloride).

The nucleotide constructs of the invention can also be used to decrease or suppress the expression of endogenous HGGT in a plant. Decreasing the expression of HGGT involved in the production of tocotrienol can serve to shift the tocol pathway toward the production of tocopherol. A plant can be transformed with the HGGT nucleotide sequences in the sense orientation for co-suppression or sense suppression of gene expression. Alternatively, the plant can be transformed with the HGGT nucleotide sequences in the antisense orientation for antisense suppression. Expression of HGGT polypeptides can also be suppressed by modifying genomic sequences in a plant by chimeraplasty. Generally, such modifications will alter the amino acid sequence of the polypeptides encoded by the genomic sequence as to reduce or eliminate the activity of a HGGT in a plant, particularly in a seed.

Compositions of the invention include nucleotide sequences encoding HGGT polypeptides that are involved in regulating tocols or tocotrienols. In particular, the present invention provides for isolated nucleic acid molecules comprising nucleotide sequences encoding the amino acid sequences shown in SEQ ID Nos: 2, 4, 6, 8 and 10. Further provided are polypeptides having an amino acid sequence encoded by a nucleic acid molecule described herein, for example those set forth in SEQ ID Nos: 1, 3, 5, 7, and 9, and fragments and variants thereof.

The invention encompasses isolated or substantially purified nucleic acid or polypeptide compositions. An "isolated" or "purified" nucleic acid molecule or polypeptide, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.3 kb or 0.1 kb of nucleotide sequences that naturally flank the nucleic acid molecule in genomic DNA of the cell from which the nucleic acid is derived. A polypeptide that is substantially free of cellular material includes preparations of polypeptide having less than about 30%, 20%, 10%, 5%, (by dry weight) of contaminating polypeptide. When the polypeptide of the invention or biologically active portion thereof is recombinantly produced, preferably culture medium represents less than about 30%, 20%, 10%, 5%, 3% or 1% (by dry weight) of chemical precursors or non-polypeptide-of-interest chemicals.

Fragments and variants of the disclosed nucleotide sequences and polypeptides encoded thereby are also encompassed by the present invention. By "fragment" is intended a portion of the nucleotide sequence or a portion of the amino acid sequence. Fragments of a nucleotide sequence may encode polypeptide fragments that retain the biological activity of the native protein and hence HGGT activity. Alternatively, fragments of a nucleotide sequence that are useful as hybridization probes generally do not encode polypeptides retaining biological activity. Thus, fragments of a nucleotide sequence may range from at least about 20 nucleotides, about 30 nucleotides, about 50 nucleotides, about 70 nucleotides, about 100 nucleotides, about 150 nucleotides and up to the full-length nucleotide sequence encoding the polypeptides of the invention.

A fragment of a HGGT nucleotide sequence that encodes a biologically active portion of an HGGT polypeptide of the invention will encode at least 15, 25, 30, 50, 75, 100, or 125 contiguous amino acids, or up to the total number of amino acids present in a full-length HGGT polypeptide of the invention (for example, 407, 408, 404, 380 and 361 amino acids for SEQ ID NO: 2, 4, 6, 8 and 10 respectively). Fragments of a HGGT nucleotide sequence that are useful as hybridization probes or PCR primers generally need not encode a biologically active portion of an HGGT polypeptide.

Thus, a fragment of an HGGT nucleotide sequence may encode a biologically active portion of an HGGT polypeptide, or it may be a fragment that can be used as a hybridization probe or PCR primer using methods disclosed below. A biologically active portion of an HGGT polypeptide can be prepared by isolating a portion of one of the HGGT nucleotide sequences of the invention, expressing the encoded portion of the HGGT polypeptide (e.g., by recombinant expression in vitro) and assessing the activity of the encoded portion of the HGGT polypeptide. Conserved motifs for HGGT sequences are identified in SEQ. ID Nos: 56-66.

Nucleic acid molecules that are fragments of an HGGT nucleotide sequence comprise at least 16, 20, 50, 75, 100, 150, 200, 250, 300, 350, 400, 450, 500, 550, 600, 650, or 700 nucleotides, or up to the number of nucleotides present in a full-length HGGT nucleotide sequence disclosed herein (for example, 1457, 1365, 1242, 1730, and 1769 nucleotides for SEQ ID NO: 1, 3, 5, 7 and 9, respectively). The coding sequences for the conserved motifs identified in SEQ. ID Nos: 56-66 can also be easily identified from the HGGT sequences provided herein. The same is also true of degenerate sequences coding for the conserved motifs identified in SEQ. ID Nos: 56-66.

By "variants" is intended substantially similar sequences. For nucleotide sequences, conservative variants include those sequences that, because of the degeneracy of the genetic code, encode the amino acid sequence of one of the HGGT polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an HGGT polypeptide of the invention. Generally, variants of a particular nucleotide sequence of the invention will have at least about 80% generally at least about 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters. Optionally, variants will also encode for at least any 1, 2, 3, 4, 5, 6, 7, 8, 9,10 or 11 of the conserved motifs identified in SEQ. ID Nos: 56-66.

By "variant" polypeptide is intended a polypeptide derived from the native polypeptide by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Variant polypeptides encompassed by the present invention are biologically active, that is they continue to possess the desired biological activity of the native polypeptide, that is, HGGT activity as described herein. Such variants may result from, for example, genetic polymorphism or from human manipulation. Biologically active variants of a native HGGT polypeptide of the invention will have at least about 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native polypeptide as determined by sequence alignment programs described elsewhere herein using default parameters. A biologically active variant of a polypeptide of the invention may differ from that polypeptide by as few as 1-15 amino acid residues, as few as 1-10, such as 6-10, as few as 5, as few as 4, 3, 2, or even 1 amino acid residue. Optionally, variants will also comprise at least any 1, 2, 3, 4, 5, 6, 7, 8, 9, 10 or 11 of the conserved motifs identified in SEQ. ID Nos: 56-66.

The polypeptides of the invention may be altered in various ways including amino acid substitutions, deletions, truncations, and insertions. Methods for such manipulations are generally known in the art. For example, amino acid sequence variants of the HGGT polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the polypeptides of the invention encompass both naturally occurring polypeptides as well as variations and modified forms thereof. Such variants will continue to possess the desired HGGT activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the polypeptide sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays. That is, the activity can be evaluated by assays for HGGT activity.

Variant nucleotide sequences and polypeptides also encompass sequences and polypeptides derived from a mutagenic and recombinogenic procedure such as DNA shuffling. With such a procedure, one or more different HGGT coding sequences can be manipulated to create a new HGGT polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the HGGT polynucleotides of the invention and/or other HGGT genes to obtain a new gene coding for a polypeptide with an improved property of interest, such as an increased Km in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire HGGT nucleotide sequences set forth herein or to fragments thereof are encompassed by the present invention. Such sequences include sequences that are orthologs of the disclosed sequences. By "orthologs" is intended polynucleotides derived from a common ancestral gene and which are found in different species as a result of speciation. Polynucleotides found in different species are considered orthologs when their nucleotide sequences and/or their encoded polypeptide sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

For clarification, "PCR" or "polymerase chain reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the HGGT sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire HGGT sequence disclosed herein, or one or more portions thereof, may be used as a probe capable of specifically hybridizing to corresponding HGGT sequences and messenger RNAs. To achieve specific hybridization under a variety of conditions, such probes include sequences that are unique among HGGT sequences and are preferably at least about 10 nucleotides in length, and most preferably at least about 20 nucleotides in length. Polynucleotide sequences useful as probes include the polynucleotide sequences encoding the conserved motifs set forth in SEQ. ID Nos: 56-66. Such probes may be used to amplify corresponding HGGT sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6(log M)+0.41(%GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated sequences that encode for a HGGT polypeptide and which hybridize under stringent conditions to the HGGT sequences disclosed herein, or to fragments thereof, are encompassed by the present invention.

Nucleotides (usually found in their T-monophosphate form) are often referred to herein by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "W" for A or T, "H" for A or C or T, "D" for A or G or T, "M" for A or C, "S" for C or G, "V" for A or C or G, "B" for C or G or T "I" for inosine, and "N" for A, C, G, or T.

The following terms are used to describe the sequence relationships between two or more nucleic acids or polynucleotides:(a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a polypeptide of the invention. BLAST polypeptide searches can be performed with the BLASTX program, score=50, wordlength=3, to obtain amino acid sequences homologous to a polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for polypeptides) can be used. See http://www.ncbi.hlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3;% similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for polypeptide sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

For purposes of the present invention, comparison of nucleotide or polypeptide sequences for determination of percent sequence identity to the HGGT sequences disclosed herein is preferably made using CLUSTAL with the following changes from the default parameters. For amino acid sequence comparisons a Gap Penalty of 10 and Gap Length Penalty of 10 was used for multiple alignments and a KTUPLE of 2, Gap Penalty of 3, Window of 5 and Diagonals Saved of 5 was used for pairwise alignments. For nucleotide sequence comparisons, a Gap Penalty of 10 and Gap Length Penalty of 10 was used for multiple alignments and a KTUPLE of 2, Gap Penalty of 5, Window of 4 and Diagonals Saved of 4 was used for pairwise alignments. Any equivalent program can also be used to determine percent sequence identity. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to polypeptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of polypeptides encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one polypeptide, or at least one RNA, such as, for example, an antisense RNA that is complementary to at least a portion of an mRNA. Typically such a nucleotide construct is comprised of a coding sequence for a polypeptide or an RNA operably linked to 5' and 3' transcriptional regulatory regions. Alternatively, it is also recognized that the methods of the invention may employ a nucleotide construct that is not capable of directing, in a transformed plant, the expression of a polypeptide or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731, 181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

The HGGT sequences of the invention are provided in expression cassettes for expression in the plant of interest. The cassette will include 5' and 3' regulatory sequences operably linked to a HGGT nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two polypeptide coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the HGGT nucleotide sequence to be under the transcriptional regulation of the regulatory regions. The expression cassette may additionally contain selectable marker genes.

The expression cassette will include in the 5'-3' direction of transcription, a transcriptional and translational initiation region, a HGGT polynucleotide sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of HGGT in the plant, plant cell or other host. Thus, the phenotype of the plant, plant cell or other host is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, chemically regulated, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemically regulated promoters can be used to modulate the expression of a gene in a plant through the application of an exogenous chemical regulator. Depending upon the objective, the promoter may be a chemical inducible promoter, where application of the chemical induces gene expression, or a chemical repressible promoter, where application of the chemical represses gene expression. Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced HGGT expression within a particular plant tissue. Tissue-preferred promoters include Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-specific promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1 129-1138; and Matsuoka et al. (1993) *Proc. Natl. Acad. Sci. USA* 90(20):9586-9590.

Root-specific promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase); (see WO 00/11177, herein incorporated by reference). The 27 kDa gamma-zein promoter is a preferred endosperm-specific promoter. The maize globulin-1 and oleosin promoters are preferred embryo-specific promoters. For dicots, seed-specific promoters include, but are not limited to, bean β-phaseolin, napin, β-conglycinin, soybean lectin, cruciferin, and the like. For monocots, seed-specific promoters include, but are not limited to, promoters of the 15 kDa beta-zein, 22 kDa alpha-zein, 27 kDa gamma-zein, waxy, shrunken 1, shrunken 2, globulin 1 and oleosin genes. See also WO 00/12733, where seed-preferred promoters from end1 and end2 genes are disclosed; herein incorporated by reference.

In a preferred embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts or other plastids. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The HGGT polypeptides of the invention can be targeted to specific compartments within the plant cell. Methods for targeting polypeptides to a specific compartment are known in the art. Generally, such methods involve modifying the nucleotide sequence encoding the polypeptide in such a manner as to add or remove specific amino acids from the polypeptide encoded thereby. Such amino acids comprise targeting signals for targeting the polypeptide to a specific compartment such as, for example, a the plastid, the nucleus, the endoplasmic reticulum, the vacuole, the mitochondrion, the peroxisome, the Golgi apparatus, and for secretion from the cell. Targeting sequences for targeting a polypeptide to a specific cellular compartment, or for secretion, are known to those of ordinary skill in the art. Chloroplast-targeting or plastid-targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase, as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp.177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

The invention involves transforming host cells with the nucleotide constructs of the invention. Generally, the nucleotide construct will comprise a HGGT nucleotide sequence of the invention, either a full length sequence or functional fragment thereof, operably linked to a promoter that drives expression in the host cell of interest. Host cells include, but are not limited to: plant cells; animal cells; fungal cells, particularly yeast cells; and bacterial cells.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Bio-technology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp.197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The nucleotide constructs of the invention may also be introduced into plants by contacting plants with a virus or viral nucleic acids. Generally, such methods involve incorporating a nucleotide construct of the invention within a viral DNA or RNA molecule. It is recognized that a HGGT of the invention may be initially synthesized as part of a viral polyprotein, which later may be processed by proteolysis in vivo or in vitro to produce the desired recombinant polypeptide. Further, it is recognized that promoters of the invention also encompass promoters utilized for transcription by viral RNA polymerases. Methods for introducing nucleotide constructs into plants and expressing a polypeptide encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Transformed plants include those plants directly transformed as provided herein, as well as plants that have the directly transformed plants in their pedigree and retain the change in genotype, such as the inclusion of the expression cassette, created by the original transformation.

The present invention may be used for transformation of any plant species, including, but not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vul-* garis), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, barley, rice, sorghum, rye, millet, tobacco, etc.), more preferably cereal plants, yet more preferably corn, wheat, barley, rice, sorghum, rye and millet plants.

It is recognized that with these nucleotide sequences, antisense constructions, complementary to at least a portion of the messenger RNA (mRNA) for a HGGT sequence can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a nucleotide construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The following examples are presented by way of illustration, not by way of limitation.

Experimental

The present invention is further defined in the following Examples, in which parts and percentages are by weight and degrees are Celsius, unless otherwise stated. It should be understood that these Examples, while indicating preferred embodiments of the invention, are given by way of illustration, not by way of limitation. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

EXAMPLE 1

Composition of cDNA Libraries

Isolation and Sequencing of cDNA Clones cDNA libraries representing mRNAs from various barley (*Hordeum vulgare*), corn (*Zea mays*), rice (*Oryza sativa*) and wheat (*Triticum aestivum*) tissues were prepared. The cDNA libraries representing mRNAs from barley (*Hordeum vulgare*) and rice (*Oryza sativa*) developing seeds are described in Examples 2 and 4, respectively. The characteristics of the corn (*Zea mays*) and wheat (*Triticum aestivum*) libraries are described in Table 1 below.

TABLE 1 cDNA Libraries from Corn and Wheat

| Library | Tissue | Clone |
|---|---|---|
| cco1n | Corn (*Zea mays*) cob of 67 day old plants grown in green house* | cco1n.pk087.l17:fis |
| wdk2c | Wheat (*Triticum aestivum*) developing kernel, 7 days after anthesis | wdk2c.pk012.f2:fis |
| p0058 | Sweet Corn (*Zea mays*) hybrid (Honey N Pearl) shoot culture. It was initiated on Feb. 28, 1996 from seed derived meristems. The culture was maintained on 273N medium. | p0058.chpbj67r:fis |

These libraries were normalized essentially as described in U.S. Pat. No. 5,482,845 (the contents of which are hereby incorporated by reference).

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al. (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

EXAMPLE 2

Identification and Functional Characterization of a Homogentisate Geranylgeranyl Transferase (HGGT) cDNA from Barley Seed In an attempt to identify cDNAs for homogentisate geranylgeranyl transferase (HGGT), degenerate PCR oligonucleotides were designed based on partially conserved domains in amino acid sequences deduced from homogentisate phytyl transferase (HPT) cDNAs disclosed in WO 00/68393 (the contents of which are hereby incorporated by reference). Degenerate sense and antisense oligonucleotides were designed that consist of the following sequences: 5'-TAYRT-NGTNGGNHTNAAYCA-3' (SEQ ID NO:20) and 5'-GCR-TARAANARNTTCCADATRAA-3' (SEQ ID NO:22). These oligonucleotides were designated HPT5' (SEQ ID NO:20) and HPT3' (SEQ ID NO:22), respectively, and correspond to the amino acid sequences: Y(IN)VG(I/L/F/M)NQ (SEQ ID NO:21) and FIW(K/N)(I/L/M)FYA (SEQ ID NO:23).

It is known that tocotrienols are enriched in the seed endosperm of monocotyledonous plants, including barley (*Hordeum vulgare*) (The Lipid Handbook, 2nd Edition, Gunstone, F. D., et al., Eds., Chapman and Hall, London, 1994, pp.129-131; Qureshi, A. A. et al., (1986) *J. Biol. Chem.* 261: 10544-10550). Such tissues therefore represent likely sources of expressed genes for the tocotrienol biosynthetic enzyme HGGT. As a first step towards the identification of an HGGT cDNA, total RNA was isolated from developing seeds of barley (cultivar Barsoy) using Trizol reagent (Life Technologies) according to the manufacturer's protocol. First strand cDNA was then prepared from 2 µg of the isolated RNA by using oligo-dT priming and Superscript II reverse transcriptase (Life Technologies) in a 25 µL reaction as described in the manufacturer's protocol. PCR amplification was then conducted using Advantage cDNA polymerase mix (Clontech) and 2 µL of the first strand cDNA synthesis reaction as template in a total volume of 50 µL. Oligonucleotides HPT5' (SEQ ID NO: 20) and HPT3' (SEQ ID NO: 22) were included in the amplification reaction as sense and antisense primers. Forty cycles of amplification were conducted with annealing and extension temperatures of 50° C. and 72° C., respectively. The resulting PCR products displayed an approximate size of 700 nucleotides, as expected for the coding sequence of HPT-related enzymes. PCR products were subsequently subcloned into the vector pPCR-Script AMP (Stratagene) according to the manufacturer's protocol and transformed into *E. coli* DH10B cells (Gibco-BRL). Nucleotide sequence was obtained from the cDNA inserts of plasmids from twelve of the resulting colonies. The sequence of one cDNA insert (SEQ ID NO: 11) was found to encode 234 amino acids of an HPT-related polypeptide (SEQ ID NO: 12) that shared 58 to 61% identity with the analogous portion of HPT polypeptides from *Arabidopsis* (SEQ ID NO: 13), soybean (SEQ ID NO: 14), rice (SEQ ID NO: 15) and maize (SEQ ID NO: 16) that were disclosed in WO 00/68393. Over the same portion of their amino acid sequences, the *Arabidopsis*, soybean, rice and maize HPTs share >75% identity. Thus, the partial cDNA sequence identified from barley seeds encoded a divergent form of HPT that was subsequently determined to correspond to the polynucleotide sequence for HGGT.

In order to establish the function of the polypeptide encoded by the partial cDNA from barley seed, the complete 5' and 3' ends of the cDNA were amplified from a barley developing seed cDNA library using nested PCR. As used herein, the term "nested PCR" refers to a polymerase chain reaction (PCR) technique in which the product or products of a PCR reaction are reamplified by using an oligonucleotide primer combination in which one or both primers correspond to a portion of the target DNA that lies within the sequence amplified in the initial reaction. For the library construction, polyA+-RNA was enriched from the developing seed total RNA described above using the QuickPrep mRNA purification kit (Pharmacia Biotech) according to the manufacturer's protocol. cDNA inserts were prepared from the poly-A+ RNA using a Uni-ZAP XR cDNA synthesis kit (Stratagene) and cloned into the EcoRI/XhoI sites of the pBluescript SK(+) vector as previously described (Cahoon et al. (1999) *Proc. Natl. Acad. Sci. USA* 96:12935-12940). Approximately 200 ng of the resulting plasmid library was used as template in nested PCR reactions described below. The reactions were conducted in 50-μL volumes, and amplification was achieved using Advantage cDNA polymerase mix (Clontech) with an annealing temperature of 55° C. Reactions contained primer pairs that were designed based on sequence from the pBluescript SK(+) vector and from the partial cDNA amplified from barley seed (SEQ ID NO: 11). Thirty-five cycles were conducted in each of the PCR reactions described below. For amplification of the complete 5' end of the putative barley HGGT cDNA, reactions were performed with the following sense and antisense primers: 5'-AAATTAACCCTCAC-TAAAGGG-3' (modified T3 primer) (SEQ ID NO: 24) and 5'-ATACATGATGCAGCGAGGAGC-3' (SEQ ID NO:25). The unpurified products of this reaction were diluted six-fold, and 1 μL of this dilution was used as template in a second reaction that contained the following nested sense and antisense primers: 5'-CTCTAGAACTAGTGGATCCC-3' (modified SK primer) (SEQ ID NO: 26) and 5'-GTATTCCTAT-GCTAAAGCTC-3' (SEQ ID NO: 27). For amplification of the complete 3'end of the putative barley HGGT cDNA, reactions were conducted with the following sense and antisense primers: 5'-GAATTTTCAGTAGCAACTGG-3' (SEQ ID NO: 28) and 5'-GTAAAACGACGGCCAGT-3' (M13-20 primer) (SEQ ID NO: 29). The unpurified products of this reaction were diluted six-fold, and 1 μL of this dilution was used as template in a second reaction that contained the following nested sense and antisense primers: 5'-CTCCTCGCT-GCATCATGTATC-3' (SEQ ID NO: 30) and 5'-GTAATAC-GACTCACTATAGGGC-3' (T7 primer) (SEQ ID NO: 31). The products of the nested reactions above were subcloned into the vector PGEM-T Easy (Promega), and transformed into *E. coli* DH10B cells. DNA sequences corresponding to the amplified 5' and 3' ends of the putative barley HGGT cDNA were then obtained from cDNA inserts of plasmids from several independent transformants. These sequences together with that from SEQ ID NO: 11 were assembled to generate the sequence of the full-length cDNA for the putative barley HGGT (SEQ ID NO: 1). The resulting full-length cDNA was designated "bdl2c.pk006.o2". The bdl2c.pk006.o2 cDNA (SEQ ID NO: 1) was found to encode a 407 amino acid polypeptide (SEQ ID NO: 2) that shares 45 to 47% identity with HPTs from *Arabidopsis* (SEQ ID NO: 13), soybean (SEQ ID NO: 14), rice (SEQ ID NO: 15) and maize (SEQ ID NO: 16) that were disclosed in WO 00/68393. By comparison, the *Arabidopsis*, soybean, rice, and maize HPTs share 61 to 69% identity with each other.

To examine the tissue-specific expression of the gene for the putative barley HGGT polypeptide, Northern blot analysis was conducted using polyA+-enriched RNA isolated from leaf, roots and developing seeds of barley. For this experiment, total RNA was isolated from these tissues using the Trizol reagent (Life Technologies) according to the manufacturer's protocol, and polyA+ RNA was then enriched from the total RNA extract using the PolyATract mRNA isolation system (Promega). Approximately 2 μg of polyA+ from each tissue was electrophoresed in a 1% (w/v) agarose gel and then transferred from the gel to Bright Star-Plus nylon membrane (Ambion) using NorthernMax transfer buffer (Ambion). The RNA was fixed to the membrane by baking at 80° C. for 2 h. The membrane was rinsed with 2×SSC and then hybridized with $^{32}$P-labeled probes for 18 h at 42° C. in NorthernMax hybridization buffer (Ambion). Probes were prepared from the full-length barley HPT-like cDNA (bdl2c.pk006.o2; SEQ ID NO: 1) and were labeled using random hexamer priming. Following incubation with probes, blots were washed for 15 min with 2×SSC/0.1% SDS at room temperature, then washed for a 15 min at room temperature with 0.2×SSC/0.1% SDS, and finally washed for 15 min at 42° C. with 0.2×SSC/0.1% SDS. Radioactivity on filters was detected by phosphorimaging. As a control for RNA loading, the Northern blot was re-hybridized with a labeled probe prepared from a barley α-tubulin cDNA, which corresponds to a constitutively expressed gene.

A Northern blot analysis to assess the expression of a nucleotide sequence encoding a barley HGGT was performed. Enriched polyA+ RNA isolated from leaf (L), root (R), and developing seed (S) of barley were analyzed. A barley a-tubulin gene, which is known to be a constitutively expressed gene in plants was analyzed using the same Northern blot as for HGGT gene expression and showed that the loading of polyA+ RNA from each tissue was approximately equal.

Expression of the gene for the putative barley HGGT was detected in developing seeds but was not detected in leaves and roots. The seed specific expression of the gene for the putative barley HGGT is consistent with the occurrence of tocotrienols in barley seeds and the corresponding absence of these compounds from leaves and roots (Cahoon, unpublished observation).

To determine the function of the putative barley HGGT, the full-length bdl2c.pk006.o2 cDNA (SEQ ID NO: 1) encoding this enzyme was operably linked to the cauliflower mosaic virus 35S promoter and expressed in tobacco callus. The barley cDNA was initially amplified by PCR to generate flanking NcoI and EcoRI sites for cloning into the plant expression vector. The sequence of the sense oligonucleotide used in the amplification reaction was 5'-tt ccatggCGAGGATGCAAGCCGTCACGG-3' (SEQ ID NO: 32), and the sequence of the antisense oligonucleotide was 5'-ttgaattcACACATCTGCTGGCCCTTGTAC-3' (SEQ ID NO: 33). (Note: The bases in lower case contain the added restriction sites, which are underlined, and flanking sequence to facilitate restriction enzyme digestion.) Thirty cycles of PCR amplification were conducted in a 100 μL volume using Pfu polymerase (Stratagene) and approximately 300 ng of the barley developing seed cDNA library described above as template. The product of this reaction was purified by agarose electrophoresis, and then digested with the restriction enzymes NcoI and EcoRI. The amplified barley cDNA was then cloned into the corresponding sites of the plant expression vector pML63. A detailed description of vector pML63 has been previously disclosed in WO 00/11176 (the contents of which are hereby incorporated by reference). The resulting plasmid pBHGGT-35S contained the putative barley HGGT cDNA operably linked at its 5' end to the cauliflower mosaic virus 35S promoter and at its 3' end to termination sequence from the nopaline synthase (nos) gene. This expression cassette was then removed from pBHGGT-35S following digestion with the restriction enzyme SalI and cloned into the corresponding restriction site of the binary vector pZS199 to generate plasmid pSH24. Vector pZS199 was described in detail in WO 00/11176. The vector contains right and left T-DNA borders for integration of the expression cassette into the host plant genome and a neomycin phosphotransferase II gene linked to a cauliflower mosaic virus 35S promoter, which confers kanamycin selection for transgenic plant cells.

Plasmid pSH24, which contains a fusion of the barley putative HGGT cDNA with the cauliflower mosaic virus 35S promoter and the nos termination sequences in vector pZS199, was introduced into *Agrobacterium tumefaciens* strain LBA4404 by electroporation. Cultures derived from these cells were used for transformation of tobacco (*Nicotiana tabacum* cv. Xanthi) leaf disks according to the protocol described by Rogers, S. G., Horsch, R. B., and Fraley, R. T. (1986) *Methods Enzymol.* 118:627-648. Tobacco leaf disks were also transformed with *A. tumefaciens* harboring only the pZS199 vector. Transformed tobacco callus was selected by the ability of cells to grow on media containing kanamycin at a concentration of 300 mg/L. In addition, expression of the transgene in these cells was confirmed by Northern blot analysis using a radiolabeled probe derived from the full-length barley putative HGGT cDNA (bdl2c.pk006.o2 cDNA; SEQ ID NO: 1).

Transformed callus arising from leaf disks was analyzed for tocotrienol production following ten to twelve days of growth on fresh kanamycin-containing media. Analyses were conducted using 10 to 50 mg (dry weight) of lyophilized tobacco callus. The transgenic tissue was initially homogenized in 3 mL of methanol:chloroform (2:1 v/v) in a 13×100 mm glass test tube. Following 2 h of incubation, 1 mL of chloroform and 1.8 mL of water were added. The organic and aqueous layers were thoroughly mixed and then partitioned by centrifugation. The organic layer was recovered, dried under nitrogen, and resuspended in 175 µL of heptane. The tocopherol and tocotrienol content of the organic extract was then determined using HPLC. Resolution of these compounds was achieved using a Hewlett Packard LiChroSpher Si 60 column (25 cm length; 5µ particle size) and a solvent system consisting of heptane:isopropanol (99:1 v/v) with a flow rate of 1 mL/min. Analytes were detected and quantified by fluorescence with excitation at 292 nm and emission at 335 nm. Tocopherol and tocotrienol molecular species were identified by mobility relative to standard compounds and quantified relative to δ-tocopherol, which was added as an internal standard. Using this methodology, tobacco callus expressing the barley putative HGGT cDNA was found to contain the following tocotrienol species: α-, β-, γ- and δ-tocotrienol. In contrast, no tocotrienols were detected in tobacco callus transformed with only the pZS199 expression vector. In these studies, expression of the barley HGGT cDNA was mediated by the cauliflower mosaic virus 35S promoter. The analyses were conducted using an equivalent amount of tobacco callus.

This result thus demonstrates that the barley bdl2c.pk006.o2 cDNA disclosed in SEQ ID NO: 1 encodes a functional homogentisate geranylgeranyl transferase (HGGT) whose expression in transgenic plant cells results in tocotrienol production. Amounts of tocotrienol in tobacco callus expressing the barley HGGT cDNA were as high as 164.7-mg/kg dry weight, and the total tocopherol and tocotrienol content of these cells was as much as ten-fold higher than that in cells transformed with only the pZS199 vector (Table 2).

TABLE 2

Total tocopherol and tocotrienol content of tobacco callus transformed with the binary vector pZS199 (Vector Control) or with the barley HGGT cDNA operably linked to the cauliflower mosaic virus 35S promoter in pZS199 (+Barley HGGT cDNA). (The values shown were obtained from independent transgenic events.)

| Transgenic Events | Total Tocopherol Content (mg/kg dry weight) | Total Tocotrienol Content (mg/kg dry weight) |
|---|---|---|
| Vector Control | | |
| Event 1 | 17.5 | n.d.* |
| Event 2 | 16.4 | n.d. |
| Event 3 | 12.8 | n.d. |
| Event 4 | 14.6 | n.d. |
| +Barley HGGT cDNA | | |
| Event 1 | 11.8 | 161.1 |
| Event 2 | 14.0 | 155.4 |
| Event 3 | 12.3 | 118.5 |
| Event 4 | 14.3 | 164.7 |
| Event 5 | 9.7 | 121.1 |

*n.d., not detected.

To confirm the identity of tocotrienols in transgenic tobacco callus expressing the barley HGGT cDNA, the organic extract from these cells was analyzed by gas chromatography-mass spectrometry. These analyses were performed using a Hewlett Packard 6890 gas chromatograph interfaced with a Hewlett Packard 5973 mass selective detector (MSD). Samples were separated with a 15-m×0.25-mm (inner diameter) DB-1 HT column (J&W Scientific). The oven temperature was programmed from 125° C. (4-min hold) to 240° C. (12-min hold) at a rate of 10° C./min. The ionization potential of the MSD was 70 eV. Using these conditions, compounds were detected with mass spectra identical to those of tocotrienol standards. The mass spectra of α- and γ-tocotrienol that were detected in extracts of tobacco callus expressing the barley HGGT cDNA contained molecular ions for α-tocotrienol (m/z 424) and γ-tocotrienol (m/z 410) as well as $M^+$-219 ions arising from loss of the side chain and $M^+$-259 ions arising from cleavage of the chroman ring and accompanying rearrangement as described (Nair and Zenaida (1968) *Arch. Biochem. Biophys.* 127:413-418).

These results conclusively demonstrate the ability to produce tocotrienols and to increase tocol content in transgenic plant cells by overexpression of the barley HGGT cDNA.

EXAMPLE 3

Identification and Functional Characterization of a Homogentisate Geranylgeranyl Transferase (HGGT) cDNA from Wheat Seed Wheat seeds and derivatives such as wheat bran and kernel are enriched in tocotrienols (Shin, T. S. (1994) *J. Chromatogr. A* 678:49-58) and thus represent potential sources of an HGGT cDNA. Homology searches were conducted using the nucleotide sequence of the barley HGGT cDNA (SEQ ID NO: 1) and expressed sequence tags (ESTs) generated from developing wheat kernel. These searches resulted in the identification of wheat EST wdk2c.pk012.f2:fis (SEQ ID NO: 34) that shared 94% identity with the barley HGGT cDNA (SEQ ID NO:1) over a span of 321 nucleotides. This high degree of sequence identity suggested that EST wdk2c.pk012.f2:fis (SEQ ID NO: 34) encodes an HGGT polypeptide. Based on sequence comparisons with the cDNA for barley HGGT (SEQ ID NO: 1), the cDNA corresponding to EST wdk2c.pk012.f2:fis (SEQ ID NO: 34) lacked coding sequence for at least 200 N-terminal amino acids. Functional characterization of the wheat HGGT-like polypeptide corresponding to EST wdk2c.pk 012.f2:fis (SEQ ID NO: 34) thus required isolation of additional 5' coding sequence.

Nested PCR was conducted to isolate a full-length cDNA for the wheat HGGT-like polypeptide. The template for the initial amplification reaction consisted of 25 ng of a mixture of cDNA libraries prepared from developing kernels, roots and seedlings of wheat. The libraries consisted of cDNA inserts cloned into the plasmid pBluescript SK(+). The sense oligonucleotide primer for this reaction corresponded to sequence in pBluescript SK(+) that flanks the 5' end of cDNA inserts, and the antisense primer corresponded to sequence in the ESTwdk2c.pk012.f2:fis (SEQ ID NO: 34). The sequences of the corresponding primers were as follows: 5'-GC-CAAGCTCGGAATTAACCCTCA-3' (sense) (SEQ ID NO: 35) and 5'-CACAGTACAAGGAAAATCCAAGCA-3' (antisense) (SEQ ID NO: 36). The reaction was conducted in a volume of 20 μL, and amplification was achieved using Advantage cDNA polymerase mix. The initial PCR cycling conditions were as follows: denaturation at 94° C. for 30 s, annealing at 68° C. for 30 s, and extension at 72° C. for 4 min. The annealing temperature was then lowered by 0.5° C. for each of the subsequent 9 cycles. This was then followed by 25 cycles with an annealing temperature of 63° C. The unpurified product of this reaction was then diluted 200-fold and used as template in a reaction that was conducted using the same amplification conditions as in the first reaction. The respective sense and antisense primers for this reaction corresponded to sequences in pBluescript SK(+) and EST wd2 kc.pk012.f2:fis (SEQ ID NO: 34) that were flanked by the primers from the first reaction. The sequences of these "nested" oligonucleotide primers used in the second reaction were as follows: 5'-GCCGCTCTAGAACTAGTGGATC-CCC-3' (sense) (SEQ ID NO: 37) and 5'-TCCAAGCATTG-GATAGGGTATCA-3' (antisense) (SEQ ID NO: 38). The product of this second PCR reaction was subcloned into the vector PGEM-T Easy (Promega) according to the manufacturer's protocol, and complete DNA sequence was subsequently obtained from the subcloned PCR products. Using this methodology, full-length coding sequence was obtained for a 408 amino acid polypeptide that shared 86.7% identity with the barley HGGT. The sequences of the full-length cDNA (designated "wdk2c.pk012.f2:cgs") from wheat and the corresponding polypeptide are disclosed in SEQ ID NO: 3 and SEQ ID NO: 4, respectively.

In order to establish the function of the wheat HGGT-like polypeptide in SEQ ID NO: 4, the corresponding wdk2c.pk012.f2:cgs cDNA (SEQ ID NO: 3) was operably linked to a cauliflower mosaic virus 35S promoter and expressed in tobacco callus. The complete open-reading frame of the wheat cDNA was initially amplified by PCR with oligonucleotides that contained added restriction enzyme sites to facilitate cloning into the plant expression vector. The oligonucleotide primers used for the PCR reaction were as follows: 5'-ttggaattcGTGGCCGCCCGGCGAGGATGC-3' (sense) (SEQ ID NO: 39) and 5'-tt ggtaccTCACATCTGCTGGCCCTTGTAC-3' (antisense) (SEQ ID NO: 40). (Note: The bases in lower case contain the added restriction sites, which are underlined, and flanking sequence to facilitate restriction enzyme digestion.) The template for the reaction was the wheat HGGT-like cDNA (wdk2c.pk012.f2:cgs; SEQ ID NO: 3) cloned in PGEM-T Easy, and amplification was achieved using Pfu polymerase (Stratgene). The product of this reaction was purified by agarose gel electrophoresis, digested with EcoRI and KpnI, and cloned into the corresponding sites of the plant expression vector pML135 to generate the plasmid pWhtHGGT-35S. The vector pML135 was generated from vector pML63, which has been described previously in WO 00/11176 (the contents of which are hereby incorporated by reference), by replacement of the beta-glucuronidase (GUS) gene with a polylinker that contained the restriction enzyme recognition sites for PmlI, EcoRI, SmaI, and KpnI. pWhtHGGT-35S contains the open-reading frame of the wheat HGGT-like cDNA (wdk2c.pk012.f2:cgs; SEQ ID NO: 3) flanked on its 5'-end by the cauliflower mosaic virus 35S promoter and on its 3'-end by transcriptional termination sequence for the nopaline synthase gene. This expression cassette was subsequently moved as a SalI fragment from pWhtHGGT-35S and cloned into the corresponding site of the binary vector pZS199 (described in Example 2) to generate the plasmid pEC17. *Agrobacterium tumefaciens* LBA4404 cells were subsequently transformed as described in Example 2. The transformed *A. tumefaciens* cells were then used for infection of tobacco (*Nicotiana tabacum* cv. Xanthi) leaf disks using protocols detailed in Example 2.

The resulting tobacco callus transformed with the wheat HGGT-like cDNA (wdk2c.pk012.f2:cgs; SEQ ID NO: 3) operably linked to the cauliflower mosaic virus 35S promoter was maintained and analyzed for tocopherol and tocotrienol content as described in Example 2. Tobacco callus expressing the wheat HGGT cDNA accumulated molecular species of tocotrienols including α-, β-, γ- and δ-tocotrienol. Of five independent events analyzed, amounts of tocotrienols detected were as high as 140 mg/kg (dry weight). In contrast, no tocotrienol accumulation was detected in tobacco callus transformed with the pZS199 binary vector lacking cDNA insert. The analyses were conducted using an equivalent amount of tobacco callus.

These results thus demonstrate that the wheat wdk2c.pk012.f2:cgs cDNA disclosed SEQ ID NO: 3 encodes a functional HGGT polypeptide whose expression in transgenic plant cells results in the production of tocotrienols.

EXAMPLE 4

Identification and Functional Characterization of a Homogentisate Geranylgeranyl Transferase (HGGT) cDNA from Rice Seed Rice seeds and byproducts such as rice bran are enriched in tocotrienols (The Lipid Handbook, 2nd Edition, Gunstone, F. D., et al., Eds., Chapman and Hall, London, 1994, pp. 129-131) and are thus potential sources of homogentisate geranylgeranyl transferase (HGGT) cDNAs. Using methodology similar to that described in Example 2, isolation of a HGGT cDNA from rice seed was achieved through a PCR strategy that employed degenerate oligonucleotide primers designed from partially conserved domains in homogentisate phytyltransferases (HPTs) disclosed in WO 00/68393. The term "degenerate oligonucleotide" refers to a synthesized mixture of a nucleotide sequence in which a given position within the sequence can be represented by more than one nucleotide in the mixture. The template for PCR amplification reactions was a cDNA library prepared from developing rice seeds harvested at two to five days after pollination. The protocols for RNA isolation from rice seeds and synthesis of cDNA inserts were the same as those used in the preparation of a barley developing seed cDNA library described in Example 2. The resulting cDNA inserts were cloned in a 5'→3' orientation into the EcoRI and XhoI sites of the Lambda Uni-ZAP XR phage vector (Stratagene). The vector containing the developing rice seed cDNA inserts was then packaged and subsequently amplified according to the manufacturer's protocol (Stratagene).

The resulting rice developing seed cDNA library was used as template for PCR amplification at a total amount of 5×10$^6$ plaque-forming units in a 50-μL reaction volume. The degenerate oligonucleotides HPT5' (SEQ ID NO: 20) and HPT3' (SEQ ID NO: 22) (as described in Example 2) were used as the sense and antisense primers, respectively. These primers were included in the reaction at a final concentration of 1.5 μM. Amplification was achieved using Advantage cDNA polymerase mix (Clontech). Forty amplification cycles were conducted using the following temperatures and times for each cycle: 94° C. for 1 min, 50° C. for 1 min, and 72° C. for 1.25 min. The unpurified product of this reaction was diluted seven-fold, and 1 uL of this dilution was used as template in a second PCR reaction. This reaction was conducted using the same reaction conditions as above. HPT3' (SEQ ID NO: 22) was again used as the antisense primer, and HPT5' (SEQ ID NO: 20) was replaced as the sense primer with the degenerate oligonucleotide HPT5'-2 (SEQ ID NO: 41), which contained the following sequence: 5'-ATHGAYAARRT-NAAYAARCC-3' (SEQ ID NO: 41). This oligonucleotide corresponds to the amino acid sequence IDK(I/V/M)NKP (SEQ ID NO: 42), which is a partially conserved domain in HPT sequences disclosed in WO 00/68393. The coding sequence of this domain corresponds to a region upstream of the HPT5' sequence in HPT cDNAs. Using the HPT5'-2 (SEQ ID NO: 41) and HPT3' primers (SEQ ID NO: 22), products of approximately 700 bp were obtained from the second PCR reaction. The products were then purified and subcloned into vector PGEM-T Easy (Promega) according to the manufacturer's protocol. Upon partial sequencing, one of the PCR products was found to encode a polypeptide that was more related to HGGTs from barley and wheat than to HPTs disclosed in WO 00/68393.

Functional characterization of this putative rice HGGT required isolation of additional 5' and 3' sequence for the complete N'- and C'-termini of this polypeptide. This was achieved through a series of nested PCR reactions in which the rice developing seed cDNA library (described above) was used as the template. For all PCR reactions described below, forty amplification cycles were conducted using Advantage cDNA polymerase mix (Clontech) and the temperatures and times for each cycle were as follows: 94° C. for 1 min, 53° C. for 1 min, and 72° C. for 1.25 min. For isolation of the coding sequence of the complete C' terminus, sense oligonucleotide primers were designed based on the sequence of the PCR product encoding the partial rice HGGT-like polypeptide, and antisense primers were designed based on sequences in the Lambda Uni-Zap cDNA library vector. A PCR reaction was initially conducted that contained an aliquot of the rice developing seed cDNA library (5×10$^6$ plaque-forming units) and the following sense and antisense primers: 5'-GGAAGTG-CATACTCTGTTGATG-3' (SEQ ID NO: 43) and 5'GTAAAACGACGGCCAGT-3' (M13-20 primer) (SEQ ID NO: 29). The unpurified products of this reaction were diluted 10-fold, and 1 μL of this dilution was used as template in a second reaction that contained the following nested sense and antisense primers: 5'-CTTGTATACTATTTGTAAGAGC-3' (SEQ ID NO: 44) and 5'-GTAATACGACTCACTAT-AGGGC-3' (T7 primer) (SEQ ID NO: 31). The product of this reaction was purified by agarose gel electrophoresis and sub-cloned into the vector PGEM-T Easy (Promega) using the method described by the manufacturer. Nucleotide sequence was then obtained for the entire subcloned PCR product. Comparison of the resulting sequence with those of barley and wheat HGGTs indicated that the PCR product encoded the complete C'-terminus of an HGGT-like polypeptide. For isolation of the coding sequence of the complete N'-terminus of the rice HGGT-like polypeptide, sense primers were designed based on sequences in the Lambda Uni-Zap cDNA library vector. The design of antisense primers was based on the coding sequence obtained for the C'-terminus of the rice HGGT-like polypeptide. A PCR reaction was initially conducted that contained an aliquot of the rice developing seed cDNA library (5×10$^6$ plaque-forming units) and the following sense and antisense primers: 5'-AACAGCTATGAC-CATG-3' (M13 reverse) (SEQ ID NO: 45) and 5'-ATAAT-TGCTCATGTGCATGGTC-3' (SEQ ID NO: 46). The unpurified products of this reaction were diluted 10-fold, and 1 μL of this dilution was used as template in a second reaction that contained the following nested sense and antisense primers: 5'-AAATTAACCCTCACTAAAGGG-3' (modified T3 primer) (SEQ ID NO: 24) and 5'-CATGTAAATGATGT-GATCCAC-3' (SEQ ID NO: 47). The product of this reaction was purified by agarose gel electrophoresis and subcloned into the vector PGEM-T Easy (Promega) according to the manufacturer's protocol. Results of sequence analysis indicated that the PCR product contained the coding region for the complete N'-terminus of an HGGT-like polypeptide (relative to barley and wheat HGGTs described in Examples 2 and 3).

Using the sequence information obtained above, the complete open-reading frame for the rice HGGT-like polypeptide was then amplified by PCR from the rice developing seed cDNA library. The oligonucleotide primers used in this reaction corresponded to sequences that flanked the open-reading frame of the rice HGGT-like polypeptide. These primers contained the following sequences: 5'-tt gcggccgcAGACGATGCAAGCCTCATCGG-3' (sense) (SEQ ID NO: 48) and 5'-tt gcggccgcCTTGCCCTTGTGTATATAGTGC-3' (antisense) (SEQ ID NO: 49). (Note: The lower case, underlined sequence corresponds to an added NotI restriction site. The remaining lower case sequence was added to facilitate restriction enzyme digestion.) PCR amplification was conducted using Advantage cDNA polymerase mix and an aliquot of the rice developing seed cDNA library (3.5×10$^6$ plaque-forming units) in a 50 μL reaction volume. Thirty-five amplification cycles were performed using an annealing temperature of 57° C. The resulting cDNA product was purified by agarose electrophoresis and sub-cloned into the PGEM-T Easy vector (Promega) according to the manufacturer's protocol. The sequence obtained from this cDNA (designated "rds1c.pk007.m9") is disclosed in SEQ ID NO: 5, and the deduced amino acid sequence is disclosed in SEQ ID NO: 6. The polypeptide encoded by the PCR product shared 68.6% amino acid sequence identity with the barley HGGT (SEQ ID NO: 2) and 66.3% identity with the wheat HGGT (SEQ ID NO: 4).

Functional characterization of the putative rice HGGT polypeptide (SEQ ID NO: 6) was conducted by transgenic expression in tobacco callus. For these studies, the coding sequence of the putative rice HGGT (SEQ ID NO: 6) was operably linked to the cauliflower mosaic virus 35S promoter. To facilitate cloning into the plant expression vector, the coding sequence of the putative rice HGGT was amplified with primers that contained a flanking SmaI and KpnI restriction sites, which are underlined in the sequences below. The sequences of the oligonucleotide primers used in this reaction were as follows: 5'-TT CCCGGGAGACGATGCAAGCCTCATCG-3' (sense) (SEQ ID NO: 50) and 5'-TT GGTACCGTGTATATAGTGCTCACTGCAC-3' (antisense) (SEQ ID NO: 51). PCR amplification was conducted with Pfu polymerase, and the rice putative HGGT cDNA (rds1c.pk007.m9; SEQ ID NO: 5 was used as the template. The product of this reaction was purified by agarose gel electrophoresis, digested with SmaI and KpnI, and then cloned into the corresponding restriction sites of the plant expression vector pML135 (which is described in Example 3). The resulting plasmid pRiceHGGT-35S contained an expression cassette consisting of the putative rice HGGT open reading frame flanked on its 5'-end by the cauliflower mosaic virus 35S promoter and on its 3'-end by transcriptional termination sequence for the nopaline synthase (nos) gene. This expression cassette was then inserted as a SalI restriction fragment into the corresponding site of the binary vector pZS199 (which is described in WO 00/11176 (the contents of which are hereby incorporated by reference) and in Examples 2 and 3) to generate plasmid pEC18. *Agrobacterium tumefaciens* LBA4404 cells were subsequently transformed with pEC18 as described in Example 2. The transformed *A. tumefaciens* cells were then used for infection of tobacco (*Nicotiana tabacum* cv. Xanthi) leaf disks using protocols detailed in Example 2.

The resulting tobacco callus transformed with the putative rice HGGT cDNA (rds1c.pk007.m9; SEQ ID NO: 5) operably linked to the cauliflower mosaic virus 35S promoter was maintained and analyzed for tocopherol and tocotrienol content as described in Example 2. Tobacco callus expressing the putative rice HGGT cDNA accumulated molecular species of tocotrienols including α-, β-, γ- and δ-tocotrienol. Of four independent transformation events analyzed, amounts of tocotrienols detected were as high as 95 mg/kg (dry weight). In contrast, no tocotrienol accumulation was detected in tobacco callus transformed with the pZS199 binary vector lacking cDNA insert.

These results thus demonstrate that the rice rds1c.pk007.m9 cDNA disclosed in SEQ ID NO:5 encodes a functional HGGT polypeptide whose expression in transgenic plant cells is sufficient for the production of tocotrienols.

EXAMPLE 5

Production of Tocotrienols in Somatic Soybean Embryos

Somatic soybean embryos have been used as model for the prediction of transgenic phenotypes in soybean seeds (Kinney, A. J. (1996) *J Food Lipids* 3:273-292). Somatic soybean embryos and seeds are enriched in tocopherols, but contain little or no tocotrienols (Coughlan, unpublished result; The Lipid Handbook, 2nd Edition, Gunstone, F. D., et al., Eds., Chapman and Hall, London, 1994, pp.129-131). To demonstrate the ability to produce tocotrienols in somatic soybean embryos, the barley HGGT cDNA (bdl2c.pk006.o2; SEQ ID NO: 1) was expressed in this tissue under control of a strong seed specific promoter. The open-reading frame of bdl2c.pk006.o2 was initially amplified by PCR to generate flanking NotI sites for cloning into the soybean expression vector. The sequences of the sense and antisense oligonucleotide primers used in this reaction were as follows: 5'-tt gcggccgcAGGATGCAAGCCGTCACGGCGGCAGCCG-3' (SEQ ID NO: 52) and 5'-tt gcggccgcTTCACATCTGCTGGCCCTTGTAC-3' (SEQ ID NO: 53). (Note: The lower case, underlined nucleotide sequences correspond to added NotI restriction sites.) PCR amplification was achieved using Pfu polymerase, and an aliquot of the barley developing seed cDNA library described in Example 2 was used as the template. The product of this PCR reaction was purified by agarose gel electrophoresis and subcloned into pCR-Script-AMP (Stratagene) as described in the manufacturer's protocol. The amplified open-reading frame of the barley HGGT was then released as a NotI fragment and cloned into the corresponding site of soybean expression vector pKS121 to generate plasmid pSH13. The construction of vector pKS121 was previously described in WO 02/00904 (the contents of which are hereby incorporated by reference). This vector contains the seed specific promoter for the Kunitz trypsin inhibitor-3 (Kti3) gene (Jofuku and Goldberg (1989) *Plant Cell* 1:1079-1093) linked via a NotI restriction site to the 3' transcriptional termination sequence of the Kti3 gene. Bacterial selection for the pKS121 plasmid is conferred by a hygromycin B phosphotransferase gene (Gritz and Davies (1983) *Gene* 25:179-188) under control of the promoter for the T7 RNA polymerase promoter. Plasmid pSH13 thus contains a soybean expression cassette consisting of the barley HGGT open-reading frame operably linked on its 5' end to the Kti3 promoter and on its 3' end to the Kti3 transcription termination sequence.

Somatic soybean embryos were transformed with pSH13 using the biolistic method. For these experiments, pSH13 was co-bombarded with the plasmid pKS18HH at a 10:1 molar ratio of the two plasmids. Plasmid pKS18HH (U.S. Pat. No. 5,846,784 (the contents of which are hereby incorporated by reference)) contains hygromycin B phosphotransferase gene under control of the cauliflower mosaic 35S promoter, which allows for selection of transformed plant cells by resistance to the antibiotic hygromycin B. The protocol used for transformation of somatic soybean embryos is described below.

To induce somatic embryos, cotyledons, 3-5 mm in length dissected from surface sterilized, immature seeds of a soybean cultivar Jack were cultured in the light or dark at 26° C. on an appropriate agar medium for 6-10 weeks. Somatic embryos that produce secondary embryos were then excised and placed into a suitable liquid medium. After repeated selection for clusters of somatic embryos that multiplied as early, globular staged embryos, the suspensions were maintained as described below.

Soybean embryogenic suspension cultures were maintained in 35 mL liquid media on a rotary shaker, 150 rpm, at 26° C. with florescent lights on a 16:8 hour day/night schedule. Cultures were subcultured every two weeks by inoculating approximately 35 mg of tissue into 35 mL of liquid medium.

Soybean embryogenic suspension cultures were then co-transformed with pSH13 and pKS18HH by the method of particle gun bombardment (Klein et al. (1987) Nature (London) 327:70; U.S. Pat. No. 4,945,050). A DuPont Biolisticá PDS1000/HE instrument (helium retrofit) was used for these transformations.

To 50 mL of a 60 mg/mL 1 mm gold particle suspension were added (in order): 5 mL DNA (1 mg/mL), 20 mL spermidine (0.1 M), and 50 mL $CaCl_2$ (2.5 M). The particle preparation was then agitated for three minutes, spun in a microfuge for ten seconds and the supernatant removed. The DNA-coated particles were then washed once in 400 mL 70% ethanol and resuspended in 40 mL of anhydrous ethanol. The DNA/particle suspension was sonicated three times for one second each. Five mL of the DNA-coated gold particles was then loaded on each macro carrier disk.

Approximately 300-400 mg of a two-week-old suspension culture was placed in an empty 60×15-mm petri dish and the residual liquid removed from the tissue with a pipette. For each transformation experiment, approximately five to ten plates of tissue were bombarded. Membrane rupture pressure was set at 1100 psi and the chamber was evacuated to a vacuum of 28 inches mercury. The tissue was placed approximately 3.5 inches away from the retaining screen and bombarded three times. Following bombardment, the tissue was divided in half and placed back into liquid and cultured as described above.

Five to seven days post bombardment, the liquid media was exchanged with fresh media, and eleven to twelve days post bombardment with fresh media containing 50 mg/mL hygromycin. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each new line was treated as an independent transformation event. These suspensions were then subcultured and maintained as clusters of immature embryos. Immature embryos at this stage produce storage products, including storage lipids that are similar in composition to zygotic embryos at a similar stage of development (see WO 94/11516 (the contents of which are hereby incorporated by reference)).

The resulting somatic embryos transformed with the barley HGGT expression cassette from pSH13 were examined for tocotrienol production using extraction and analytical techniques described in Example 2. In at least three of 19 transgenic events analyzed, the accumulation of α, γ, and δ molecular species of tocotrienol was detected. In contrast, no tocotrienols were detected in untransformed somatic soybean embryos.

These results thus demonstrate the ability to produce tocotrienols in a crop plant that does not normally accumulate these antioxidant molecules through the transgenic expression of a nucleic acid fragment encoding an HGGT polypeptide.

EXAMPLE 6

Production of Tocotrienols in Corn (*Zea mays*) Seed

Corn oil, which is derived primarily from the embryo of corn seeds, is typically enriched in tocopherols but contains little or no tocotrienols (The Lipid Handbook, 2nd Edition, Gunstone, F. D., et al., Eds., Chapman and Hall, London, 1994, pp.129-131). Based on results disclosed in Examples 2 and 5, the barley HGGT cDNA (SEQ ID NO: 1) can be expressed in seed embryo of corn to produce tocotrienols and to increase the tocol antioxidant content of this tissue and the extracted oil. As described below, this can be achieved by transforming corn with the barley HGGT open reading frame operably linked on its 5' end to an embryo specific promoter, such as the promoter for the corn 16 kDa oleosin gene (Lee, K. and Huang, A. H. (1994) *Plant Mol. Biol.* 26:1981-1987).

Initially, the open reading frame of the barley HGGT cDNA (SEQ ID NO: 1) was amplified by PCR to generate flanking PacI restriction sites, which allow for the cDNA to be cloned into a corn embryo expression cassette. The sense and antisense oligonucleotide primers used for PCR amplification were as follows: 5'-atttaattaaGCCGGCGAGGATGCAAGCCGTC-3' (SEQ ID NO: 54) and 5'-ta ttaattaaTTCACATCTGCTGGCCCTTGTAC-3' (SEQ ID NO: 55). (The lower case, underlined nucleotides correspond to the added PacI sites, and the additional lower case nucleotides are added to facilitate restriction enzyme digestion.) Amplification can be achieved using Pfu polymerase (Stratagene) and reaction conditions similar to those described in Example 5. The resulting PCR product derived from the barley HGGT cDNA was purified, digested with PacI, and then cloned into the corresponding site of the corn embryo expression vector pTG10 to generate plasmid pKR242. Vector pTG10 contains a corn expression cassette consisting of 959 base pairs of the promoter for the corn 16 kDa oleosin gene which has been previously described in WO 99/64579 (the contents of which are hereby incorporated by reference). This promoter element is linked via a PacI restriction site to 330 base pairs of the 3' transcription termination sequence of the corn 16 kDa oleosin gene (Lee, K. and Huang, A. H. (1994) *Plant Mol. Biol.* 26:1981-1987). Bacterial selection in pTG10 is conferred by a hygromycin B phosphotransferase gene (Gritz, L. and Davies, J. (1983) *Gene* 25:179-188) under control of the promoter for the T7 RNA polymerase gene. Plasmid pKR242 thus contains an expression cassette composed of the barley HGGT open reading frame operably linked on its 5' end to the promoter for the corn 16 kDa oleosin gene and on its 3' end to the transcription termination sequence of the corn 16 kDa oleosin gene. The entire expression cassette is flanked by AscI restriction sites. Following digestion with AscI, the expression cassette of pKR242 was removed and inserted into the corresponding site of the binary vector PHP15578 to generate plasmid PHP18749. The binary vector PHP15578 has been previously described in WO 02/00904 (the contents of which are hereby incorporated by reference). PHP15578 contains right and left border regions to facilitate *Agrobacterium*-mediated transformation of corn, and plant selection is conferred by a cauliflower mosaic virus 35S promoter-bialaphos selectable marker element.

Plasmid PHP18749 can be used for the generation of transgenic corn that expresses the barley HGGT cDNA in an embryo specific manner. An *Agrobacterium*-based protocol can be used for the transformation of corn with expression elements from PHP18749 as described below.

Transformation of Corn Mediated by *Agrobacterium*:

Freshly isolated immature embryos of corn, about 10 days after pollination (DAP), can be incubated with the Agrobacterium. The preferred genotype for transformation is the highly transformable genotype Hi-II(Armstrong (1991) *Maize Gen. Coop. Newsletter* 65:92-93). An F, hybrid created by crossing a Hi-II with an elite inbred may also be used. After *Agrobacterium* treatment of immature embryos, the embryos can be cultured on medium containing toxic levels of herbicide. Only those cells that receive the herbicide resistance gene, and the linked gene(s), grow on selective medium. Transgenic events so selected can be propagated and regenerated to whole plants, produce seed, and transmit transgenes to progeny.

Preparation of *Agrobacterium*:

The engineered *Agrobacterium tumefaciens* LBA4404 can be constructed to contain plasmid PHP18749, as disclosed in U.S. Pat. No. 5,591,616 (the contents of which are hereby incorporated by reference). To use the engineered construct in plant transformation, a master plate of a single bacterial colony transformed with PHP18749 can be prepared by inoculating the bacteria on minimal AB medium and allowing incubation at 28° C. for approximately three days. (The composition and preparation of minimal AB medium has been previously described in WO 02/00904 (the contents of which are hereby incorporated by reference.) A working plate can then be prepared by streaking the transformed *Agrobacterium* on YP medium (0.5% (w/v) yeast extract,1% (w/v) peptone, 0.5% (w/v) sodium chloride, 1.5% (w/v) agar) that contains 50 µg/mL of spectinomycin.

The PHP18749-transformed Agrobacterium for plant transfection and co-cultivation can then be prepared one day prior to corn transformation. Into 30 mL of minimal A medium (prepared as described in Application WO 02/009040) in a flask was placed 50 µg/mL spectinomycin, 100 µM acetosyringone, and about a 1/8 loopful of *Agrobacterium* from a one to two-day-old working plate. The *Agrobacterium* can then be grown at 28° C. with shaking at 200 rpm for approximately fourteen hours. At mid-log phase, the *Agrobacterium* can be harvested and resuspended at a density of 3 to 5×108 CFU/mL in 561 Q medium that contains 100 µM acetosyringone using standard microbial techniques. The composition and preparation of 561Q medium was described in WO 02/009040.

Immature Embryo Preparation:

Nine to ten days after controlled pollination of a corn plant, developing immature embryos are opaque and 1-1.5 mm long. This length is the optimal size for infection with the PHP18749-transformed Agrobacterium. The husked ears can be sterilized in 50% commercial bleach and one drop Tween-20 for thirty minutes, and then rinsed twice with sterile water. The immature embryos can then be aseptically removed from the caryopsis and placed into 2 mL of sterile holding solution consisting of medium 561 Q that contains 100 µM of acetosyringone.

*Agrobacterium* Infection and Co-cultivation of Embryos:

The holding solution can be decanted from the excised immature embryos and replaced with the PHP18749-transformed *Agrobacterium*. Following gentle mixing and incubation for about five minutes, the *Agrobacterium* can be decanted from the immature embryos. Immature embryos were then moved to a plate of 562P medium, the composition of which has been previously described in WO 02/009040. The immature embryos can be placed on this media scutellum surface pointed upwards and then incubated at 20° C. for three days in darkness. This can be followed by incubation at 28° C. for three days in darkness on medium 562P that contains 100 µg/mL carbenecillin as described in U.S. Pat. No. 5,981,840.

Selection of Transgenic Events:

Following incubation, the immature embryos can be transferred to 5630 medium, which can be prepared as described in WO 02/009040. This medium contains Bialaphos for selection of transgenic plant cells as conferred by the BAR gene that is linked to barley HGGT expression cassette. At ten to fourteen-day intervals, embryos were transferred to 5630 medium. Actively growing putative transgenic embryogenic tissue can be after six to eight weeks of incubation on the 5630 medium.

Regeneration of T₀ Plants:

Transgenic embryogenic tissue is transferred to 288W medium and incubated at 28° C. in darkness until somatic embryos matured, or about ten to eighteen days. Individual matured somatic embryos with well-defined scutellum and coleoptile are transferred to 272 embryo germination medium and incubated at 28° C. in the light. After shoots and roots emerge, individual plants are potted in soil and hardened-off using typical horticultural methods.

288W medium contains the following ingredients: 950 mL of deionized water; 4.3 g of MS Salts (Gibco); 0.1 g of myo-inositol; 5 mL of MS Vitamins Stock Solution (Gibco); 1 mL of zeatin (5 mg/mL solution); 60 g sucrose; 8 g of agar (Sigma A-7049, Purified), 2 mL of indole acetic acid (0.5 mg/mL solution*); 1 mL of 0.1 mM ABA*; 3 mL of Bialaphos (1 mg/mL solution*); and 2 mL of carbenicillin (50 mg/mL solution). The pH of this solution is adjusted to pH 5.6. The solution is autoclaved and ingredients marked with an asterisk (*) are added after the media has cooled to 60° C. Medium 272 contains the following ingredients: 950 mL of deionized water; 4.3 g of MS salts (Gibco); 0.1 g of myo-inositol; 5 mL of MS vitamins stock solution (Gibco); 40 g of Sucrose; and 1.5 g of Gelrite. This solution is adjusted to pH 5.6 and then autoclaved.

Confirmation of Transformation:

Fifty putative transgenic events were recovered and initially confirmed using a leaf paint test with bialaphos herbicide. The subsequent lack of a herbicide-injury lesion indicated the presence and action of the herbicide selectable marker and the plants were self pollinated and taken through seed fill and maturation. More than 150 seeds were obtained from each of 48 of the initially selected, transformed lines. The germ from 10 seeds of each of the 48 lines and one non-transgenic control was partially removed by dissection, weighed and combined in a 1.5 ml micro-centrifuge tube. One ml of heptane, which also contained 80 µg of α-tocopherol acetate as internal standard, was added and the germ material was ground using a small plastic pestle. The ground germ material was further extracted during 2 hrs of agitation at room temperature. Total tocopherols and tocotrienols were analyzed on one aliquot of extract using the HPLC separation and fluorescence detection procedure described in Example 2. The total fatty acid content of the heptane extract was determined by adding 2.5 mg of Tri-heptadecanoylglyceride to a 50 µl aliquot and forming the methyl esters by transesterification in 1 ml of methanol containing 0.25% sodium methoxide. The fatty acid methyl esters were extracted into 1 ml of heptane after addition of 1 ml of 1 M NaCl to the transesterification reaction. Total fatty acids were determined by separation of the methyl esters by GLC, detection by flame ionization and comparison of peak areas to the peak area of the methylheptadecanoate derived from the internal standard. α-, β-, γ- and δ-Tocotrienol was detected in all of the transgenic lines but not in the germ extract of the non-transgenic control. Gamma-tocopherol was the most prominent tocopherol present and γ-tocotrienol was the most prominent tocotrienol in the transgenic events. The total tocopherol content of the transgenic lines on an oil basis was similar to that of the non-transgenic control and the total tocotrienol varied by event but reached levels up to 3 times the endogenous tocopherol content. The results for all the events analyzed are shown in Table 3 and demonstrate that the barley HGGT gene under the control of a promoter that is active in maize embryo tissue is capable of introducing the capability to synthesize and store tocotrienol. The total oil soluble anti-oxidant content can be increased by at least 3-fold by the expressed chimeric gene.

TABLE 3

Total tocopherol per mg of oil and total tocotrienol per mg of oil in the germ of 48 trangenic maize lines expressing the barley HGGT gene under control of the maize oleosin promoter and one wild type control. Individual events are ranked by total tocotrienol content.

| EVENT # | TOTAL TOCOPHEROL (NG/MG OF OIL) | TOTAL TOCOTRIENOL (NG/MG OF OIL) |
|---|---|---|
| A1532.064.7.25.1 | 2997.5 | 8368.5 |
| A1532.064.8.11.1 | 2858.9 | 6274.0 |
| A1532.064.7.14.1 | 2990.3 | 5791.1 |
| A1532.064.8.8.1 | 2720.3 | 5273.8 |
| A1532.064.7.16.1 | 3018.5 | 5188.9 |
| A1532.064.8.16.1 | 2068.4 | 5146.2 |
| A1532.064.7.8.1 | 2701.9 | 5074.8 |
| A1532.064.7.22.1 | 2306.6 | 4601.8 |
| A1532.064.8.17.1 | 1993.4 | 4565.4 |
| A1532.064.7.4.1 | 2996.7 | 4372.7 |
| A1532.064.8.15.1 | 2610.3 | 4336.6 |
| A1532.064.7.19.1 | 3663.3 | 4186.1 |
| A1532.064.7.5.1 | 1946.2 | 4104.0 |
| A1532.064.7.23.1 | 2554.5 | 3914.6 |
| A1532.064.8.20.1 | 2359.2 | 3913.3 |
| A1532.064.8.14.1 | 2680.9 | 3728.6 |
| A1532.064.7.20.1 | 2026.7 | 3681.1 |
| A1532.064.8.24.1 | 2330.7 | 3679.9 |
| A1532.064.7.18.1 | 2017.5 | 3621.9 |
| A1532.064.7.1.1 | 2899.1 | 3477.0 |
| A1532.064.8.22.1 | 2827.6 | 3333.6 |
| A1532.064.7.3.1 | 4293.1 | 3248.2 |
| A1532.064.8.7.1 | 3797.9 | 3093.1 |
| A1532.064.7.15.1 | 2840.9 | 3091.1 |
| A1532.064.8.9.1 | 3425.5 | 2391.8 |
| A1532.064.8.18.1 | 2932.6 | 2391.6 |
| A1532.064.7.7.1 | 2500.9 | 2327.0 |
| A1532.064.8.12.1 | 2673.3 | 2315.3 |
| A1532.064.7.24.1 | 3072.7 | 2089.2 |
| A1532.064.8.13.1 | 2782.0 | 2062.6 |
| A1532.064.7.12.1 | 2140.8 | 1824.4 |
| A1532.064.7.11.1 | 3076.0 | 1805.6 |
| A1532.064.8.3.1 | 1515.9 | 1770.7 |
| A1532.064.7.10.1 | 2928.5 | 1692.5 |
| A1532.064.7.17.1 | 4019.4 | 818.5 |
| A1532.064.7.13.1 | 4047.7 | 775.1 |
| A1532.064.8.2.1 | 2869.2 | 683.7 |
| A1532.064.8.1.1 | 2667.5 | 601.8 |
| A1532.064.8.25.1 | 3068.6 | 481.5 |
| A1532.064.7.21.1 | 3887.7 | 375.8 |
| A1532.064.7.9.1 | 2320.7 | 357.8 |
| A1532.064.8.5.1 | 2797.1 | 81.9 |
| A1532.064.7.2.1 | 1186.8 | 56.0 |
| A1532.064.8.6.1 | 3094.8 | 41.6 |
| WT | 2732.0 | 0 |

Since the transgene in the seed population from a self pollinated initial transformant is expected to be genetically segregating for the presence of the transgene and its copy number, 15 single seeds from events were selected by their bulked, excised-germ, tocotrienol content. Single seeds were ground in a ball-impact single seed grinder and 100 mg of the resulting powder was weighed into 1.5 ml micro-centrifuge tubes and extracted using 1 ml of heptane and 5.4 µg of the α-tocopherol acetate internal standard as describe for the bulk germ. Unlike bulk germ, wild type maize whole seed contains the set of α, β and γ tocotrienols due to their presence in the endosperm tissue. Extracted tocols were separated and quantified using the HPLC method described above and the results expressed as parts per million tocopherol, tocotrienol and the sum of the compound classes is shown in Table 4.

TABLE 4

Total tocopherols, total tocotrienols and the sum of the two expressed parts per million in grain. The results are from 15 single seeds for each of 7 transgenic events chosen to represent a sampling of all events based on their bulk germ analysis. The first entries listed as "B73" followed by a letter are single seeds from a wild type control. Entries within an event are ranked by their total tocotrienol content.

| seed and event number | ppm tocopherol in grain | ppm tocotrienol in grain | ppm total toco in grain |
|---|---|---|---|
| B73L 10/23 | 57.3 | 8.5 | 65.8 |
| B73N 10/23 | 47.4 | 7.5 | 54.9 |
| B73H 10/23 | 88.6 | 7.3 | 95.9 |
| B73M 10/23 | 63.4 | 7.1 | 70.5 |
| B73I 10/23 | 44.4 | 6.7 | 51.1 |
| B73O 10/23 | 52.2 | 6.3 | 58.5 |
| B73B 10/17 | 41.1 | 5.9 | 47.0 |
| B73J 10/23 | 52.5 | 5.6 | 58.1 |
| B73E 10/23 | 49.6 | 5.5 | 55.1 |
| B73F 10/23 | 52.5 | 5.3 | 57.8 |
| B73A 10/17 | 17.2 | 3.5 | 20.7 |
| B73C 10/17 | 30.6 | 3.3 | 33.9 |
| B73D 10/17 | 29.6 | 2.5 | 32.1 |
| B73K 10/23 | 23.3 | 2.1 | 25.4 |
| B73G 10/23 | 33.7 | 1.2 | 34.9 |
| 2I A1532.064.7.2 | 98.6 | 21.5 | 120.1 |
| 2J A1532.064.7.2 | 70.6 | 15.3 | 85.9 |
| 2L A1532.064.7.2 | 27.8 | 14.1 | 41.9 |
| 2H A1532.064.7.2 | 25.4 | 11.4 | 36.8 |
| 2B A1532.064.7.2 | 38.9 | 11.2 | 50.1 |
| 2C A1532.064.7.2 | 37.5 | 10.5 | 48.0 |
| 2M A1532.064.7.2 | 46.0 | 9.9 | 55.9 |
| 2N A1532.064.7.2 | 38.4 | 9.6 | 48.0 |
| 2A A1532.064.7.2 | 29.5 | 9.5 | 39.0 |
| 2K A1532.064.7.2 | 38.8 | 9.0 | 47.8 |
| 2G A1532.064.7.2 | 43.2 | 7.1 | 50.3 |
| 2E A1532.064.7.2 | 23.4 | 6.8 | 30.2 |
| 2O A1532.064.7.2 | 14.7 | 5.8 | 20.5 |
| 2F A1532.064.7.2 | 83.9 | 5.4 | 89.3 |
| 2D A1532.064.7.2 | 49.1 | 4.8 | 53.9 |
| 31G A1532.064.8.6 | 140.3 | 21.3 | 161.6 |
| 31J A1532.064.8.6 | 87.5 | 20.0 | 107.5 |
| 31K A1532.064.8.6 | 58.4 | 18.0 | 76.4 |
| 31A A1532.064.8.6 | 94.8 | 16.3 | 111.1 |
| 31M A1532.064.8.6 | 84.3 | 15.0 | 99.3 |
| 31L A1532.064.8.6 | 63.3 | 13.0 | 76.3 |
| 31I A1532.064.8.6 | 43.3 | 10.4 | 53.7 |
| 31D A1532.064.8.6 | 31.1 | 9.3 | 40.4 |
| 31H A1532.064.8.6 | 30.9 | 8.6 | 39.5 |
| 31F A1532.064.8.6 | 42.4 | 8.0 | 50.4 |
| 31B A1532.064.8.6 | 73.5 | 7.5 | 81.0 |
| 31C A1532.064.8.6 | 61.3 | 6.3 | 67.6 |
| 31E A1532.064.8.6 | 30.7 | 5.9 | 36.6 |
| 15A A1532.064.7.15 | 70.8 | 191.9 | 262.7 |
| 15M A1532.064.7.15 | 58.5 | 155.9 | 214.4 |
| 15N A1532.064.7.15 | 72.2 | 135.1 | 207.3 |
| 15I A1532.064.7.15 | 77.1 | 126.8 | 203.9 |
| 15O A1532.064.7.15 | 78.4 | 120.1 | 198.5 |
| 15J A1532.064.7.15 | 45.7 | 104.6 | 150.3 |
| 15E A1532.064.7.15 | 45.6 | 92.8 | 138.4 |
| 15L A1532.064.7.15 | 40.9 | 89.7 | 130.6 |
| 15F A1532.064.7.15 | 52.5 | 82.9 | 135.4 |
| 15D A1532.064.7.15 | 35.7 | 78.2 | 113.9 |
| 15B A1532.064.7.15 | 37.9 | 69.8 | 107.7 |
| 15K A1532.064.7.15 | 27.6 | 58.5 | 86.1 |
| 15C A1532.064.7.15 | 26.9 | 52.0 | 78.9 |
| 15G A1532.064.7.15 | 30.5 | 10.5 | 41.0 |
| 15H A1532.064.7.15 | 17.7 | 7.3 | 25.0 |
| 25B A1532.064.7.25 | 29.2 | 295.9 | 325.1 |
| 25C A1532.064.7.25 | 54.6 | 258.1 | 312.7 |
| 25H A1532.064.7.25 | 34.5 | 258.0 | 292.5 |
| 25G A1532.064.7.25 | 77.3 | 246.7 | 324.0 |
| 25M A1532.064.7.25 | 52.7 | 235.6 | 288.3 |
| 25K A1532.064.7.25 | 72.9 | 226.2 | 299.1 |
| 25F A1532.064.7.25 | 66.7 | 221.0 | 287.7 |
| 25D A1532.064.7.25 | 40.0 | 196.9 | 236.9 |
| 25L A1532.064.7.25 | 60.0 | 195.9 | 255.9 |
| 25E A1532.064.7.25 | 39.9 | 181.8 | 221.7 |

TABLE 4-continued

Total tocopherols, total tocotrienols and the sum of the two expressed parts per million in grain. The results are from 15 single seeds for each of 7 transgenic events chosen to represent a sampling of all events based on their bulk germ analysis. The first entries listed as "B73" followed by a letter are single seeds from a wild type control. Entries within an event are ranked by their total tocotrienol content.

| seed and event number | ppm tocopherol in grain | ppm tocotrienol in grain | ppm total toco in grain |
|---|---|---|---|
| 25A A1532.064.7.25 | 51.7 | 176.6 | 228.3 |
| 25N A1532.064.7.25 | 61.3 | 133.0 | 194.3 |
| 25I A1532.064.7.25 | 39.7 | 114.5 | 154.2 |
| 25O A1532.064.7.25 | 32.9 | 60.8 | 93.7 |
| 25J A1532.064.7.25 | 109.1 | 13.7 | 122.8 |
| 36F A1532.064.8.11 | 55.0 | 293.3 | 348.3 |
| 36B A1532.064.8.11 | 62.1 | 285.5 | 347.6 |
| 36J A1532.064.8.11 | 91.1 | 249.3 | 340.4 |
| 36K A1532.064.8.11 | 87.5 | 242.1 | 329.6 |
| 36D A1532.064.8.11 | 63.8 | 195.4 | 259.2 |
| 36M A1532.064.8.11 | 60.2 | 185.7 | 245.9 |
| 36C A1532.064.8.11 | 142.9 | 163.9 | 306.8 |
| 36G A1532.064.8.11 | 79.3 | 161.8 | 241.1 |
| 36L A1532.064.8.11 | 138.2 | 152.4 | 290.6 |
| 36I A1532.064.8.11 | 85.7 | 147.0 | 232.7 |
| 36E A1532.064.8.11 | 79.1 | 147.0 | 226.1 |
| 36H A1532.064.8.11 | 75.9 | 143.7 | 219.6 |
| 36N A1532.064.8.11 | 64.0 | 137.2 | 201.2 |
| 36O A1532.064.8.11 | 78.5 | 129.1 | 207.6 |
| 36A A1532.064.8.11 | 110.5 | 128.1 | 238.6 |
| 41C A1532.064.8.16 | 77.1 | 307.0 | 384.1 |
| 41F A1532.064.8.16 | 45.3 | 235.5 | 280.8 |
| 41I A1532.064.8.16 | 127.0 | 228.0 | 355.0 |
| 41D A1532.064.8.16 | 63.2 | 209.0 | 272.2 |
| 41B A1532.064.8.16 | 51.4 | 202.6 | 254.0 |
| 41E A1532.064.8.16 | 122.5 | 195.4 | 317.9 |
| 41O A1532.064.8.16 | 91.4 | 189.6 | 281.0 |
| 41L A1532.064.8.16 | 63.5 | 188.6 | 252.1 |
| 41N A1532.064.8.16 | 57.4 | 188.4 | 245.8 |
| 41H A1532.064.8.16 | 125.0 | 167.5 | 292.5 |
| 41M A1532.064.8.16 | 88.2 | 163.3 | 251.5 |
| 41A A1532.064.8.16 | 64.3 | 147.9 | 212.2 |
| 41J A1532.064.8.16 | 59.2 | 135.8 | 195.0 |
| 41K A1532.064.8.16 | 67.2 | 107.1 | 174.3 |
| 41G A1532.064.8.16 | 120.4 | 102.4 | 222.8 |
| 42J A1532.064.8.17 | 112.5 | 460.7 | 573.2 |
| 42F A1532.064.8.17 | 99.9 | 373.2 | 473.1 |
| 42I A1532.064.8.17 | 24.2 | 213.8 | 238.0 |
| 42O A1532.064.8.17 | 57.2 | 201.3 | 258.5 |
| 42L A1532.064.8.17 | 65.7 | 196.5 | 262.2 |
| 42E A1532.064.8.17 | 27.4 | 193.5 | 220.9 |
| 42A A1532.064.8.17 | 51.6 | 181.1 | 232.7 |
| 42N A1532.064.8.17 | 67.8 | 157.9 | 225.7 |
| 42B A1532.064.8.17 | 26.6 | 157.2 | 183.8 |
| 42D A1532.064.8.17 | 51.2 | 149.5 | 200.7 |
| 42C A1532.064.8.17 | 64.3 | 122.7 | 187.0 |
| 42G A1532.064.8.17 | 26.2 | 109.4 | 135.6 |
| 42K A1532.064.8.17 | 98.8 | 105.6 | 204.4 |
| 42H A1532.064.8.17 | 38.8 | 104.6 | 143.4 |
| 42M A1532.064.8.17 | 54.4 | 19.4 | 73.8 |

The 15 wild type seeds had an average tocopherol content of 45.6 ppm, tocotrienol contents that ranged from 1.2 to 8.5 ppm and an averaged 5.2 ppm. Event number A 15232.064.8.6 which was the lowest ranked transgenic had similar average values of 64.7 and 12.3 ppm for tocopherols and tocotrienols respectively. By contrast, event A 1532.064.8.17 that was the top ranked event by bulk germ tocotrienol in oil had single seed tocotrienol values that ranged from 19.4 ppm to 460.7 ppm. The average tocopherol content in the event remained at 57.8 ppm. The transgene has no apparent effect on the ability of the maize seed to store tocopherols while it greatly increase the content of tocotrienol. In a population of segregating seeds, it is reasonable to expect at least one wild type seed in a sample of 15. If the lowest ranking seed in event A1532.064.8.17 is excluded from the tocotrienol average on that basis the average becomes 194.8 ppm and the total of tocopherol and tocotrienol is 252.8 ppm. Those values are conservative estimates of the maximum phenotype expected from the transgene in this event since the population is still segregating for transgene ploidy. If one assumes that the top 25% of seed by ranking is representative of the homozygous condition (assumes one segregating genetic locus) the average tocotrienol estimate is about 315 ppm. That value combined with the average tocopherol content gives a combined estimate of about 373 ppm.

Average expected values for total tocopherol and total tocotrienol in corn seeds is in the range 40 to 90 ppm (see Weber, E. J. 1987. Lipids of the Kernel. Page 335 in: Corn: Chemistry and Technology. S. A. Watson and P. E. Ramstad, eds. American Association of Cereal Chemists, Inc. St. Paul, Minn.). The expression of the barley HGGT increases the tocotrienol levels from about 10 ppm to between 100 and 400 ppm and the total tocopherol +tocotrienol content to between 120 and 450 ppm.

EXAMPLE 7

Characterization of cDNA Clones Encoding Proteins Similar to *Arabidopsis thaliana* Homogentisate Phytyltransferase (Also Known as Tocopherol Polyprenyltransferase)

BLASTP searches using amino acid sequences deduced from clones listed in Table 3 revealed similarity of these polypeptides encoded by the cDNAs homogentisate phytyltransferase from *Arabidopsis thaliana* (NCBI General Identification (GI) No. 17104828; SEQ ID NO: 13). Shown in Table 5 are the BLASTP results for amino acid sequences deduced from the entire cDNA inserts comprising the indicated clone ("FIS").

TABLE 5

BLAST Results for Sequences Encoding Polypeptides Homologous to HGGT

| Clone | Status | BLAST pLog Score NCBI General Identifier No. 17104828 (SEQ ID NO: 13) |
|---|---|---|
| bdl2c.pk006.o2 | FIS | 94.00 |
| cco1n.pk087.l17:fis | CGS | 85.52 |
| p0058.chpbj67r:fis | FIS | 91.00 |
| rds1c.pk007.m9 | FIS | 90.70 |
| wdk2c.pk012.f2:cgs | CGS | 95.00 |

The nucleotide sequence of clone bdl2c.pk006.o2 is shown in SEQ ID NO: 1. The amino acid sequence deduced from nucleotides 63 through 1286 of SEQ ID NO: 1 is shown in SEQ ID NO: 2. The nucleotide sequence of clone cco1n.pk087.l117:cgs is shown in SEQ ID NO: 7. The amino acid sequence deduced from nucleotides 211 through 1353 of SEQ ID NO: 7 is shown in SEQ ID NO: 8. The nucleotide sequence of clone p0058.chpbj67r:fis is shown in SEQ ID NO: 9. The amino acid sequence deduced from nucleotides 357 through 1441 of SEQ ID NO: 9 is shown in SEQ ID NO: 10. The nucleotide sequence of clone rds1c.pk007.m9 is shown in SEQ ID NO: 5. The amino acid sequence deduced from nucleotides 6 through 1220 of SEQ ID NO: 5 is shown in SEQ ID NO :6. The nucleotide sequence of clone wdk2c.pk012.f2:cgs is shown in SEQ ID NO: 3. The amino acid sequence deduced from nucleotides 53 through 1279 of SEQ ID NO: 3 is shown in SEQ ID NO: 4.

The complete gene sequence (cgs) for clone cco1n.pk087.l17 employed a PCR based amplification of the 5'-end of the transcript. Briefly, two nested primers (SEQ ID Nos: 67 and 68) were used in a RACE protocol (Frohman et al. (1988) *Proc. Natl. Acad. Sci. USA* 85:8998-9002) to generate fragments between a single point in the transcript and the 5' end. Primers oriented in the 5' direction (complementary to nucleotides 598-621 and 570-591 of SEQ ID NO: 7) were designed from the instant sequences, then commercially available RACE systems (BRL) were used to isolate specific 5' cDNA fragments (Ohara et al. (1989) *Proc. Natl. Acad. Sci. USA* 86:5673-5677; Loh et al. (1989) *Science* 243:217-220). Products generated by the RACE procedures can be combined to generate full-length cDNAs (Frohman and Martin (1989) *Techniques* 1:165). SEQ ID No: 7 as listed is a cgs sequence and contains two adenine residues at positions 571 and 572. In contrast, the fis sequence variant of SEQ ID No: 7 contains three adenine residues spanning positions 571 to 573 (positions corresponding to SEQ ID No: 7). Primer SEQ ID No: 67 was designed with three thymine residues in order to hybridize with the three adenine residues in the fis variant of SEQ ID No: 7. The additional adenine residue in the fis variant of SEQ ID No: 7 would cause a frameshift to occur in the corresponding amino acid sequence.

Alignments of the amino acid sequences set forth in SEQ ID Nos: 2, 4, 6, 8 and 10 and the sequence from *Arabidopsis thaliana* (NCBI General Identification (GI) No.17104828; SEQ ID NO: 13) were performed. The data in Table 6 represents a calculation of the percent identity of the amino acid sequences set forth in SEQ ID Nos:2, 4, 6, 8 and 10 and the sequence from Arabidopsis thaliana (NCBI General Identification (GI) No.17104828; SEQ ID NO:13).

TABLE 6

Percent Identity of Amino Acid Sequences Deduced from the Nucleotide Sequences of cDNA Clones Encoding Polypeptides Homologous to HGGT

| Clone | SEQ ID NO: | Percent Identity to NCBI General Identifier No. 17104828 (SEQ ID NO: 13) |
| --- | --- | --- |
| bdl2c.pk006.o2 | 2 | 45.3 |
| wdk2c.pk012.f2:cgs | 4 | 45.5 |
| rds1c.pk007.m9 | 6 | 44.8 |
| cco1n.pk087.l17:cgs | 8 | 42.5 |
| p0058.chpbj67r:fis | 10 | 46.5 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a HGGT.

EXAMPLE 8

Expression of Chimeric Genes in Dicot Cells

A seed-specific expression cassette composed of the promoter and transcription terminator from the gene encoding the beta subunit of the seed storage protein phaseolin from the bean Phaseolus vulgaris (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar Jack, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 9

Expression of Chimeric Genes in Microbial Cells

The cDNAs encoding the instant HGGT polypeptides can be used to produce tocotrienols in microbes such as algal and cyanobacterial cells that contain an operable tocopherol biosynthetic pathway. Expression of cDNAs encoding the instant HGGT polypeptides in these cells are expected to result in the condensation of geranylgeranyl pyrophosphate and homogentisate. The product of the HGGT reaction 2-methyl-6-geranylgeranylbenzoquinol can then be converted to tocotrienols by tocopherol biosynthetic enzymes native to the host microbial cell. Tocotrienols can be produced in microbes by linking the cDNAs encoding the instant HGGT polypeptides with promoter elements that are suitable to direct gene expression in the selected host cell. The resulting chimeric genes can be introduced into the host microbial cell using techniques such as homologous recombination (Williams, J. G. K. (1988) *Methods Enzymol.* 167:766-778; Legarde, D. et al. (2000) *App. Environ. Microbiol.* 66:64-72). Host cells transformed with cDNAs for the instant HGGT polypeptides operably linked to functional promoters can then be analyzed for tocotrienol production using techniques described in Example 2.

EXAMPLE 10

Functional Conversion of a Homogentisate Phytyltransferase(HPT) into a Homogentisate Geranylgeranyl Transferase (HGGT) by Enzyme Engineering Numerous examples exist of the conversion of the substrate specificity of one enzyme class to that of another by replacement of specific amino acid residues (e.g., Yuan, L. et al. (1995) *Proc. Natl. Acad. Sci. USA* 92:10639-10643; Cahoon, E. B. et al. (1997) *Proc. Natl. Acad. Sci. USA* 94:4872-4877; Reznik, G. O. et al. (1998) *Proc. Natl. Acad. Sci. USA* 95:13525-13530). This conversion is typically achieved through comparisons of primary or tertiary structures of enzymes that have similar amino acid sequences but different substrate specificities. From these comparisons, one skilled in the art can recognize amino acid residues that likely contribute to the substrate recognition properties of a given functional class of enzymes. Residues that dictate substrate specificity are often ones that are conserved in members of a given functional class of enzyme but are different in other structurally related but functionally divergent classes (Yuan, L. et al., supra). By replacement of these residues, one can experimentally test whether a given amino acid or group of amino acids contribute to the substrate specificity of an enzyme.

Selected amino acid residues in an enzyme can be replaced through a variety of mutagenesis methods that are well known to those skilled in the art (e.g., Cahoon, E. B. et al., supra). By expressing the gene or cDNA for the mutant enzyme in a host cell, one can readily monitor whether replacement of amino acids has altered substrate specificity of the enzyme. Alteration of substrate specificity can be measured by supplying the mutant enzyme with alternative substrates in an in vivo or in vitro assay. Alternatively, one skilled in the art can measure the accumulation of metabolic products of the mutated enzyme upon expression in a host cell.

As described in the instant invention, homogentisate geranylgeranyl transferases (HGGTs) (SEQ ID NOs: 2, 4, 6, 8 and 10) are members of the UbiA prenyltransferase family. Of the functionally diverse members of this family, HGGTs share the highest degree of amino acid sequence identity with homogentisate phytyltransferases (HPTs) (typically 40 to 50% identity). Despite this degree of structural relatedness, HGGTs and HPTs have divergent substrate specificities. HGGTs catalyze the condensation of homogentisate and geranylgeranyl pyrophosphate, the first committed step in tocotrienol biosynthesis. In contrast, HPTs catalyze the condensation of homogentisate and phytyl pyrophosphate, the first committed step in tocopherol biosynthesis. Sequence alignments between SEQ ID NOs: 2, 4, 6, 8, 10, 13, 14, 15, 16 and the sequence from *Synechocystis* sp. PCC 6803 (NCBI General Identification (GI) No.16330366; SEQ ID NO: 17), the sequence from *Escherichia coli* K12 (4-hydroxybenzoate-octaprenyltransferase) (NCBI General Identification (GI) No.16131866; SEQ ID NO: 18) and the sequence from oat (Avena sativa) (chlorophyll synthase) (NCBI General Identification (GI) No. 7378659; SEQ ID NO: 19) showed amino acid residues that are conserved in all HGGTs but are different in other UbiA prenyltranferase family members including HPTs. Using the sequence of the barley HGGT (SEQ ID NO: 2) as the basis for amino acid numbering, these residues include the following: arginine 72, glutamine 73, cysteine 85, cysteine 118, phenylalanine 124, isoleucine 127, isoleucine 128, glycine 129, threonine 131, proline 137, aspartate 142, phenylalanine 144, threonine 145, cysteine 161, isoleucine 213, methionine 270, glutamine 272, leucine 279, alanine 280, isoleucine 333, threonine 338, threonine 351, glutamine 355, serine 361, glycine 364, leucine 365, glutamate 380, asparagine 381 and phenylalanine 401. It is likely that these residues or some subgroup of these residues define the substrate specificity of HGGTs. As such, these amino acids represent targets for the functional conversion of an HPT-type enzyme into an HGGT. In achieving HGGT activity, one need not alter the HPT or UbiA prenyltransferase sequence to comprise all 29 of these residues at these positions. Rather, altering the target sequence to comprise at least any 5, 7, 9, 11, 13, 15, 17, 19, 21, 23, 24, 25, 26, 27, 28, or 29 of these residues at the positions identified can confer HGGT activity upon the target sequence.

By replacement of the equivalent residues (shown above) in an HPT into those found in HGGTs, an HPT can be converted into an enzyme that displays enhanced substrate specificity for geranylgeranyl pyrophosphate in preference to phytyl pyrophosphate. An HPT engineered in this manner is thus the functional equivalent of a naturally occurring HGGT and can be used to produce tocotrienols and increase the tocol content in transgenic host cells as described for HGGTs in Examples 2, 3, 4, 5, 6, 8 and 9. Thus, the invention described herein contemplates HGGTs obtained from plants, including monocots, and sequences from any source that have been engineered to function in plants, and more specifically, in monocots. The term plant homogentisate geranylgeranyl transferase encompasses homogentisate geranylgeranyl transferase sequences derived from a plant source in addition to HPT or other UbiA prenyltransferase sequences from any source modified to be or to encode a functional homogentisate geranylgeranyl transferase in a plant or plant cell using the methods taught herein. The term monocot homogentisate geranylgeranyl transferase encompasses homogentisate geranylgeranyl transferase sequences derived from a monocot plant source in addition to HPT or other UbiA prenyltransferase sequences from any source modified to be or to encode a functional homogentisate geranylgeranyl transferase in a monocot plant or plant cell using the methods taught herein

EXAMPLE 11

Tocotrienol Production in *Arabidopsis thaliana* by Transgenic Expression of the Barley Homogentisate Geranylgeranyl Transferase The cDNA for barley homogentisate geranylgeranyl transferase (HGGT) (SEQ ID NO: 1) was constitutively expressed in *Arabidopsis thaliana* to further demonstrate the utility of this cDNA for tocotrienol production in transgenic plants. Plasmid pSH24 was used for *Agrobacterium*-mediated transformation of *Arabidopsis*. This plasmid, which was described in Example 2, contains the open reading frame of the barley HGGT operably linked on its 5' end to the cauliflower mosaic virus 35S promoter and on its 3' end to the transcription termination sequence of the nopaline synthase gene. This expression cassette together with a kanamycin resistance gene for transgenic plant selection is contained within right and left border regions of the plasmid. pSH24 was introduced into *Agrobacterium tumefaciens* strain C58C1-pMP90 using a freeze-thaw method of bacterial transformation (Holsters, M. et al. (1978) *Mol. Gen. Genet.* 163(2):181-187). *Arabidopsis thaliana* cv Columbia plants were then transformed with *Agrobacterium* harboring pSH24 using the vacuum infiltration method described by Bechtold, N. et al. ((1993) *C.R. Acad. Sci., Paris* 316:1194-1199). Transformed plants were selected for the ability of seeds from the infiltrated plants to germinate and for the seedlings to subsequently grow on media containing 40 µg/mL of kanamycin.

Leaves from the tplants transformed with the barley HGGT cDNA linked to the cauliflower mosaic virus 35S promoter were extracted and tocotrienol accumulation measured using analytical methods described in Example 2. Leaves were collected from the second whorl of 30-day old plants. Plants were maintained under a 14 h-22° C./10 h-18° C. light/dark cycle with a light intensity of 100 µmol m-2 s-1. In the organic extract from leaves of the transgenic plants, several tocotrienol molecular species were detected including α-, γ-, and δ-tocotrienols. The primary tocol form found in these leaves was γ-tocotrienol. No tocotrienols, in contrast, were detected in untransformed plants, and the major tocol species in leaves of these plants instead was α-tocopherol. In addition, the tocol content of leaves of transformed plants was increased by as much as 10 to 15-fold relative to leaves of untransformed plants.

Leaves of T1 plants were found to accumulate large amounts of tocotrienols, which were absent from leaves of non-transformed plants. The content of Vitamin E antioxidants in leaves of segregating T2 plants from one of the selected lines was examined in detail. Leaves from plants displaying a null phenotype accumulated tocopherols (almost exclusively as a-tocopherol) to amounts of 40 to 60 mg/g dry weight. (Similar levels of tocopherols were detected in non-transformed plants.) In contrast, the total content of tocopherols and tocotrienols in leaves of phenotype-positive plants ranged from 700 to 900 mg/g dry weight. In leaves of these plants, g-tocotrienol accounted for approximately 85% of the total Vitamin E content.

EXAMPLE 12

Identification of Protein Sequences Specific to HGGT Homologs

HGGT polypeptides described in the instant invention are members of the UbiA prenyltransferase family, which includes a number of functionally diverse enzymes such as chlorophyll synthase and 4-hydroxybenzoate octaprenyltransferase. Members of this family are distinguished by the presence of a UbiA consensus motif. Of the known members of this family, HGGTs are most closely related to HPTs. HGGTs described in the instant invention (SEQ ID NOs: 2, 4, 6, 8 and 10) share 40 to 50% identity with previously disclosed HPTs (SEQ ID NOs: 13-16). Using amino acid sequence alignments, one skilled in the art can readily distinguish HGGT polypeptides from HPT polypeptides by the presence of amino acid residues that are uniquely conserved in HGGTs. Such residues include (using SEQ ID NO: 2 as the basis for amino acid numbering): arginine 72, glutamine 73, cysteine 85, cysteine 118, phenylalanine 124, isoleucine 127, isoleucine 128, glycine 129, threonine 131, proline 137, aspartate 142, phenylalanine 144, threonine 145, cysteine 161, isoleucine 213, methionine 270, glutamine 272, leucine 279, alanine 280, isoleucine 333, threonine 338, threonine 351, glutamine 355, glycine 364, leucine 365, asparagine 381 and phenylalanine 401.

Protein motifs can be defined as short regions of conserved amino acid sequences that comprise part of a longer sequence. One skilled in the art can discern several HGGT-specific protein motifs. Using the barley HGGT amino acid sequence as the basis for numbering (SEQ ID 2), HGGT-specific motifs include "FXXIIGXT" which encompasses amino acids 124 through 131 and "(K/R)XXXDXFT" which encompasses amino acids 139 through 145. (Note: "X" indicates that a residue is not conserved in HGGTs or is not uniquely conserved in HGGTs.)

One skilled in the art can use amino acid sequence alignments such as those described above to identify "new" HGGTs that correspond to an isolated polypeptide or are deduced from an isolated nucleic acid fragment. An amino acid sequence of an HGGT polypeptide would be expected to be related to UbiA prenyltransferases and of highest relation to known HPT and HGGT polypeptides. In addition, an HGGT polypeptide would be expected to contain one or more of the protein motifs described above or one or more of the amino acid residues that are uniquely conserved in HGGT sequences disclosed in the instant invention as detailed above. Isolation of nucleic acid fragments encoding HGGTs can be achieved through a variety of techniques including hybridization with nucleic acid fragments encoding portions HGGT-related polypeptides or PCR-based strategies such as those described in the Examples herein. The biological source of the isolated nucleic acid fragments would preferably be a plant, plant tissue, or microbe that is known to produce tocotrienols. An isolated nucleic acid fragment can then be expressed in a tissue or cell, preferably a plant tissue or cell, that does not contain tocotrienol to determine whether it encodes a functional HGGT. Methods of expression in a host tissue or cell can include those described in Examples 2, 3, 4, 5, 6, 8, 9, and 11. Expression of a functional HGGT would be expected to confer the ability to synthesize tocotrienols to the tissue or cell. Accumulation of tocotrienols can be determined using analytical methods described in Example 2.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated polynucleotide selected from the group consisting of:
   a) a nucleotide sequence encoding a polypeptide that alters tocotrienol content, wherein the amino acid sequence of the polypeptide and the amino acid sequence of SEQ ID NO: 4 have at least 95% sequence identity;
   b) a nucleotide sequence that is complementary to the nucleotide sequence of a), wherein the complement and the nucleotide sequence contain the same number of nucleotides and are 100% complementary;
   c) a nucleotide sequence set forth in SEQ ID NO: 3 and
   d) a nucleotide sequence encoding the amino acid sequence set forth in SEQ ID NO: 4.

2. An expression cassette comprising the nucleotide sequence of claim 1, wherein the nucleotide sequence is operably linked to at least one regulatory sequence.

3. The expression cassette of claim 2, wherein the regulatory sequence is a promoter.

4. A plant cell transformed with the expression cassette of claim 2.

5. A transformed plant comprising in its genome at least one stably incorporated polynucleotide of claim 1 operably linked to a promoter that drives expression in a plant cell.

6. The plant of claim 5, wherein the plant is a monocot.

7. The plant of claim 6, wherein the monocot is selected from the group consisting of maize, wheat, rice, sorghum, barley, millet and rye.

8. The plant of claim 5, wherein the plant is a dicot.

9. The plant of claim 8, wherein the dicot is selected from the group consisting of soybean, Brassica sp., alfalfa, safflower, sunflower, cotton, peanut and potato.

10. Transformed seed of the plant of claim 5.

11. The seed of claim 10 wherein the tocotrienols are increased to between 19 and 461 ppm.

12. The seed of claim 10 wherein the tocotrienols are increased to between 100 and 400 ppm.

13. The seed of claim 10 wherein the tocotrienols are increased to between 250 and 350 ppm.

14. A method for altering tocotrienol content as compared to wild-type, in a plant or part thereof, the method comprising transforming the plant with a nucleotide construct comprising a nucleotide sequence of claim 1.

15. The method of claim 14, wherein the tocotrienol is increased.

16. The method of claim 14, wherein the plant is a monocot.

17. The method of claim 14, wherein the plant is a dicot.

18. The method of claim 14, wherein the part is seed or grain.

19. The method of claim 14, wherein the nucleotide construct further comprises an operably linked promoter that drives expression in a plant cell.

20. The method of claim 19, wherein the promoter is selected from the group consisting of seed-preferred, constitutive, chemically regulated, tissue-preferred, and developmentally regulated promoters.

* * * * *

SEQUENCE LISTING

```
<160> NUMBER OF SEQ ID NOS: 68

<210> SEQ ID NO 1
<211> LENGTH: 1457
<212> TYPE: DNA
<213> ORGANISM: Hordeum vulgare
<220> FEATURE:
<221> NAME/KEY: CDS
<222> LOCATION: (63)...(1286)
<220> FEATURE:
<221> NAME/KEY: misc_feature
<222> LOCATION: 1410, 1421
<223> OTHER INFORMATION: n = A,T,C or G

<400> SEQUENCE: 1
ccctcctttt acacagatcc gcgggttaac ttcctcctcc ggaggccgcc cggccggcga      60 gg atg caa gcc gtc acg gcg gcg gcc gcg gcg ggg cag ctg cta aca       107
   Met Gln Ala Val Thr Ala Ala Ala Ala Gly Gln Leu Leu Thr
    1               5                  10                  15 gat acg agg aga ggg ccc aga tgt agg gct cgg ctg gga acg acg aga      155
Asp Thr Arg Arg Gly Pro Arg Cys Arg Ala Arg Leu Gly Thr Thr Arg
                 20                  25                  30 tta tcc tgg aca ggt cga ttt gca gtg gaa gct ttt gca ggc cag tgc      203
Leu Ser Trp Thr Gly Arg Phe Ala Val Glu Ala Phe Ala Gly Gln Cys
             35                  40                  45 caa agt gct act act gta atg cat aaa ttc agt gcc att tct caa gct      251
Gln Ser Ala Thr Thr Val Met His Lys Phe Ser Ala Ile Ser Gln Ala
         50                  55                  60 gct agg cct aga aga aac aca aag aga cag tgc agc gat gat tat cca      299
Ala Arg Pro Arg Arg Asn Thr Lys Arg Gln Cys Ser Asp Asp Tyr Pro
 65                  70                  75 gcc ctc caa gct gga tgc agc gag gtt aat tgg gat caa aac ggt tcc      347
Ala Leu Gln Ala Gly Cys Ser Glu Val Asn Trp Asp Gln Asn Gly Ser
 80                  85                  90                  95 aac gcc aat cgg ctt gag gaa atc agg gga gat gtt ttg aag aaa ttg      395
Asn Ala Asn Arg Leu Glu Glu Ile Arg Gly Asp Val Leu Lys Lys Leu
                100                 105                 110 cgc tct ttc tat gaa ttt tgc agg cca cac aca att ttt ggc act ata      443
Arg Ser Phe Tyr Glu Phe Cys Arg Pro His Thr Ile Phe Gly Thr Ile
            115                 120                 125 ata ggt ata act tca gtg tct ctc ctg cca atg aag agc ata gat gat      491
Ile Gly Ile Thr Ser Val Ser Leu Leu Pro Met Lys Ser Ile Asp Asp
        130                 135                 140 ttt act gtc acg gta cta cga gga tat ctc gag gct ttg act gct gct      539
Phe Thr Val Thr Val Leu Arg Gly Tyr Leu Glu Ala Leu Thr Ala Ala
```

```
                    145                 150                 155
tta tgt atg aac att tat gtg gtc ggg ctg aat cag cta tat gac att        587
Leu Cys Met Asn Ile Tyr Val Val Gly Leu Asn Gln Leu Tyr Asp Ile
160                 165                 170                 175 cag att gac aag atc aac aag cca ggt ctt cca ttg gca tct ggg gaa        635
Gln Ile Asp Lys Ile Asn Lys Pro Gly Leu Pro Leu Ala Ser Gly Glu
                180                 185                 190 ttt tca gta gca act gga gtt ttc tta gta ctc gca ttc ctg atc atg        683
Phe Ser Val Ala Thr Gly Val Phe Leu Val Leu Ala Phe Leu Ile Met
                195                 200                 205 agc ttt agc ata gga ata cgt tcc gga tcg gcg cca ctg atg tgt gct        731
Ser Phe Ser Ile Gly Ile Arg Ser Gly Ser Ala Pro Leu Met Cys Ala
            210                 215                 220 tta att gtc agc ttc ctt ctt gga agt gcg tac tcc att gag gct ccg        779
Leu Ile Val Ser Phe Leu Leu Gly Ser Ala Tyr Ser Ile Glu Ala Pro
        225                 230                 235 ttc ctc cgg tgg aaa cgg cac gcg ctc ctc gct gca tca tgt atc cta        827
Phe Leu Arg Trp Lys Arg His Ala Leu Leu Ala Ala Ser Cys Ile Leu
240                 245                 250                 255 ttt gtg agg gct atc ttg gtc cag ttg gct ttc ttt gca cat atg cag        875
Phe Val Arg Ala Ile Leu Val Gln Leu Ala Phe Phe Ala His Met Gln
                260                 265                 270 caa cat gtt ctg aaa agg cca ttg gca gca acc aaa tcg ctg gtg ttt        923
Gln His Val Leu Lys Arg Pro Leu Ala Ala Thr Lys Ser Leu Val Phe
            275                 280                 285 gca aca ttg ttt atg tgt tgc ttc tct gcc gtc ata gca cta ttc aag        971
Ala Thr Leu Phe Met Cys Cys Phe Ser Ala Val Ile Ala Leu Phe Lys
        290                 295                 300 gat att cca gat gtt gat gga gat cga gac ttt ggt atc caa tcc ttg       1019
Asp Ile Pro Asp Val Asp Gly Asp Arg Asp Phe Gly Ile Gln Ser Leu
305                 310                 315 agt gtg aga ttg ggg cct caa aga gtg tat cag ctc tgc ata agc ata       1067
Ser Val Arg Leu Gly Pro Gln Arg Val Tyr Gln Leu Cys Ile Ser Ile
320                 325                 330                 335 ttg ttg aca gcc tat ggc gct gcc act cta gta gga gct tca tcc aca       1115
Leu Leu Thr Ala Tyr Gly Ala Ala Thr Leu Val Gly Ala Ser Ser Thr
                340                 345                 350 aac cta ttt caa aag atc atc act gtg tct ggt cat ggc ctg ctt gct       1163
Asn Leu Phe Gln Lys Ile Ile Thr Val Ser Gly His Gly Leu Leu Ala
            355                 360                 365 ttg aca ctt tgg cag aga gcg cag cac ttt gag gtt gaa aac caa gcg       1211
Leu Thr Leu Trp Gln Arg Ala Gln His Phe Glu Val Glu Asn Gln Ala
        370                 375                 380 cgt gtc aca tca ttt tac atg ttc att tgg aag cta ttc tat gca gag       1259
Arg Val Thr Ser Phe Tyr Met Phe Ile Trp Lys Leu Phe Tyr Ala Glu
385                 390                 395 tat ttc ctt ata cca ttt gtg cag tga aatttgtaca agggccagca             1306
Tyr Phe Leu Ile Pro Phe Val Gln  *
400                 405 gatgtgaact atatatacat gtaaacaaa ttatattact gatgatactc aatccaatgc      1366
ttggattttg cttgtactgt gctatctgta atttcatgat ctanagaaag agcanatgtt     1426
ggatgtgtaa aaaaaaaaaa aaaaaaaaa a                                     1457

<210> SEQ ID NO 2
<211> LENGTH: 407
<212> TYPE: PRT
<213> ORGANISM: Hordeum vulgare

<400> SEQUENCE: 2
```

```
Met Gln Ala Val Thr Ala Ala Ala Ala Gly Gln Leu Leu Thr Asp
 1               5                   10                  15

Thr Arg Arg Gly Pro Arg Cys Arg Ala Arg Leu Gly Thr Thr Arg Leu
                20                  25                  30

Ser Trp Thr Gly Arg Phe Ala Val Glu Ala Phe Ala Gly Gln Cys Gln
            35                  40                  45

Ser Ala Thr Thr Val Met His Lys Phe Ser Ala Ile Ser Gln Ala Ala
    50                  55                  60

Arg Pro Arg Arg Asn Thr Lys Arg Gln Cys Ser Asp Asp Tyr Pro Ala
65                  70                  75                  80

Leu Gln Ala Gly Cys Ser Glu Val Asn Trp Asp Gln Asn Gly Ser Asn
                85                  90                  95

Ala Asn Arg Leu Glu Glu Ile Arg Gly Asp Val Leu Lys Lys Leu Arg
            100                 105                 110

Ser Phe Tyr Glu Phe Cys Arg Pro His Thr Ile Phe Gly Thr Ile Ile
        115                 120                 125

Gly Ile Thr Ser Val Ser Leu Leu Pro Met Lys Ser Ile Asp Asp Phe
130                 135                 140

Thr Val Thr Val Leu Arg Gly Tyr Leu Glu Ala Leu Thr Ala Ala Leu
145                 150                 155                 160

Cys Met Asn Ile Tyr Val Val Gly Leu Asn Gln Leu Tyr Asp Ile Gln
                165                 170                 175

Ile Asp Lys Ile Asn Lys Pro Gly Leu Pro Leu Ala Ser Gly Glu Phe
            180                 185                 190

Ser Val Ala Thr Gly Val Phe Leu Val Leu Ala Phe Leu Ile Met Ser
    195                 200                 205

Phe Ser Ile Gly Ile Arg Ser Gly Ser Ala Pro Leu Met Cys Ala Leu
210                 215                 220

Ile Val Ser Phe Leu Leu Gly Ser Ala Tyr Ser Ile Glu Ala Pro Phe
225                 230                 235                 240

Leu Arg Trp Lys Arg His Ala Leu Leu Ala Ala Ser Cys Ile Leu Phe
                245                 250                 255

Val Arg Ala Ile Leu Val Gln Leu Ala Phe Phe Ala His Met Gln Gln
            260                 265                 270

His Val Leu Lys Arg Pro Leu Ala Ala Thr Lys Ser Leu Val Phe Ala
        275                 280                 285

Thr Leu Phe Met Cys Cys Phe Ser Ala Val Ile Ala Leu Phe Lys Asp
        290                 295                 300

Ile Pro Asp Val Asp Gly Asp Arg Asp Phe Gly Ile Gln Ser Leu Ser
305                 310                 315                 320

Val Arg Leu Gly Pro Gln Arg Val Tyr Gln Leu Cys Ile Ser Ile Leu
                325                 330                 335

Leu Thr Ala Tyr Gly Ala Ala Thr Leu Val Gly Ala Ser Ser Thr Asn
            340                 345                 350

Leu Phe Gln Lys Ile Ile Thr Val Ser Gly His Gly Leu Leu Ala Leu
        355                 360                 365

Thr Leu Trp Gln Arg Ala Gln His Phe Glu Val Glu Asn Gln Ala Arg
    370                 375                 380

Val Thr Ser Phe Tyr Met Phe Ile Trp Lys Leu Phe Tyr Ala Glu Tyr
385                 390                 395                 400

Phe Leu Ile Pro Phe Val Gln
            405
```

-continued

```
<210> SEQ ID NO 3
<211> LENGTH: 1365
<212> TYPE: DNA
<213> ORGANISM: Triticum aestivum
<220> FEATURE:
<221> NAME/KEY: CDS
<222> LOCATION: (53)...(1279)

<400> SEQUENCE: 3
ctttcacaca gatcccaggc cgcttttctc ctccggtggc cgcccggcga gg atg caa      58
                                                          Met Gln
                                                          1 gcc acc acg gcc gcg gcg gcg gcg cag ctg cta aca gat acg agg aga      106
Ala Thr Thr Ala Ala Ala Ala Ala Gln Leu Leu Thr Asp Thr Arg Arg
      5                  10                  15 ggg ccc aga tgt agt agg gct cgg ctg gga gcg acg aga tta tcc tgg      154
Gly Pro Arg Cys Ser Arg Ala Arg Leu Gly Ala Thr Arg Leu Ser Trp
 20                  25                  30 cca ggt cga ttt gca gtg gaa gct ttt gca ggc cgg tgc caa agc agt      202
Pro Gly Arg Phe Ala Val Glu Ala Phe Ala Gly Arg Cys Gln Ser Ser
 35              40                  45                  50 gct act act gtc acg cat aga ttc agt gcc att tct caa gct aca agc      250
Ala Thr Thr Val Thr His Arg Phe Ser Ala Ile Ser Gln Ala Thr Ser
             55                  60                  65 cct aga aga aag gca agg agg cag tgc agc gat gat cag tca gcc ctc      298
Pro Arg Arg Lys Ala Arg Arg Gln Cys Ser Asp Asp Gln Ser Ala Leu
         70                  75                  80 caa gct gga tgc agc aag gtt aat cgc gat caa cat ggt tac gac gtg      346
Gln Ala Gly Cys Ser Lys Val Asn Arg Asp Gln His Gly Tyr Asp Val
     85                  90                  95 aac tgg ttt gag gaa atc agc caa gaa gtt tcg aag aaa ttg cgc gct      394
Asn Trp Phe Glu Glu Ile Ser Gln Glu Val Ser Lys Lys Leu Arg Ala
100                 105                 110 ttc tac cag ttc tgc aga cca cac aca atc ttt ggc act atc ata ggc      442
Phe Tyr Gln Phe Cys Arg Pro His Thr Ile Phe Gly Thr Ile Ile Gly
115                 120                 125                 130 ata act tca gtg tct ctc ctg cca atg aag agc ata gat gat ttt act      490
Ile Thr Ser Val Ser Leu Leu Pro Met Lys Ser Ile Asp Asp Phe Thr
            135                 140                 145 gca acg gta cta aaa ggg tat ctc gag gct ttg gct gct gct tta tgt      538
Ala Thr Val Leu Lys Gly Tyr Leu Glu Ala Leu Ala Ala Ala Leu Cys
        150                 155                 160 atg aac att tat gtg gta ggg ctg aat cag cta tat gac att cag att      586
Met Asn Ile Tyr Val Val Gly Leu Asn Gln Leu Tyr Asp Ile Gln Ile
    165                 170                 175 gac aag atc aac aag cca ggt ctt cca ttg gca gct ggg gaa ttt tca      634
Asp Lys Ile Asn Lys Pro Gly Leu Pro Leu Ala Ala Gly Glu Phe Ser
180                 185                 190 gta gca act ggg gta ttt tta gta gtc aca ttc ctg atc atg agc ttt      682
Val Ala Thr Gly Val Phe Leu Val Val Thr Phe Leu Ile Met Ser Phe
195                 200                 205                 210 agc atc gga ata cat tcc gga tcg gtg cca ctg atg tat gct tta gtt      730
Ser Ile Gly Ile His Ser Gly Ser Val Pro Leu Met Tyr Ala Leu Val
            215                 220                 225 gtc agc ttc ctt ctt gga agt gca tac tcc att gag gct ccg ttg ctc      778
Val Ser Phe Leu Leu Gly Ser Ala Tyr Ser Ile Glu Ala Pro Leu Leu
        230                 235                 240 cgg tgg aaa cgg cac gca ctc ctc gct gca tcc tgt atc cta ttt gtg      826
Arg Trp Lys Arg His Ala Leu Leu Ala Ala Ser Cys Ile Leu Phe Val
    245                 250                 255
```

| | | | | | | | | | | | | | | | | |
|---|---|---|---|---|---|---|---|---|---|---|---|---|---|---|---|---|
| agg | gct | atc | ttg | gtc | cag | ttg | gct | ttc | ttt | gca | cat | atg | cag | caa | cat | 874 |
| Arg | Ala | Ile | Leu | Val | Gln | Leu | Ala | Phe | Phe | Ala | His | Met | Gln | Gln | His | |
| | 260 | | | | 265 | | | | | 270 | | | | | | |

| | | | | | | | | | | | | | | | | |
|---|---|---|---|---|---|---|---|---|---|---|---|---|---|---|---|---|
| gtt | ctg | aaa | agg | ccc | ttg | gca | gca | aca | aaa | tca | ctg | gtg | ttt | gca | aca | 922 |
| Val | Leu | Lys | Arg | Pro | Leu | Ala | Ala | Thr | Lys | Ser | Leu | Val | Phe | Ala | Thr | |
| 275 | | | | | 280 | | | | | 285 | | | | | 290 | |

| | | | | | | | | | | | | | | | | |
|---|---|---|---|---|---|---|---|---|---|---|---|---|---|---|---|---|
| ttg | ttc | atg | tgt | tgc | ttc | tct | gcc | gtc | ata | gct | cta | ttc | aag | gat | ata | 970 |
| Leu | Phe | Met | Cys | Cys | Phe | Ser | Ala | Val | Ile | Ala | Leu | Phe | Lys | Asp | Ile | |
| | | | | 295 | | | | | 300 | | | | | 305 | | |

| | | | | | | | | | | | | | | | | |
|---|---|---|---|---|---|---|---|---|---|---|---|---|---|---|---|---|
| cct | gat | gtt | gat | gga | gac | cga | gat | ttt | ggc | atc | caa | tcc | ttg | agt | gtg | 1018 |
| Pro | Asp | Val | Asp | Gly | Asp | Arg | Asp | Phe | Gly | Ile | Gln | Ser | Leu | Ser | Val | |
| | | | 310 | | | | | 315 | | | | | 320 | | | |

| | | | | | | | | | | | | | | | | |
|---|---|---|---|---|---|---|---|---|---|---|---|---|---|---|---|---|
| aga | ttg | ggg | cca | caa | aga | gtg | tat | cag | ctc | tgc | ata | agc | ata | ctg | ttg | 1066 |
| Arg | Leu | Gly | Pro | Gln | Arg | Val | Tyr | Gln | Leu | Cys | Ile | Ser | Ile | Leu | Leu | |
| | | 325 | | | | | 330 | | | | | 335 | | | | |

| | | | | | | | | | | | | | | | | |
|---|---|---|---|---|---|---|---|---|---|---|---|---|---|---|---|---|
| aca | gcc | tat | ttg | gct | gcc | act | gta | gta | gga | gct | tca | tcc | aca | cac | cta | 1114 |
| Thr | Ala | Tyr | Leu | Ala | Ala | Thr | Val | Val | Gly | Ala | Ser | Ser | Thr | His | Leu | |
| | 340 | | | | | 345 | | | | | 350 | | | | | |

| | | | | | | | | | | | | | | | | |
|---|---|---|---|---|---|---|---|---|---|---|---|---|---|---|---|---|
| ctt | caa | aag | ata | atc | act | gtg | tct | ggt | cat | ggc | ctg | ctt | gca | cta | aca | 1162 |
| Leu | Gln | Lys | Ile | Ile | Thr | Val | Ser | Gly | His | Gly | Leu | Leu | Ala | Leu | Thr | |
| 355 | | | | | 360 | | | | | 365 | | | | | 370 | |

| | | | | | | | | | | | | | | | | |
|---|---|---|---|---|---|---|---|---|---|---|---|---|---|---|---|---|
| ctt | tgg | cag | aga | gcg | cgg | cac | ctt | gag | gtt | gaa | aat | caa | gcg | cgt | gtc | 1210 |
| Leu | Trp | Gln | Arg | Ala | Arg | His | Leu | Glu | Val | Glu | Asn | Gln | Ala | Arg | Val | |
| | | | | 375 | | | | | 380 | | | | | 385 | | |

| | | | | | | | | | | | | | | | | |
|---|---|---|---|---|---|---|---|---|---|---|---|---|---|---|---|---|
| aca | tca | ttt | tac | atg | ttc | att | tgg | aag | cta | ttc | tat | gca | gag | tat | ttc | 1258 |
| Thr | Ser | Phe | Tyr | Met | Phe | Ile | Trp | Lys | Leu | Phe | Tyr | Ala | Glu | Tyr | Phe | |
| | | | 390 | | | | | 395 | | | | | 400 | | | |

| | | | | | | | | |
|---|---|---|---|---|---|---|---|---|
| ctt | ata | cca | ttt | gtg | cag | tga | aatttgtaca agggccagca gatgtgagct | 1309 |
| Leu | Ile | Pro | Phe | Val | Gln | * | | |
| | | 405 | | | | | | | atatatacat gtaaaacaaa ttatattact gatgataccc tatccaatgc ttggaa    1365

```
<210> SEQ ID NO 4
<211> LENGTH: 408
<212> TYPE: PRT
<213> ORGANISM: Triticum aestivum

<400> SEQUENCE: 4
```

Met Gln Ala Thr Thr Ala Ala Ala Ala Gln Leu Leu Thr Asp Thr
1               5                   10                  15

Arg Arg Gly Pro Arg Cys Ser Arg Ala Arg Leu Gly Ala Thr Arg Leu
            20                  25                  30

Ser Trp Pro Gly Arg Phe Ala Val Glu Ala Phe Ala Gly Arg Cys Gln
        35                  40                  45

Ser Ser Ala Thr Thr Val Thr His Arg Phe Ser Ala Ile Ser Gln Ala
    50                  55                  60

Thr Ser Pro Arg Arg Lys Ala Arg Arg Gln Cys Ser Asp Asp Gln Ser
65                  70                  75                  80

Ala Leu Gln Ala Gly Cys Ser Lys Val Asn Arg Asp Gln His Gly Tyr
                85                  90                  95

Asp Val Asn Trp Phe Glu Glu Ile Ser Gln Glu Val Ser Lys Lys Leu
            100                 105                 110

Arg Ala Phe Tyr Gln Phe Cys Arg Pro His Thr Ile Phe Gly Thr Ile
        115                 120                 125

Ile Gly Ile Thr Ser Val Ser Leu Leu Pro Met Lys Ser Ile Asp Asp
    130                 135                 140

Phe Thr Ala Thr Val Leu Lys Gly Tyr Leu Glu Ala Leu Ala Ala Ala
145                 150                 155                 160

```
Leu Cys Met Asn Ile Tyr Val Val Gly Leu Asn Gln Leu Tyr Asp Ile
            165                 170                 175

Gln Ile Asp Lys Ile Asn Lys Pro Gly Leu Pro Leu Ala Ala Gly Glu
        180                 185                 190

Phe Ser Val Ala Thr Gly Val Phe Leu Val Val Thr Phe Leu Ile Met
    195                 200                 205

Ser Phe Ser Ile Gly Ile His Ser Gly Ser Val Pro Leu Met Tyr Ala
210                 215                 220

Leu Val Val Ser Phe Leu Leu Gly Ser Ala Tyr Ser Ile Glu Ala Pro
225                 230                 235                 240

Leu Leu Arg Trp Lys Arg His Ala Leu Leu Ala Ala Ser Cys Ile Leu
                245                 250                 255

Phe Val Arg Ala Ile Leu Val Gln Leu Ala Phe Phe Ala His Met Gln
            260                 265                 270

Gln His Val Leu Lys Arg Pro Leu Ala Ala Thr Lys Ser Leu Val Phe
        275                 280                 285

Ala Thr Leu Phe Met Cys Cys Phe Ser Ala Val Ile Ala Leu Phe Lys
    290                 295                 300

Asp Ile Pro Asp Val Asp Gly Asp Arg Asp Phe Gly Ile Gln Ser Leu
305                 310                 315                 320

Ser Val Arg Leu Gly Pro Gln Arg Val Tyr Gln Leu Cys Ile Ser Ile
                325                 330                 335

Leu Leu Thr Ala Tyr Leu Ala Ala Thr Val Val Gly Ala Ser Ser Thr
            340                 345                 350

His Leu Leu Gln Lys Ile Ile Thr Val Ser Gly His Gly Leu Leu Ala
        355                 360                 365

Leu Thr Leu Trp Gln Arg Ala Arg His Leu Glu Val Glu Asn Gln Ala
    370                 375                 380

Arg Val Thr Ser Phe Tyr Met Phe Ile Trp Lys Leu Tyr Ala Glu
385                 390                 395                 400

Tyr Phe Leu Ile Pro Phe Val Gln
                405
```

```
<210> SEQ ID NO 5
<211> LENGTH: 1242
<212> TYPE: DNA
<213> ORGANISM: Oryza sativa
<220> FEATURE:
<221> NAME/KEY: CDS
<222> LOCATION: (6)...(1220)

<400> SEQUENCE: 5
```

```
agacg atg caa gcc tca tcg gcg gcg gcg gcg gcg gcg tgc tcg gct atc        50
      Met Gln Ala Ser Ser Ala Ala Ala Ala Ala Ala Cys Ser Ala Ile
      1               5                   10                  15 aag ccg gcg gcg cat cag cac acc gtg caa gtc cag gaa gat aag agg        98
Lys Pro Ala Ala His Gln His Thr Val Gln Val Gln Glu Asp Lys Arg
            20                  25                  30 gga tcg gaa ttc agg gct cgg ttt gga acg agg aaa ctg tcc tgg gga       146
Gly Ser Glu Phe Arg Ala Arg Phe Gly Thr Arg Lys Leu Ser Trp Gly
        35                  40                  45 ggt aaa ttg tcg gtg gaa aat tct gct cta cac cag tgt caa agt ctc       194
Gly Lys Leu Ser Val Glu Asn Ser Ala Leu His Gln Cys Gln Ser Leu
    50                  55                  60 aca aga agc ata agg agg caa aaa aga caa cat tct cca gtc ctc caa       242
Thr Arg Ser Ile Arg Arg Gln Lys Arg Gln His Ser Pro Val Leu Gln
65                  70                  75
```

-continued

| | | |
|---|---|---|
| gtg aga tgc tat gcc att gct ggt gat cag cac gaa tcc atc gcc act<br>Val Arg Cys Tyr Ala Ile Ala Gly Asp Gln His Glu Ser Ile Ala Thr<br>80                        85                          90                        95 | 290 |

```
gtg aga tgc tat gcc att gct ggt gat cag cac gaa tcc atc gcc act        290
Val Arg Cys Tyr Ala Ile Ala Gly Asp Gln His Glu Ser Ile Ala Thr
 80                  85                  90                  95 gag ttt gaa gaa att tgc aaa gaa gtt ccc cag aaa ctg gga gct ttt        338
Glu Phe Glu Glu Ile Cys Lys Glu Val Pro Gln Lys Leu Gly Ala Phe
                100                 105                 110 tat cgg ttt tgc cga ccc cac aca att ttt ggc act ata ata gga atc        386
Tyr Arg Phe Cys Arg Pro His Thr Ile Phe Gly Thr Ile Ile Gly Ile
            115                 120                 125 act tca gtt tct ctc ctg cca atg agg agc cta gat gat ttt act atg        434
Thr Ser Val Ser Leu Leu Pro Met Arg Ser Leu Asp Asp Phe Thr Met
        130                 135                 140 aaa gca tta tgg gga ttt ctt gag gct tta tcc tct tct tta tgt atg        482
Lys Ala Leu Trp Gly Phe Leu Glu Ala Leu Ser Ser Ser Leu Cys Met
    145                 150                 155 aat atc tat gtt gta ggc ctg aat caa cta tat gac atc cag att gat        530
Asn Ile Tyr Val Val Gly Leu Asn Gln Leu Tyr Asp Ile Gln Ile Asp
160                 165                 170                 175 aag gtc aat aag ccc agc ctt ccg ttg gcg tca gga gaa ttt tca gtg        578
Lys Val Asn Lys Pro Ser Leu Pro Leu Ala Ser Gly Glu Phe Ser Val
                180                 185                 190 gca act gga gca gtg tta gta ctc acg tcc ttg atc atg agc att gcc        626
Ala Thr Gly Ala Val Leu Val Leu Thr Ser Leu Ile Met Ser Ile Ala
            195                 200                 205 att gga atc aga tcc aaa tca gct cct ttg tta tgt gct ttg ttt atc        674
Ile Gly Ile Arg Ser Lys Ser Ala Pro Leu Leu Cys Ala Leu Phe Ile
        210                 215                 220 agt ttc ttt ctt gga agt gca tac tct gtt gat gct ccg tta ctc cgg        722
Ser Phe Phe Leu Gly Ser Ala Tyr Ser Val Asp Ala Pro Leu Leu Arg
    225                 230                 235 tgg aaa agg aac gcg ttt ctc gct gca tct tgt ata cta ttt gta aga        770
Trp Lys Arg Asn Ala Phe Leu Ala Ala Ser Cys Ile Leu Phe Val Arg
240                 245                 250                 255 gct gtc tta gtt cag cta gct ttc ttt gca cat atg cag caa cat gtt        818
Ala Val Leu Val Gln Leu Ala Phe Phe Ala His Met Gln Gln His Val
                260                 265                 270 ctg aag agg ccc ttg gca cca aca aag tcg gtg gtt ttc gca aca tta        866
Leu Lys Arg Pro Leu Ala Pro Thr Lys Ser Val Val Phe Ala Thr Leu
            275                 280                 285 ttc atg tgt tgc ttt tct tca gtt ata gct tta ttc aag gat att cca        914
Phe Met Cys Cys Phe Ser Ser Val Ile Ala Leu Phe Lys Asp Ile Pro
        290                 295                 300 gat att gat ggt gac aga cat ttt ggc gtc gaa tcc ctg agc gta cgt        962
Asp Ile Asp Gly Asp Arg His Phe Gly Val Glu Ser Leu Ser Val Arg
    305                 310                 315 ttg ggt cca gaa aga gtg tat tgg ctc tgc ata aac ata cta tta aca       1010
Leu Gly Pro Glu Arg Val Tyr Trp Leu Cys Ile Asn Ile Leu Leu Thr
320                 325                 330                 335 gca tat ggg gct gcc att ttg gct gga gca tca tct aca aat cta tgt       1058
Ala Tyr Gly Ala Ala Ile Leu Ala Gly Ala Ser Ser Thr Asn Leu Cys
                340                 345                 350 caa atg att atc acc gtt ttc ggc cat ggc ctg ctt gcc ttt gca ctt       1106
Gln Met Ile Ile Thr Val Phe Gly His Gly Leu Leu Ala Phe Ala Leu
            355                 360                 365 tgg cag aga gca cag cac tgt gac gtt gaa aac aag gcg tgg atc aca       1154
Trp Gln Arg Ala Gln His Cys Asp Val Glu Asn Lys Ala Trp Ile Thr
        370                 375                 380 tca ttt tac atg ttc att tgg aag ttg ttc tac gct gag tat ttc ctt       1202
Ser Phe Tyr Met Phe Ile Trp Lys Leu Phe Tyr Ala Glu Tyr Phe Leu
```

```
              385              390              395
ata cca ttt gtg cag tga gcactatata cacaagggca ag           1242
Ile Pro Phe Val Gln *
400
```

<210> SEQ ID NO 6
<211> LENGTH: 404
<212> TYPE: PRT
<213> ORGANISM: Oryza sativa

<400> SEQUENCE: 6

```
Met Gln Ala Ser Ser Ala Ala Ala Ala Cys Ser Ala Ile Lys
  1               5                  10                  15

Pro Ala Ala His Gln His Thr Val Gln Val Gln Glu Asp Lys Arg Gly
                 20                  25                  30

Ser Glu Phe Arg Ala Arg Phe Gly Thr Arg Lys Leu Ser Trp Gly Gly
             35                  40                  45

Lys Leu Ser Val Glu Asn Ser Ala Leu His Gln Cys Gln Ser Leu Thr
 50                  55                  60

Arg Ser Ile Arg Arg Gln Lys Arg Gln His Ser Pro Val Leu Gln Val
 65                  70                  75                  80

Arg Cys Tyr Ala Ile Ala Gly Asp Gln His Glu Ser Ile Ala Thr Glu
                 85                  90                  95

Phe Glu Glu Ile Cys Lys Glu Val Pro Gln Lys Leu Gly Ala Phe Tyr
            100                 105                 110

Arg Phe Cys Arg Pro His Thr Ile Phe Gly Thr Ile Gly Ile Thr
            115                 120                 125

Ser Val Ser Leu Leu Pro Met Arg Ser Leu Asp Asp Phe Thr Met Lys
130                 135                 140

Ala Leu Trp Gly Phe Leu Glu Ala Leu Ser Ser Ser Leu Cys Met Asn
145                 150                 155                 160

Ile Tyr Val Val Gly Leu Asn Gln Leu Tyr Asp Ile Gln Ile Asp Lys
                165                 170                 175

Val Asn Lys Pro Ser Leu Pro Leu Ala Ser Gly Glu Phe Ser Val Ala
            180                 185                 190

Thr Gly Ala Val Leu Val Leu Thr Ser Leu Ile Met Ser Ile Ala Ile
            195                 200                 205

Gly Ile Arg Ser Lys Ser Ala Pro Leu Leu Cys Ala Leu Phe Ile Ser
        210                 215                 220

Phe Phe Leu Gly Ser Ala Tyr Ser Val Asp Ala Pro Leu Leu Arg Trp
225                 230                 235                 240

Lys Arg Asn Ala Phe Leu Ala Ala Ser Cys Ile Leu Phe Val Arg Ala
                245                 250                 255

Val Leu Val Gln Leu Ala Phe Phe Ala His Met Gln Gln His Val Leu
            260                 265                 270

Lys Arg Pro Leu Ala Pro Thr Lys Ser Val Val Phe Ala Thr Leu Phe
        275                 280                 285

Met Cys Cys Phe Ser Ser Val Ile Ala Leu Phe Lys Asp Ile Pro Asp
290                 295                 300

Ile Asp Gly Asp Arg His Phe Gly Val Glu Ser Leu Ser Val Arg Leu
305                 310                 315                 320

Gly Pro Glu Arg Val Tyr Trp Leu Cys Ile Asn Ile Leu Leu Thr Ala
                325                 330                 335

Tyr Gly Ala Ala Ile Leu Ala Gly Ala Ser Ser Thr Asn Leu Cys Gln
            340                 345                 350
```

```
Met Ile Ile Thr Val Phe Gly His Gly Leu Leu Ala Phe Ala Leu Trp
        355                 360                 365

Gln Arg Ala Gln His Cys Asp Val Glu Asn Lys Ala Trp Ile Thr Ser
        370                 375                 380

Phe Tyr Met Phe Ile Trp Lys Leu Phe Tyr Ala Glu Tyr Phe Leu Ile
385                 390                 395                 400

Pro Phe Val Gln

<210> SEQ ID NO 7
<211> LENGTH: 1730
<212> TYPE: DNA
<213> ORGANISM: Zea mays
<220> FEATURE:
<221> NAME/KEY: CDS
<222> LOCATION: (211)...(1353)

<400> SEQUENCE: 7
ccttgagccg ttccgctgcc attcgaccac caccgccacg gcggcgccga tgccgactac        60
aaccactcgc agagactacc gcctccagcc ccgccgcttc tcatctccac gcagccgtcc       120
gatggccaag cggctcgccg gtgccgacaa agaggtgctc gtcgaggtgg tgaggttcac       180
gcataagagc ggactgaggg gctgtgacgg cgg ctg gaa gga ttt cct ggc cca       234
                                 Arg Leu Glu Gly Phe Pro Gly Pro
                                  1               5 gaa cga cag gaa gtt tgg cgc gtc ggt gag cga ccc gag gaa gcg ctc       282
Glu Arg Gln Glu Val Trp Arg Val Gly Glu Arg Pro Glu Glu Ala Leu
         10                  15                  20 cag gga cgt gct gtt cgc ctt cct gca gac ctt ccc caa gga ttt cca       330
Gln Gly Arg Ala Val Arg Leu Pro Ala Asp Leu Pro Gln Gly Phe Pro
 25                  30                  35                  40 gaa gaa aca ctt gat gcc act agt ccg acg aga gcc acc gga aga caa       378
Glu Glu Thr Leu Asp Ala Thr Ser Pro Thr Arg Ala Thr Gly Arg Gln
                 45                  50                  55 cgc agg cat tcc tca gtc ccc aaa gtg agc tgc tgg gca gct gct cat       426
Arg Arg His Ser Ser Val Pro Lys Val Ser Cys Trp Ala Ala Ala His
             60                  65                  70 cac caa cac aat tct aac ccc cag cag ttt cag gcg att ggc ata cga       474
His Gln His Asn Ser Asn Pro Gln Gln Phe Gln Ala Ile Gly Ile Arg
         75                  80                  85 atc gca aag acg ctg cat gcc ttc tat cag ttc tgc cga cca cac aca       522
Ile Ala Lys Thr Leu His Ala Phe Tyr Gln Phe Cys Arg Pro His Thr
 90                  95                 100 ata ttt gga acc ata ata ggc att act tcg gtg tct atc ctg cca gtg       570
Ile Phe Gly Thr Ile Ile Gly Ile Thr Ser Val Ser Ile Leu Pro Val
105                 110                 115                 120 aag agc ctg gac gat ttt acg ttg ata gct ata tgg gga ttt ctc gag       618
Lys Ser Leu Asp Asp Phe Thr Leu Ile Ala Ile Trp Gly Phe Leu Glu
                125                 130                 135 gct ttg gcc gcc gca tta tgt atg aac gtt tat gta gta ggg ctg aac       666
Ala Leu Ala Ala Ala Leu Cys Met Asn Val Tyr Val Val Gly Leu Asn
            140                 145                 150 aag gtc aat aag cca acc ctc cca tta tcg ttc gga gag ttt tca atg       714
Lys Val Asn Lys Pro Thr Leu Pro Leu Ser Phe Gly Glu Phe Ser Met
        155                 160                 165 cca act gca gta ttg tta gta gtg gca ttc ttg gtc atg agc att agc       762
Pro Thr Ala Val Leu Leu Val Val Ala Phe Leu Val Met Ser Ile Ser
170                 175                 180 atc gga ata aga tca aag tct gct cca ttg atg tgt gct ttg ctt gtt       810
Ile Gly Ile Arg Ser Lys Ser Ala Pro Leu Met Cys Ala Leu Leu Val
```

```
                185                 190                 195                 200
tgc ttc ctt ctt gga agc gca tac ccc att gac gtc cca tta ctc cgg        858
Cys Phe Leu Leu Gly Ser Ala Tyr Pro Ile Asp Val Pro Leu Leu Arg
                205                 210                 215 tgg aag cga cat gct ttt cta gct gca ttc tgc ata atc ttt gtg agg        906
Trp Lys Arg His Ala Phe Leu Ala Ala Phe Cys Ile Ile Phe Val Arg
                220                 225                 230 cct gta gtg gtc cag tta gct ttc ttt gca cac atg cag caa cat gtt        954
Pro Val Val Val Gln Leu Ala Phe Phe Ala His Met Gln Gln His Val
                235                 240                 245 ctg aag agg ccc ttg gca cct aca agg tcg gtg gtc ttt gca aca tgt       1002
Leu Lys Arg Pro Leu Ala Pro Thr Arg Ser Val Val Phe Ala Thr Cys
                250                 255                 260 ttc atg tgt tgc ttc gct gca gta ata gcg cta ttc aag gat att cct       1050
Phe Met Cys Cys Phe Ala Ala Val Ile Ala Leu Phe Lys Asp Ile Pro
265                 270                 275                 280 gat gtc gat gga gat aga gat ttc ggc att cag tcc atg act gta cga       1098
Asp Val Asp Gly Asp Arg Asp Phe Gly Ile Gln Ser Met Thr Val Arg
                285                 290                 295 tta ggc caa cag aga gtg cat agg ctc tgc att aat att ctc atg aca       1146
Leu Gly Gln Gln Arg Val His Arg Leu Cys Ile Asn Ile Leu Met Thr
                300                 305                 310 gca tac gca gcc gca att ttg gta ggc gcg tca tct acg aac ctg tat       1194
Ala Tyr Ala Ala Ala Ile Leu Val Gly Ala Ser Ser Thr Asn Leu Tyr
                315                 320                 325 cag aag att gtc att gtg tct ggt cat ggc ttg ctt gcc tcc aca ctc       1242
Gln Lys Ile Val Ile Val Ser Gly His Gly Leu Leu Ala Ser Thr Leu
                330                 335                 340 tgg caa aga gca caa caa ttt gac att gag aat aag gat tgt atc aca       1290
Trp Gln Arg Ala Gln Gln Phe Asp Ile Glu Asn Lys Asp Cys Ile Thr
345                 350                 355                 360 caa ttt tat atg ttc att tgg aag tta ttc tac gcc gag tat ttt ctt       1338
Gln Phe Tyr Met Phe Ile Trp Lys Leu Phe Tyr Ala Glu Tyr Phe Leu
                365                 370                 375 ata cca ttt gtg tag taaagaatca tgcgaagaac aacaccctg ctatagacat        1393
Ile Pro Phe Val *
                380 gtgaaggttt attgctaatg ttactctacc ccctgctata gacatgtgaa ggtttattgc     1453 taatgttact ctaccgaatg gtctgaatgt ctatgcgtca tttgaatgta atatgactat     1513 ttgttgtatc agggtaacaa ctggagcaaa tgtaccatgt atattaagca ttaatttaac     1573 tgcatcattt gtaccatgta tattatgact atgtatgaga tattgtctct tattagtact     1633 ggatgtgatg tgtcttatta tgactatgga tgagactttt gtgatgtaat tgatgagact     1693 atggttttaa atattgttat gtgattgtgt gtgagat                              1730

<210> SEQ ID NO 8
<211> LENGTH: 380
<212> TYPE: PRT
<213> ORGANISM: Zea mays

<400> SEQUENCE: 8

Arg Leu Glu Gly Phe Pro Gly Pro Glu Arg Gln Glu Val Trp Arg Val
1               5                   10                  15

Gly Glu Arg Pro Glu Glu Ala Leu Gln Gly Arg Ala Val Arg Leu Pro
                20                  25                  30

Ala Asp Leu Pro Gln Gly Phe Pro Glu Glu Thr Leu Asp Ala Thr Ser
        35                  40                  45
```

```
Pro Thr Arg Ala Thr Gly Arg Gln Arg His Ser Ser Val Pro Lys
        50                  55                  60

Val Ser Cys Trp Ala Ala His His Gln His Asn Ser Asn Pro Gln
65                  70                  75                  80

Gln Phe Gln Ala Ile Gly Ile Arg Ile Ala Lys Thr Leu His Ala Phe
                85                  90                  95

Tyr Gln Phe Cys Arg Pro His Thr Ile Phe Gly Thr Ile Ile Gly Ile
            100                 105                 110

Thr Ser Val Ser Ile Leu Pro Val Lys Ser Leu Asp Asp Phe Thr Leu
            115                 120                 125

Ile Ala Ile Trp Gly Phe Leu Glu Ala Leu Ala Ala Leu Cys Met
        130                 135                 140

Asn Val Tyr Val Val Gly Leu Asn Lys Val Asn Lys Pro Thr Leu Pro
145                 150                 155                 160

Leu Ser Phe Gly Glu Phe Ser Met Pro Thr Ala Val Leu Leu Val Val
                165                 170                 175

Ala Phe Leu Val Met Ser Ile Ser Gly Ile Arg Ser Lys Ser Ala
            180                 185                 190

Pro Leu Met Cys Ala Leu Leu Val Cys Phe Leu Gly Ser Ala Tyr
        195                 200                 205

Pro Ile Asp Val Pro Leu Leu Arg Trp Lys Arg His Ala Phe Leu Ala
210                 215                 220

Ala Phe Cys Ile Ile Phe Val Arg Pro Val Val Val Gln Leu Ala Phe
225                 230                 235                 240

Phe Ala His Met Gln Gln His Val Leu Lys Arg Pro Leu Ala Pro Thr
                245                 250                 255

Arg Ser Val Val Phe Ala Thr Cys Phe Met Cys Cys Phe Ala Ala Val
            260                 265                 270

Ile Ala Leu Phe Lys Asp Ile Pro Asp Val Asp Gly Asp Arg Asp Phe
        275                 280                 285

Gly Ile Gln Ser Met Thr Val Arg Leu Gly Gln Gln Arg Val His Arg
        290                 295                 300

Leu Cys Ile Asn Ile Leu Met Thr Ala Tyr Ala Ala Ile Leu Val
305                 310                 315                 320

Gly Ala Ser Ser Thr Asn Leu Tyr Gln Lys Ile Val Ile Val Ser Gly
                325                 330                 335

His Gly Leu Leu Ala Ser Thr Leu Trp Gln Arg Ala Gln Gln Phe Asp
            340                 345                 350

Ile Glu Asn Lys Asp Cys Ile Thr Gln Phe Tyr Met Phe Ile Trp Lys
        355                 360                 365

Leu Phe Tyr Ala Glu Tyr Phe Leu Ile Pro Phe Val
        370                 375                 380

<210> SEQ ID NO 9
<211> LENGTH: 1769
<212> TYPE: DNA
<213> ORGANISM: Zea mays
<220> FEATURE:
<221> NAME/KEY: CDS
<222> LOCATION: (356)...(1441)
<220> FEATURE:
<221> NAME/KEY: misc_feature
<222> LOCATION: 1206, 1207
<223> OTHER INFORMATION: n = A,T,C or G

<400> SEQUENCE: 9
ccacgcgtcc gcgaccacca ccaccacggt gccgccgacg ccgaccacaa ccactcgtag    60
```

-continued

| | |
|---|---|
| agactaccgt ctccgccccc gctgcttctc gtctccacgc agccgtccga tggccaagcg | 120 |
| gctcgccggc gccaacaaag aggtagggga cggcatgcca acaaagcagc ccacccggac | 180 |
| tcggcaggcc gcctcgtttc gctaacccat ttgatctgcg ccgggtgctc gtcgaggtgg | 240 |
| tgaggttcac gcagaagagc ggactgaggg gctgtgacgg tggctggaag gatttcctgg | 300 |
| cccggaacga caggaagttt ggagcgtcgg tgagcgacca gaggaagcgc tctag gga | 358 |

```
                                                                Gly
                                                                  1
cgt gtt gtt cgc ctt cct aca gac ctt ccc caa gga ttt cca gaa gaa      406
Arg Val Val Arg Leu Pro Thr Asp Leu Pro Gln Gly Phe Pro Glu Glu
          5                   10                  15 aca ctt gat gcc act agt ccg acg aga gcc act gga agg caa cac agg      454
Thr Leu Asp Ala Thr Ser Pro Thr Arg Ala Thr Gly Arg Gln His Arg
     20                  25                  30 cat tcc tca gtc ccc aaa gtg agc tgc tgg gca gct gct cat cac caa      502
His Ser Ser Val Pro Lys Val Ser Cys Trp Ala Ala Ala His His Gln
 35                  40                  45 cac aat tct aac ccc cag cag ttt cag gcg att ggc ata cga atc gca      550
His Asn Ser Asn Pro Gln Gln Phe Gln Ala Ile Gly Ile Arg Ile Ala
 50                  55                  60                  65 aag acg ctg cat gcc ttt tat cag ttc tgc cga cca cac aca ata ttt      598
Lys Thr Leu His Ala Phe Tyr Gln Phe Cys Arg Pro His Thr Ile Phe
             70                  75                  80 gga acc ata ata ggc att act tcg gtg tct ctc ctg cca gtg aag agc      646
Gly Thr Ile Ile Gly Ile Thr Ser Val Ser Leu Leu Pro Val Lys Ser
         85                  90                  95 ctg gac gat ttt acg ttg ata gct ata tgg gga ttt ctc gag gct ttg      694
Leu Asp Asp Phe Thr Leu Ile Ala Ile Trp Gly Phe Leu Glu Ala Leu
        100                 105                 110 gcc gcc gca tta tgt atg aac gtt tat gta gta ggg ctg aac cag cta      742
Ala Ala Ala Leu Cys Met Asn Val Tyr Val Val Gly Leu Asn Gln Leu
    115                 120                 125 ttt gac att gag att gac aag gtc aat aag cca acc ctc cca tta gcg      790
Phe Asp Ile Glu Ile Asp Lys Val Asn Lys Pro Thr Leu Pro Leu Ala
130                 135                 140                 145 tcc gga gag ttt tca gtg cca act gca gta ttg tta gta gtg gca ttc      838
Ser Gly Glu Phe Ser Val Pro Thr Ala Val Leu Leu Val Val Ala Phe
                150                 155                 160 ttg gtc atg agc att agc atc gga ata aga tca aag tgt gcg cca ttg      886
Leu Val Met Ser Ile Ser Ile Gly Ile Arg Ser Lys Cys Ala Pro Leu
            165                 170                 175 atg tgt gct ttg ctt gtt agc ttc ctt ctt gga agc gca tac tcc att      934
Met Cys Ala Leu Leu Val Ser Phe Leu Leu Gly Ser Ala Tyr Ser Ile
        180                 185                 190 gac gtt cca tta ctc cga tgg aag cga cat gct ttt cta gct gca ttc      982
Asp Val Pro Leu Leu Arg Trp Lys Arg His Ala Phe Leu Ala Ala Phe
    195                 200                 205 tgc ata atc ttt gtg agg gct gta gtg gtc cgg tta gct ttc ttt gca      1030
Cys Ile Ile Phe Val Arg Ala Val Val Val Arg Leu Ala Phe Phe Ala
210                 215                 220                 225 cac atg cag caa cat gtt ctg aag agg ccc ttg gca cct aca agg tcg      1078
His Met Gln Gln His Val Leu Lys Arg Pro Leu Ala Pro Thr Arg Ser
                230                 235                 240 gtg gtc ttt gca aca tgt ttc atg tgt tgc ttc gct gca gta ata gcg      1126
Val Val Phe Ala Thr Cys Phe Met Cys Cys Phe Ala Ala Val Ile Ala
            245                 250                 255 cta ttc aag gat att cct gat gtc gat gga gat aga gat ttc ggc att      1174
Leu Phe Lys Asp Ile Pro Asp Val Asp Gly Asp Arg Asp Phe Gly Ile
```

-continued

```
                  260                 265                 270
cag tcc atg act gta cga tta ggc caa cag ann gag ctc tgc att aat    1222
Gln Ser Met Thr Val Arg Leu Gly Gln Gln Xaa Glu Leu Cys Ile Asn
    275                 280                 285 att ctc atg aca gca tac gca gtc aca att ttg gta gga gcg ttg tct    1270
Ile Leu Met Thr Ala Tyr Ala Val Thr Ile Leu Val Gly Ala Leu Ser
290                 295                 300                 305 acg aac ctg tat cag aag att gtc att gtg tct ggt cat ggc ttg ctt    1318
Thr Asn Leu Tyr Gln Lys Ile Val Ile Val Ser Gly His Gly Leu Leu
            310                 315                 320 gcc tcc aca ctc tgg caa aga gca caa caa ttt gac att gag aat aag    1366
Ala Ser Thr Leu Trp Gln Arg Ala Gln Gln Phe Asp Ile Glu Asn Lys
        325                 330                 335 gat tgt atc aca caa ttt tat atg ttc att tgg aag tta ttc tat gcc    1414
Asp Cys Ile Thr Gln Phe Tyr Met Phe Ile Trp Lys Leu Phe Tyr Ala
    340                 345                 350 gag tat ttt ctt ata cca ttt gtg tag taaagaatca tgcgaagaac          1461
Glu Tyr Phe Leu Ile Pro Phe Val *
355                 360 atcacccttg ctatagacat gtgaaggttc attgctaatg ttactctacc gaatggtctg   1521
aatgtctatg cgtcatttgt atgtaatatg actttgttgt atcagggtaa caactggagc   1581
aaatgtacca tgtatattaa gcattaattt agctgtgtca tttgtaccat gtatattatg   1641
actatgtatg agatattgtc tcttattagt actagatgtg atgtgtctta ttatgactat   1701
ggatgaaact tttgtgatgt aattgatgag actatggatt taaatattgt taaaaaaaaa   1761
aaaaaaaa                                                            1769

<210> SEQ ID NO 10
<211> LENGTH: 361
<212> TYPE: PRT
<213> ORGANISM: Zea mays
<220> FEATURE:
<221> NAME/KEY: VARIANT
<222> LOCATION: 284
<223> OTHER INFORMATION: Xaa = Any Amino Acid

<400> SEQUENCE: 10

Gly Arg Val Val Arg Leu Pro Thr Asp Leu Pro Gln Gly Phe Pro Glu
1               5                   10                  15

Glu Thr Leu Asp Ala Thr Ser Pro Thr Arg Ala Thr Gly Arg Gln His
            20                  25                  30

Arg His Ser Ser Val Pro Lys Val Ser Cys Trp Ala Ala Ala His His
        35                  40                  45

Gln His Asn Ser Asn Pro Gln Gln Phe Gln Ala Ile Gly Ile Arg Ile
    50                  55                  60

Ala Lys Thr Leu His Ala Phe Tyr Gln Phe Cys Arg Pro His Thr Ile
65                  70                  75                  80

Phe Gly Thr Ile Ile Gly Ile Thr Ser Val Ser Leu Leu Pro Val Lys
                85                  90                  95

Ser Leu Asp Asp Phe Thr Leu Ile Ala Ile Trp Gly Phe Leu Glu Ala
            100                 105                 110

Leu Ala Ala Leu Cys Met Asn Val Tyr Val Gly Leu Asn Gln
        115                 120                 125

Leu Phe Asp Ile Glu Ile Asp Lys Val Asn Lys Pro Thr Leu Pro Leu
    130                 135                 140

Ala Ser Gly Glu Phe Ser Val Pro Thr Ala Val Leu Leu Val Val Ala
145                 150                 155                 160
```

Phe Leu Val Met Ser Ile Ser Ile Gly Ile Arg Ser Lys Cys Ala Pro
            165                 170                 175

Leu Met Cys Ala Leu Leu Val Ser Phe Leu Leu Gly Ser Ala Tyr Ser
            180                 185                 190

Ile Asp Val Pro Leu Leu Arg Trp Lys Arg His Ala Phe Leu Ala Ala
            195                 200                 205

Phe Cys Ile Ile Phe Val Arg Ala Val Val Arg Leu Ala Phe Phe
            210                 215                 220

Ala His Met Gln Gln His Val Leu Lys Arg Pro Leu Ala Pro Thr Arg
225                 230                 235                 240

Ser Val Val Phe Ala Thr Cys Phe Met Cys Cys Phe Ala Ala Val Ile
                245                 250                 255

Ala Leu Phe Lys Asp Ile Pro Asp Val Asp Gly Asp Arg Asp Phe Gly
                260                 265                 270

Ile Gln Ser Met Thr Val Arg Leu Gly Gln Gln Xaa Glu Leu Cys Ile
            275                 280                 285

Asn Ile Leu Met Thr Ala Tyr Ala Val Thr Ile Leu Val Gly Ala Leu
        290                 295                 300

Ser Thr Asn Leu Tyr Gln Lys Ile Val Ile Val Ser Gly His Gly Leu
305                 310                 315                 320

Leu Ala Ser Thr Leu Trp Gln Arg Ala Gln Phe Asp Ile Glu Asn
                325                 330                 335

Lys Asp Cys Ile Thr Gln Phe Tyr Met Phe Ile Trp Lys Leu Phe Tyr
                340                 345                 350

Ala Glu Tyr Phe Leu Ile Pro Phe Val
            355                 360

<210> SEQ ID NO 11
<211> LENGTH: 702
<212> TYPE: DNA
<213> ORGANISM: Hordeum vulgare
<220> FEATURE:
<221> NAME/KEY: CDS
<222> LOCATION: (1)...(702)

<400> SEQUENCE: 11 tac ctt gtt ggg ttg aat cag cta tat gac att cag att gac aag atc      48
Tyr Leu Val Gly Leu Asn Gln Leu Tyr Asp Ile Gln Ile Asp Lys Ile
1               5                   10                  15 aac aag cca ggt ctt cca ttg gca tct ggg gaa ttt tca gta gca act      96
Asn Lys Pro Gly Leu Pro Leu Ala Ser Gly Glu Phe Ser Val Ala Thr
            20                  25                  30 gga gtt ttc tta gta ctc gca ttc ctg atc atg agc ttt agc ata gga     144
Gly Val Phe Leu Val Leu Ala Phe Leu Ile Met Ser Phe Ser Ile Gly
        35                  40                  45 ata cgt tcc gga tcg gcg cca ctg atg tgt gct tta att gtc agc ttc     192
Ile Arg Ser Gly Ser Ala Pro Leu Met Cys Ala Leu Ile Val Ser Phe
    50                  55                  60 ctt ctt gga agt gcg tac tcc att gag gct ccg ttc ctc cgg tgg aaa     240
Leu Leu Gly Ser Ala Tyr Ser Ile Glu Ala Pro Phe Leu Arg Trp Lys
65                  70                  75                  80 cgg cac gcg ctc ctc gct gca tca tgt atc cta ttt gtg agg gct atc     288
Arg His Ala Leu Leu Ala Ala Ser Cys Ile Leu Phe Val Arg Ala Ile
                85                  90                  95 ttg gtc cag ttg gct ttc ttt gca cat atg cag caa cat gtt ctg aaa     336
Leu Val Gln Leu Ala Phe Phe Ala His Met Gln Gln His Val Leu Lys
            100                 105                 110

```
agg cca ttg gca gca acc aaa tcg ctg gtg ttt gca aca ttg ttt atg    384
Arg Pro Leu Ala Ala Thr Lys Ser Leu Val Phe Ala Thr Leu Phe Met
        115                 120                 125 tgt tgc ttc tct gcc gtc ata gca cta ttc aag gat att cca gat gtt    432
Cys Cys Phe Ser Ala Val Ile Ala Leu Phe Lys Asp Ile Pro Asp Val
130                 135                 140 gat gga gat cga gac ttt ggt atc caa tcc ttg agt gtg aga ttg ggg    480
Asp Gly Asp Arg Asp Phe Gly Ile Gln Ser Leu Ser Val Arg Leu Gly
145                 150                 155                 160 cct caa aga gtg tat cag ctc tgc ata agc ata ttg ttg aca gcc tat    528
Pro Gln Arg Val Tyr Gln Leu Cys Ile Ser Ile Leu Leu Thr Ala Tyr
                165                 170                 175 ggc gct gcc act cta gta gga gct tca tcc aca aac cta ttt caa aag    576
Gly Ala Ala Thr Leu Val Gly Ala Ser Ser Thr Asn Leu Phe Gln Lys
            180                 185                 190 atc atc act gtg tct ggt cat ggc ctg ctt gct ttg aca ctt tgg cag    624
Ile Ile Thr Val Ser Gly His Gly Leu Leu Ala Leu Thr Leu Trp Gln
        195                 200                 205 aga gcg cag cac ttt gag gtt gaa aac caa gcg cgt gtc aca tca ttt    672
Arg Ala Gln His Phe Glu Val Glu Asn Gln Ala Arg Val Thr Ser Phe
    210                 215                 220 tac atg ttc atc tgg aac ttg ttt tac gcg                            702
Tyr Met Phe Ile Trp Asn Leu Phe Tyr Ala
225                 230

<210> SEQ ID NO 12
<211> LENGTH: 234
<212> TYPE: PRT
<213> ORGANISM: Hordeum vulgare

<400> SEQUENCE: 12

Tyr Leu Val Gly Leu Asn Gln Leu Tyr Asp Ile Gln Ile Asp Lys Ile
1               5                   10                  15

Asn Lys Pro Gly Leu Pro Leu Ala Ser Gly Glu Phe Ser Val Ala Thr
            20                  25                  30

Gly Val Phe Leu Val Leu Ala Phe Leu Ile Met Ser Phe Ser Ile Gly
        35                  40                  45

Ile Arg Ser Gly Ser Ala Pro Leu Met Cys Ala Leu Ile Val Ser Phe
    50                  55                  60

Leu Leu Gly Ser Ala Tyr Ser Ile Glu Ala Pro Phe Leu Arg Trp Lys
65                  70                  75                  80

Arg His Ala Leu Leu Ala Ser Cys Ile Leu Phe Val Arg Ala Ile
                85                  90                  95

Leu Val Gln Leu Ala Phe Phe Ala His Met Gln Gln His Val Leu Lys
            100                 105                 110

Arg Pro Leu Ala Ala Thr Lys Ser Leu Val Phe Ala Thr Leu Phe Met
        115                 120                 125

Cys Cys Phe Ser Ala Val Ile Ala Leu Phe Lys Asp Ile Pro Asp Val
130                 135                 140

Asp Gly Asp Arg Asp Phe Gly Ile Gln Ser Leu Ser Val Arg Leu Gly
145                 150                 155                 160

Pro Gln Arg Val Tyr Gln Leu Cys Ile Ser Ile Leu Leu Thr Ala Tyr
                165                 170                 175

Gly Ala Ala Thr Leu Val Gly Ala Ser Ser Thr Asn Leu Phe Gln Lys
            180                 185                 190

Ile Ile Thr Val Ser Gly His Gly Leu Leu Ala Leu Thr Leu Trp Gln
        195                 200                 205
```

```
Arg Ala Gln His Phe Glu Val Glu Asn Gln Ala Arg Val Thr Ser Phe
        210                 215                 220

Tyr Met Phe Ile Trp Asn Leu Phe Tyr Ala
225                 230

<210> SEQ ID NO 13
<211> LENGTH: 393
<212> TYPE: PRT
<213> ORGANISM: Arabidopsis thaliana

<400> SEQUENCE: 13

Met Glu Ser Leu Leu Ser Ser Ser Leu Val Ser Ala Ala Gly Gly
  1               5                  10                  15

Phe Cys Trp Lys Lys Gln Asn Leu Lys Leu His Ser Leu Ser Glu Ile
                20                  25                  30

Arg Val Leu Arg Cys Asp Ser Ser Lys Val Val Ala Lys Pro Lys Phe
            35                  40                  45

Arg Asn Asn Leu Val Arg Pro Asp Gly Gln Gly Ser Ser Leu Leu Leu
 50                  55                  60

Tyr Pro Lys His Lys Ser Arg Phe Arg Val Asn Ala Thr Ala Gly Gln
65                  70                  75                  80

Pro Glu Ala Phe Asp Ser Asn Ser Lys Gln Lys Ser Phe Arg Asp Ser
                85                  90                  95

Leu Asp Ala Phe Tyr Arg Phe Ser Arg Pro His Thr Val Ile Gly Thr
            100                 105                 110

Val Leu Ser Ile Leu Ser Val Ser Phe Leu Ala Val Glu Lys Val Ser
        115                 120                 125

Asp Ile Ser Pro Leu Leu Phe Thr Gly Ile Leu Glu Ala Val Val Ala
130                 135                 140

Ala Leu Met Met Asn Ile Tyr Ile Val Gly Leu Asn Gln Leu Ser Asp
145                 150                 155                 160

Val Glu Ile Asp Lys Val Asn Lys Pro Tyr Leu Pro Leu Ala Ser Gly
                165                 170                 175

Glu Tyr Ser Val Asn Thr Gly Ile Ala Ile Val Ala Ser Phe Ser Ile
            180                 185                 190

Met Ser Phe Trp Leu Gly Trp Ile Val Gly Ser Trp Pro Leu Phe Trp
        195                 200                 205

Ala Leu Phe Val Ser Phe Met Leu Gly Thr Ala Tyr Ser Ile Asn Leu
210                 215                 220

Pro Leu Leu Arg Trp Lys Arg Phe Ala Leu Val Ala Ala Met Cys Ile
225                 230                 235                 240

Leu Ala Val Arg Ala Ile Ile Val Gln Ile Ala Phe Tyr Leu His Ile
                245                 250                 255

Gln Thr His Val Phe Gly Arg Pro Ile Leu Phe Thr Arg Pro Leu Ile
            260                 265                 270

Phe Ala Thr Ala Phe Met Ser Phe Ser Val Val Ile Ala Leu Phe
        275                 280                 285

Lys Asp Ile Pro Asp Ile Glu Gly Asp Lys Ile Phe Gly Ile Arg Ser
290                 295                 300

Phe Ser Val Thr Leu Gly Gln Lys Arg Val Phe Trp Thr Cys Val Thr
305                 310                 315                 320

Leu Leu Gln Met Ala Tyr Ala Val Ala Ile Leu Val Gly Ala Thr Ser
                325                 330                 335

Pro Phe Ile Trp Ser Lys Val Ile Ser Val Val Gly His Val Ile Leu
            340                 345                 350
```

```
Ala Thr Thr Leu Trp Ala Arg Ala Lys Ser Val Asp Leu Ser Ser Lys
            355                 360                 365

Thr Glu Ile Thr Ser Cys Tyr Met Phe Ile Trp Lys Leu Phe Tyr Ala
    370                 375                 380

Glu Tyr Leu Leu Leu Pro Phe Leu Lys
385                 390

<210> SEQ ID NO 14
<211> LENGTH: 395
<212> TYPE: PRT
<213> ORGANISM: Glycine max

<400> SEQUENCE: 14

Met Asp Ser Met Leu Leu Arg Ser Phe Pro Asn Ile Asn Asn Ala Ser
 1               5                  10                  15

Ser Leu Ala Thr Thr Gly Ser Tyr Leu Pro Asn Ala Ser Trp His Asn
            20                  25                  30

Arg Lys Ile Gln Lys Glu Tyr Asn Phe Leu Arg Phe Arg Trp Pro Ser
        35                  40                  45

Leu Asn His His Tyr Lys Ser Ile Glu Gly Gly Cys Thr Cys Lys Lys
    50                  55                  60

Cys Asn Ile Lys Phe Val Val Lys Ala Thr Ser Glu Lys Ser Phe Glu
65                  70                  75                  80

Ser Glu Pro Gln Ala Phe Asp Pro Lys Ser Ile Leu Asp Ser Val Lys
                85                  90                  95

Asn Ser Leu Asp Ala Phe Tyr Arg Phe Ser Arg Pro His Thr Val Ile
            100                 105                 110

Gly Thr Ala Leu Ser Ile Ser Val Ser Leu Leu Ala Val Glu Lys
        115                 120                 125

Ile Ser Asp Ile Ser Pro Leu Phe Phe Thr Gly Val Leu Glu Ala Val
    130                 135                 140

Val Ala Ala Leu Phe Met Asn Ile Tyr Ile Val Gly Leu Asn Gln Leu
145                 150                 155                 160

Ser Asp Val Glu Ile Asp Lys Ile Asn Lys Pro Tyr Leu Pro Leu Ala
                165                 170                 175

Ser Gly Glu Tyr Ser Phe Glu Thr Gly Val Thr Ile Val Ala Ser Phe
            180                 185                 190

Ser Ile Leu Ser Phe Trp Leu Gly Trp Val Val Gly Ser Trp Pro Leu
        195                 200                 205

Phe Trp Ala Leu Phe Val Ser Phe Val Leu Gly Thr Ala Tyr Ser Ile
    210                 215                 220

Asn Val Pro Leu Leu Arg Trp Lys Arg Phe Ala Val Leu Ala Ala Met
225                 230                 235                 240

Cys Ile Leu Ala Val Arg Ala Val Ile Val Gln Leu Ala Phe Phe Leu
                245                 250                 255

His Ile Gln Thr His Val Tyr Lys Arg Pro Pro Val Phe Ser Arg Ser
            260                 265                 270

Leu Ile Phe Ala Thr Ala Phe Met Ser Phe Ser Val Val Ile Ala
        275                 280                 285

Leu Phe Lys Asp Ile Pro Asp Ile Glu Gly Asp Lys Val Phe Gly Ile
    290                 295                 300

Gln Ser Phe Ser Val Arg Leu Gly Gln Lys Pro Val Phe Trp Thr Cys
305                 310                 315                 320

Val Ile Leu Leu Glu Ile Ala Tyr Gly Val Ala Leu Leu Val Gly Ala
```

-continued

```
                325                 330                 335
Ala Ser Pro Cys Leu Trp Ser Lys Ile Val Thr Gly Leu Gly His Ala
            340                 345                 350
Val Leu Ala Ser Ile Leu Trp Phe His Ala Lys Ser Val Asp Leu Lys
            355                 360                 365
Ser Lys Ala Ser Ile Thr Ser Phe Tyr Met Phe Ile Trp Lys Leu Phe
            370                 375                 380
Tyr Ala Glu Tyr Leu Leu Ile Pro Phe Val Arg
385                 390                 395

<210> SEQ ID NO 15
<211> LENGTH: 404
<212> TYPE: PRT
<213> ORGANISM: Oryza sativa

<400> SEQUENCE: 15

Met Asp Ser Leu Arg Leu Arg Pro Ser Leu Leu Ala Ala Arg Ala Pro
  1               5                  10                  15
Gly Ala Ala Ser Leu Pro Pro Leu Arg Arg Asp His Phe Leu Pro Pro
             20                  25                  30
Leu Cys Ser Ile His Arg Asn Gly Lys Arg Pro Val Ser Leu Ser Ser
         35                  40                  45
Gln Arg Thr Gln Gly Pro Ser Phe Asp Gln Cys Gln Lys Phe Phe Gly
     50                  55                  60
Trp Lys Ser Ser His His Arg Ile Pro His Arg Pro Thr Ser Ser Ser
65                  70                  75                  80
Ala Asp Ala Ser Gly Gln Pro Leu Gln Ser Ser Ala Glu Ala His Asp
                 85                  90                  95
Ser Ser Ser Ile Trp Lys Pro Ile Ser Ser Pro Asp Ala Phe Tyr
            100                 105                 110
Arg Phe Ser Arg Pro His Thr Val Ile Gly Thr Ala Leu Ser Ile Val
            115                 120                 125
Ser Val Ser Leu Leu Ala Val Glu Asn Leu Ser Asp Val Ser Pro Leu
        130                 135                 140
Phe Leu Thr Gly Leu Leu Glu Ala Val Val Ala Ala Leu Phe Met Asn
145                 150                 155                 160
Ile Tyr Ile Val Gly Leu Asn Gln Leu Phe Asp Ile Glu Ile Asp Lys
                165                 170                 175
Val Asn Lys Pro Thr Leu Pro Leu Ala Ser Gly Glu Tyr Ser Pro Ala
            180                 185                 190
Thr Gly Val Ala Leu Val Ser Ala Phe Ala Ala Met Ser Phe Gly Leu
        195                 200                 205
Gly Trp Ala Val Gly Ser Gln Pro Leu Phe Leu Ala Leu Phe Ile Ser
    210                 215                 220
Phe Ile Leu Gly Thr Ala Tyr Ser Ile Asn Leu Pro Phe Leu Arg Trp
225                 230                 235                 240
Lys Arg Ser Ala Val Val Ala Ala Leu Cys Ile Leu Ala Val Arg Ala
                245                 250                 255
Val Ile Val Gln Leu Ala Phe Phe Leu His Ile Gln Thr Phe Val Phe
            260                 265                 270
Arg Arg Pro Ala Val Phe Thr Arg Pro Leu Ile Phe Ala Thr Ala Phe
        275                 280                 285
Met Thr Phe Phe Ser Val Val Ile Ala Leu Phe Lys Asp Ile Pro Asp
    290                 295                 300
```

```
Ile Glu Gly Asp Arg Ile Phe Gly Ile Lys Ser Phe Ser Val Arg Leu
305                 310                 315                 320

Gly Gln Lys Lys Val Phe Trp Ile Cys Val Gly Leu Leu Glu Met Ala
            325                 330                 335

Tyr Cys Val Ala Ile Leu Met Gly Ala Thr Ser Ala Cys Leu Trp Ser
        340                 345                 350

Lys Tyr Ala Thr Val Val Gly His Ala Ile Leu Ala Ala Ile Leu Trp
    355                 360                 365

Asn Arg Ser Arg Ser Ile Asp Leu Thr Ser Lys Thr Ala Ile Thr Ser
370                 375                 380

Phe Tyr Met Phe Ile Trp Lys Leu Phe Tyr Ala Glu Tyr Leu Leu Ile
385                 390                 395                 400

Pro Leu Val Arg

<210> SEQ ID NO 16
<211> LENGTH: 399
<212> TYPE: PRT
<213> ORGANISM: Zea mays

<400> SEQUENCE: 16

Met Asp Ala Leu Arg Leu Arg Pro Ser Leu Pro Val Arg Pro Gly
  1               5                  10                  15

Ala Ala Arg Pro Arg Asp His Phe Leu Pro Pro Cys Cys Ser Ile Gln
            20                  25                  30

Arg Asn Gly Glu Gly Arg Ile Cys Phe Ser Ser Gln Arg Thr Gln Gly
        35                  40                  45

Pro Thr Leu His His His Gln Lys Phe Phe Glu Trp Lys Ser Ser Tyr
    50                  55                  60

Cys Arg Ile Ser His Arg Ser Leu Asn Thr Ser Val Asn Ala Ser Gly
 65                  70                  75                  80

Gln Gln Leu Gln Ser Glu Pro Glu Thr His Asp Ser Thr Thr Ile Trp
            85                  90                  95

Arg Ala Ile Ser Ser Ser Leu Asp Ala Phe Tyr Arg Phe Ser Arg Pro
        100                 105                 110

His Thr Val Ile Gly Thr Ala Leu Ser Ile Val Ser Val Ser Leu Leu
    115                 120                 125

Ala Val Gln Ser Leu Ser Asp Ile Ser Pro Leu Phe Leu Thr Gly Leu
130                 135                 140

Leu Glu Ala Val Val Ala Ala Leu Phe Met Asn Ile Tyr Ile Val Gly
145                 150                 155                 160

Leu Asn Gln Leu Phe Asp Ile Glu Ile Asp Lys Val Asn Lys Pro Thr
            165                 170                 175

Leu Pro Leu Ala Ser Gly Glu Tyr Thr Leu Ala Thr Gly Val Ala Ile
        180                 185                 190

Val Ser Val Phe Ala Ala Met Ser Phe Gly Leu Gly Trp Ala Val Gly
    195                 200                 205

Ser Gln Pro Leu Phe Trp Ala Leu Phe Ile Ser Phe Val Leu Gly Thr
210                 215                 220

Ala Tyr Ser Ile Asn Leu Pro Tyr Leu Arg Trp Lys Arg Phe Ala Val
225                 230                 235                 240

Val Ala Ala Leu Cys Ile Leu Ala Val Arg Ala Val Ile Val Gln Leu
            245                 250                 255

Ala Phe Phe Leu His Ile Gln Thr Phe Val Phe Arg Arg Pro Ala Val
        260                 265                 270
```

```
Phe Ser Arg Pro Leu Leu Phe Ala Thr Gly Phe Met Thr Phe Phe Ser
            275                 280                 285

Val Val Ile Ala Leu Phe Lys Asp Ile Pro Asp Ile Glu Gly Asp Arg
        290                 295                 300

Ile Phe Gly Ile Arg Ser Phe Ser Val Arg Leu Gly Gln Lys Lys Val
305                 310                 315                 320

Phe Trp Ile Cys Val Gly Leu Leu Glu Met Ala Tyr Ser Val Ala Ile
                325                 330                 335

Leu Met Gly Ala Thr Ser Ser Cys Leu Trp Ser Lys Thr Ala Thr Ile
                340                 345                 350

Ala Gly His Ser Ile Leu Ala Ala Ile Leu Trp Ser Cys Ala Arg Ser
                355                 360                 365

Val Asp Leu Thr Ser Lys Ala Ala Ile Thr Ser Phe Tyr Met Phe Ile
            370                 375                 380

Trp Lys Leu Phe Tyr Ala Glu Tyr Leu Leu Ile Pro Leu Val Arg
385                 390                 395

<210> SEQ ID NO 17
<211> LENGTH: 308
<212> TYPE: PRT
<213> ORGANISM: Synechocystis PCC6803

<400> SEQUENCE: 17

Met Ala Thr Ile Gln Ala Phe Trp Arg Phe Ser Arg Pro His Thr Ile
1               5                   10                  15

Ile Gly Thr Thr Leu Ser Val Trp Ala Val Tyr Leu Leu Thr Ile Leu
            20                  25                  30

Gly Asp Gly Asn Ser Val Asn Ser Pro Ala Ser Leu Asp Leu Val Phe
        35                  40                  45

Gly Ala Trp Leu Ala Cys Leu Leu Gly Asn Val Tyr Ile Val Gly Leu
    50                  55                  60

Asn Gln Leu Trp Asp Val Asp Ile Asp Arg Ile Asn Lys Pro Asn Leu
65                  70                  75                  80

Pro Leu Ala Asn Gly Asp Phe Ser Ile Ala Gln Gly Arg Trp Ile Val
                85                  90                  95

Gly Leu Cys Gly Val Ala Ser Leu Ala Ile Ala Trp Gly Leu Gly Leu
            100                 105                 110

Trp Leu Gly Leu Thr Val Gly Ile Ser Leu Ile Ile Gly Thr Ala Tyr
        115                 120                 125

Ser Val Pro Pro Val Arg Leu Lys Arg Phe Ser Leu Leu Ala Ala Leu
    130                 135                 140

Cys Ile Leu Thr Val Arg Gly Ile Val Val Asn Leu Gly Leu Phe Leu
145                 150                 155                 160

Phe Phe Arg Ile Gly Leu Gly Tyr Pro Pro Thr Leu Ile Thr Pro Ile
                165                 170                 175

Trp Val Leu Thr Leu Phe Ile Leu Val Phe Thr Val Ala Ile Ala Ile
            180                 185                 190

Phe Lys Asp Val Pro Asp Met Glu Gly Asp Arg Gln Phe Lys Ile Gln
        195                 200                 205

Thr Leu Thr Leu Gln Ile Gly Lys Gln Asn Val Phe Arg Gly Thr Leu
    210                 215                 220

Ile Leu Leu Thr Gly Cys Tyr Leu Ala Met Ala Ile Trp Gly Leu Trp
225                 230                 235                 240

Ala Ala Met Pro Leu Asn Thr Ala Phe Leu Ile Val Ser His Leu Cys
                245                 250                 255
```

```
Leu Leu Ala Leu Leu Trp Trp Arg Ser Arg Asp Val His Leu Glu Ser
            260                 265                 270

Lys Thr Glu Ile Ala Ser Phe Tyr Gln Phe Ile Trp Lys Leu Phe Phe
        275                 280                 285

Leu Glu Tyr Leu Leu Tyr Pro Leu Ala Leu Trp Leu Pro Asn Phe Ser
    290                 295                 300

Asn Thr Ile Phe
305

<210> SEQ ID NO 18
<211> LENGTH: 290
<212> TYPE: PRT
<213> ORGANISM: Escherichia coli K12

<400> SEQUENCE: 18

Met Glu Trp Ser Leu Thr Gln Asn Lys Leu Leu Ala Phe His Arg Leu
 1               5                  10                  15

Met Arg Thr Asp Lys Pro Ile Gly Ala Leu Leu Leu Leu Trp Pro Thr
            20                  25                  30

Leu Trp Ala Leu Trp Val Ala Thr Pro Gly Val Pro Gln Leu Trp Ile
        35                  40                  45

Leu Ala Val Phe Val Ala Gly Val Trp Leu Met Arg Ala Ala Gly Cys
    50                  55                  60

Val Val Asn Asp Tyr Ala Asp Arg Lys Phe Asp Gly His Val Lys Arg
65                  70                  75                  80

Thr Ala Asn Arg Pro Leu Pro Ser Gly Ala Val Thr Glu Lys Glu Ala
                85                  90                  95

Arg Ala Leu Phe Val Val Leu Val Leu Ile Ser Phe Leu Leu Val Leu
            100                 105                 110

Thr Leu Asn Thr Met Thr Ile Leu Leu Ser Ile Ala Ala Leu Ala Leu
        115                 120                 125

Ala Trp Val Tyr Pro Phe Met Lys Arg Tyr Thr His Leu Pro Gln Val
    130                 135                 140

Val Leu Gly Ala Ala Phe Gly Trp Ser Ile Pro Met Ala Phe Ala Ala
145                 150                 155                 160

Val Ser Glu Ser Val Pro Leu Ser Cys Trp Leu Met Phe Leu Ala Asn
                165                 170                 175

Ile Leu Trp Ala Val Ala Tyr Asp Thr Gln Tyr Ala Met Val Asp Arg
            180                 185                 190

Asp Asp Asp Val Lys Ile Gly Ile Lys Ser Thr Ala Ile Leu Phe Gly
        195                 200                 205

Gln Tyr Asp Lys Leu Ile Ile Gly Ile Leu Gln Ile Gly Val Leu Ala
    210                 215                 220

Leu Met Ala Ile Ile Gly Glu Leu Asn Gly Leu Gly Trp Gly Tyr Tyr
225                 230                 235                 240

Trp Ser Ile Leu Val Ala Gly Ala Leu Phe Val Tyr Gln Gln Lys Leu
                245                 250                 255

Ile Ala Asn Arg Glu Arg Glu Ala Cys Phe Lys Ala Phe Met Asn Asn
            260                 265                 270

Asn Tyr Val Gly Leu Val Leu Phe Leu Gly Leu Ala Met Ser Tyr Trp
        275                 280                 285

His Phe
290
```

```
<210> SEQ ID NO 19
<211> LENGTH: 378
<212> TYPE: PRT
<213> ORGANISM: Avena sativa

<400> SEQUENCE: 19

Met Ala Thr Ser His Pro Leu Ala Ala Ala Thr Ser Ser Ser
  1               5                  10                  15

Ser Ala Thr Phe Arg Pro Pro Leu Arg Phe Leu Ser Ser Pro Pro Ser
                 20                  25                  30

Ser Leu Thr Leu Asn Arg Arg Arg Ser Phe Pro Val Val Cys Ala Ala
             35                  40                  45

Asp Ala Asp Ala Lys Glu Thr Thr Lys Lys Pro Thr Ile Pro Asp Lys
 50                  55                  60

Ala Pro Ala Ala Gly Ser Ser Phe Asn Gln Leu Gly Ile Lys Gly
 65                      70                  75                  80

Ala Lys Gln Glu Thr Asn Ile Trp Lys Ile Arg Leu Gln Leu Thr Lys
                     85                  90                  95

Pro Val Thr Trp Pro Pro Leu Val Trp Gly Val Leu Cys Gly Ala Ala
                100                 105                 110

Ala Ser Gly Asn Phe His Trp Thr Val Glu Asp Val Thr Lys Ser Ile
            115                 120                 125

Val Cys Met Leu Met Ser Gly Pro Cys Leu Thr Gly Tyr Thr Gln Thr
130                 135                 140

Ile Asn Asp Trp Tyr Asp Arg Asp Ile Asp Ala Ile Asn Glu Pro Tyr
145                 150                 155                 160

Arg Pro Ile Pro Ser Gly Ala Ile Ser Glu Asn Glu Val Ile Thr Gln
                165                 170                 175

Ile Trp Val Leu Leu Leu Gly Gly Leu Gly Leu Gly Ala Leu Leu Asp
                180                 185                 190

Ile Trp Ala Gly His Asp Phe Pro Ile Ile Phe Tyr Leu Ala Leu Gly
            195                 200                 205

Gly Ser Leu Leu Ser Tyr Ile Tyr Ser Ala Pro Pro Leu Lys Leu Lys
210                 215                 220

Gln Asn Gly Trp Ile Gly Asn Phe Ala Leu Gly Ala Ser Tyr Ile Gly
225                 230                 235                 240

Leu Pro Trp Trp Ala Gly Gln Ala Leu Phe Gly Thr Leu Thr Pro Asp
                245                 250                 255

Ile Val Val Leu Thr Cys Leu Tyr Ser Ile Ala Gly Leu Gly Ile Ala
                260                 265                 270

Ile Val Asn Asp Phe Lys Ser Ile Glu Gly Asp Arg Thr Leu Gly Leu
            275                 280                 285

Gln Ser Leu Pro Val Ala Phe Gly Met Glu Thr Ala Lys Trp Ile Cys
290                 295                 300

Val Gly Ala Ile Asp Ile Thr Gln Leu Ser Val Ala Ala Tyr Leu Leu
305                 310                 315                 320

Ser Thr Gly Lys Leu Tyr Tyr Ala Leu Ala Leu Gly Leu Thr Ile
                325                 330                 335

Pro Gln Val Ile Leu Gln Phe Gln Tyr Phe Leu Lys Asp Pro Val Lys
                340                 345                 350

Tyr Asp Val Lys Tyr Gln Ala Ser Ala Gln Pro Phe Phe Val Phe Gly
            355                 360                 365

Leu Leu Val Thr Ala Leu Ala Thr Ser His
        370                 375
```

```
<210> SEQ ID NO 20
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 6, 9, 12, 15
<223> OTHER INFORMATION: n = A,T,C or G

<400> SEQUENCE: 20
tayrtngtng gnhtnaayca                                              20

<210> SEQ ID NO 21
<211> LENGTH: 7
<212> TYPE: PRT
<213> ORGANISM: Artificial Sequence
<220> FEATURE:
<223> OTHER INFORMATION: primer
<220> FEATURE:
<221> NAME/KEY: VARIANT
<222> LOCATION: 2, 5
<223> OTHER INFORMATION: Xaa = Any Amino Acid

<400> SEQUENCE: 21

Tyr Xaa Val Gly Xaa Asn Gln
 1               5

<210> SEQ ID NO 22
<211> LENGTH: 23
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 9, 12
<223> OTHER INFORMATION: n = A,T,C or G

<400> SEQUENCE: 22
gcrtaraana rnttccadat raa                                          23

<210> SEQ ID NO 23
<211> LENGTH: 8
<212> TYPE: PRT
<213> ORGANISM: Artificial Sequence
<220> FEATURE:
<223> OTHER INFORMATION: translation of SEQ ID NO:22
<220> FEATURE:
<221> NAME/KEY: VARIANT
<222> LOCATION: 4, 5
<223> OTHER INFORMATION: Xaa = Any Amino Acid

<400> SEQUENCE: 23

Phe Ile Trp Xaa Xaa Phe Tyr Ala
 1               5

<210> SEQ ID NO 24
<211> LENGTH: 21
<212> TYPE: DNA
<213> ORGANISM: Artificial Sequence
<220> FEATURE:
<223> OTHER INFORMATION: PCR primer

<400> SEQUENCE: 24
aaattaaccc tcactaaagg g                                            21
```

<210> SEQ ID NO 25
<211> LENGTH: 21
<212> TYPE: DNA
<213> ORGANISM: Artificial Sequence
<220> FEATURE:
<223> OTHER INFORMATION: PCR primer

<400> SEQUENCE: 25
atacatgatg cagcgaggag c                                              21

<210> SEQ ID NO 26
<211> LENGTH: 20
<212> TYPE: DNA
<213> ORGANISM: Artificial Sequence
<220> FEATURE:
<223> OTHER INFORMATION: PCR primer

<400> SEQUENCE: 26
ctctagaact agtggatccc                                                20

<210> SEQ ID NO 27
<211> LENGTH: 20
<212> TYPE: DNA
<213> ORGANISM: Artificial Sequence
<220> FEATURE:
<223> OTHER INFORMATION: PCR primer

<400> SEQUENCE: 27
gtattcctat gctaaagctc                                                20

<210> SEQ ID NO 28
<211> LENGTH: 20
<212> TYPE: DNA
<213> ORGANISM: Artificial Sequence
<220> FEATURE:
<223> OTHER INFORMATION: PCR primer

<400> SEQUENCE: 28
gaattttcag tagcaactgg                                                20

<210> SEQ ID NO 29
<211> LENGTH: 17
<212> TYPE: DNA
<213> ORGANISM: Artificial Sequence
<220> FEATURE:
<223> OTHER INFORMATION: PCR primer

<400> SEQUENCE: 29
gtaaaacgac ggccagt                                                   17

<210> SEQ ID NO 30
<211> LENGTH: 21
<212> TYPE: DNA
<213> ORGANISM: Artificial Sequence
<220> FEATURE:
<223> OTHER INFORMATION: PCR primer

<400> SEQUENCE: 30
ctcctcgctg catcatgtat c                                              21

<210> SEQ ID NO 31
<211> LENGTH: 22
<212> TYPE: DNA
<213> ORGANISM: Artificial Sequence
<220> FEATURE:
<223> OTHER INFORMATION: PCR primer

<400> SEQUENCE: 31
gtaatacgac tcactatagg gc                                                22

<210> SEQ ID NO 32
<211> LENGTH: 29
<212> TYPE: DNA
<213> ORGANISM: Artificial Sequence
<220> FEATURE:
<223> OTHER INFORMATION: PCR primer

<400> SEQUENCE: 32
ttccatggcg aggatgcaag ccgtcacgg                                         29

<210> SEQ ID NO 33
<211> LENGTH: 30
<212> TYPE: DNA
<213> ORGANISM: Artificial Sequence
<220> FEATURE:
<223> OTHER INFORMATION: PCR primer

<400> SEQUENCE: 33
ttgaattcac acatctgctg gcccttgtac                                        30

<210> SEQ ID NO 34
<211> LENGTH: 655
<212> TYPE: DNA
<213> ORGANISM: Triticum aestivum

<400> SEQUENCE: 34
gcacgaggca acattgttca tgtgttgctt ctctgccgtc atagctctat tcaaggatat        60
tcctgatgtt gatggagacc gagattttgg catccaatcc ttgagtgtga gattggggcc      120
acaaagagtg tatcagctct gcataagcat actgttaaca gcctatgggg ctgccactgt      180
agtaggagct tcatccacac acctacttca aaagatcatc actgtgtctg gccatggcct      240
gcttgctgtg acactttggc agagagcgcg gcaccttgag gttgaaaacc aagcgcgtgt      300
cacatcattt tacatgttca tttggaaggt aactaattaa gttgctcgca tatattgtgc      360
attctctaag ccattaaact ttggctatat atgcctaatg attatttgca cttattgtgt      420
cactttcatg cagctattct atgcagagta tttccttata ccgtttgtgc agtaaaattt      480
gtacaagggc cagcagatgt gaactatata tacatgtaaa acaaattata ttactgatga      540
taccctatcc aatgcttgga ttttccttgt actgtgttat ctgtaattcc atgatctaga      600
gaaagaggca aatgttgggt gtgtaaaaaa aaaaaaaaaa aaaaaaaaaa aaaaa           655

<210> SEQ ID NO 35
<211> LENGTH: 23
<212> TYPE: DNA
<213> ORGANISM: Artificial Sequence
<220> FEATURE:
<223> OTHER INFORMATION: PCR primer

<400> SEQUENCE: 35
gccaagctcg gaattaaccc tca                                               23

<210> SEQ ID NO 36
<211> LENGTH: 24
<212> TYPE: DNA
<213> ORGANISM: Artificial Sequence
<220> FEATURE:
<223> OTHER INFORMATION: PCR primer

<400> SEQUENCE: 36

```
cacagtacaa ggaaaatcca agca                                          24

<210> SEQ ID NO 37
<211> LENGTH: 25
<212> TYPE: DNA
<213> ORGANISM: Artificial Sequence
<220> FEATURE:
<223> OTHER INFORMATION: PCR primer

<400> SEQUENCE: 37
gccgctctag aactagtgga tcccc                                         25

<210> SEQ ID NO 38
<211> LENGTH: 23
<212> TYPE: DNA
<213> ORGANISM: Artificial Sequence
<220> FEATURE:
<223> OTHER INFORMATION: PCR primer

<400> SEQUENCE: 38
tccaagcatt ggatagggta tca                                           23

<210> SEQ ID NO 39
<211> LENGTH: 30
<212> TYPE: DNA
<213> ORGANISM: Artificial Sequence
<220> FEATURE:
<223> OTHER INFORMATION: PCR primer

<400> SEQUENCE: 39
ttggaattcg tggccgcccg gcgaggatgc                                    30

<210> SEQ ID NO 40
<211> LENGTH: 30
<212> TYPE: DNA
<213> ORGANISM: Artificial Sequence
<220> FEATURE:
<223> OTHER INFORMATION: PCR primer

<400> SEQUENCE: 40
ttggtacctc acatctgctg gcccttgtac                                    30

<210> SEQ ID NO 41
<211> LENGTH: 20
<212> TYPE: DNA
<213> ORGANISM: Artificial Sequence
<220> FEATURE:
<221> NAME/KEY: misc_feature
<222> LOCATION: 12
<223> OTHER INFORMATION: n = A,T,C or G
<220> FEATURE:
<223> OTHER INFORMATION: PCR primer

<400> SEQUENCE: 41
athgayaarr tnaayaarcc                                               20

<210> SEQ ID NO 42
<211> LENGTH: 7
<212> TYPE: PRT
<213> ORGANISM: Artificial Sequence
<220> FEATURE:
<223> OTHER INFORMATION: Translation of SEQ ID NO:41
<220> FEATURE:
<221> NAME/KEY: VARIANT
<222> LOCATION: 4
<223> OTHER INFORMATION: Xaa = Any Amino Acid
```

```
<400> SEQUENCE: 42

Ile Asp Lys Xaa Asn Lys Pro
 1               5

<210> SEQ ID NO 43
<211> LENGTH: 22
<212> TYPE: DNA
<213> ORGANISM: Artificial Sequence
<220> FEATURE:
<223> OTHER INFORMATION: PCR primer

<400> SEQUENCE: 43
ggaagtgcat actctgttga tg                                          22

<210> SEQ ID NO 44
<211> LENGTH: 22
<212> TYPE: DNA
<213> ORGANISM: Artificial Sequence
<220> FEATURE:
<223> OTHER INFORMATION: PCR primer

<400> SEQUENCE: 44
cttgtatact atttgtaaga gc                                          22

<210> SEQ ID NO 45
<211> LENGTH: 16
<212> TYPE: DNA
<213> ORGANISM: Artificial Sequence
<220> FEATURE:
<223> OTHER INFORMATION: PCR primer

<400> SEQUENCE: 45
aacagctatg accatg                                                 16

<210> SEQ ID NO 46
<211> LENGTH: 22
<212> TYPE: DNA
<213> ORGANISM: Artificial Sequence
<220> FEATURE:
<223> OTHER INFORMATION: PCR primer

<400> SEQUENCE: 46
ataattgctc atgtgcatgg tc                                          22

<210> SEQ ID NO 47
<211> LENGTH: 21
<212> TYPE: DNA
<213> ORGANISM: Artificial Sequence
<220> FEATURE:
<223> OTHER INFORMATION: PCR primer

<400> SEQUENCE: 47
catgtaaatg atgtgatcca c                                           21

<210> SEQ ID NO 48
<211> LENGTH: 31
<212> TYPE: DNA
<213> ORGANISM: Artificial Sequence
<220> FEATURE:
<223> OTHER INFORMATION: PCR primer

<400> SEQUENCE: 48
ttgcggccgc agacgatgca agcctcatcg g                                31

<210> SEQ ID NO 49
```

```
<211> LENGTH: 32
<212> TYPE: DNA
<213> ORGANISM: Artificial Sequence
<220> FEATURE:
<223> OTHER INFORMATION: PCR primer

<400> SEQUENCE: 49
ttgcggccgc cttgcccttg tgtatatagt gc                                        32

<210> SEQ ID NO 50
<211> LENGTH: 28
<212> TYPE: DNA
<213> ORGANISM: Artificial Sequence
<220> FEATURE:
<223> OTHER INFORMATION: PCR primer

<400> SEQUENCE: 50
ttcccgggag acgatgcaag cctcatcg                                             28

<210> SEQ ID NO 51
<211> LENGTH: 30
<212> TYPE: DNA
<213> ORGANISM: Artificial Sequence
<220> FEATURE:
<223> OTHER INFORMATION: PCR primer

<400> SEQUENCE: 51
ttggtaccgt gtatatagtg ctcactgcac                                           30

<210> SEQ ID NO 52
<211> LENGTH: 38
<212> TYPE: DNA
<213> ORGANISM: Artificial Sequence
<220> FEATURE:
<223> OTHER INFORMATION: PCR primer

<400> SEQUENCE: 52
ttgcggccgc aggatgcaag ccgtcacggc ggcagccg                                  38

<210> SEQ ID NO 53
<211> LENGTH: 33
<212> TYPE: DNA
<213> ORGANISM: Artificial Sequence
<220> FEATURE:
<223> OTHER INFORMATION: PCR primer

<400> SEQUENCE: 53
ttgcggccgc ttcacatctg ctggcccttg tac                                       33

<210> SEQ ID NO 54
<211> LENGTH: 32
<212> TYPE: DNA
<213> ORGANISM: Artificial Sequence
<220> FEATURE:
<223> OTHER INFORMATION: PCR primer

<400> SEQUENCE: 54
atttaattaa gccggcgagg atgcaagccg tc                                        32

<210> SEQ ID NO 55
<211> LENGTH: 33
<212> TYPE: DNA
<213> ORGANISM: Artificial Sequence
<220> FEATURE:
<223> OTHER INFORMATION: PCR primer

<400> SEQUENCE: 55
```

-continued

```
tattaattaa ttcacatctg ctggcccttg tac                                    33

<210> SEQ ID NO 56
<211> LENGTH: 18
<212> TYPE: PRT
<213> ORGANISM: Artificial Sequence
<220> FEATURE:
<223> OTHER INFORMATION: conserved motif

<400> SEQUENCE: 56

Phe Cys Arg Pro His Thr Ile Phe Gly Thr Ile Ile Gly Ile Thr Ser
 1               5                  10                  15

Val Ser

<210> SEQ ID NO 57
<211> LENGTH: 11
<212> TYPE: PRT
<213> ORGANISM: Artificial Sequence
<220> FEATURE:
<223> OTHER INFORMATION: conserved motif

<400> SEQUENCE: 57

Leu Cys Met Asn Ile Tyr Val Val Gly Leu Asn
 1               5                  10

<210> SEQ ID NO 58
<211> LENGTH: 5
<212> TYPE: PRT
<213> ORGANISM: Artificial Sequence
<220> FEATURE:
<223> OTHER INFORMATION: conserved motif

<400> SEQUENCE: 58

Leu Gly Ser Ala Tyr
 1               5

<210> SEQ ID NO 59
<211> LENGTH: 5
<212> TYPE: PRT
<213> ORGANISM: Artificial Sequence
<220> FEATURE:
<223> OTHER INFORMATION: conserved motif

<400> SEQUENCE: 59

Leu Arg Trp Lys Arg
 1               5

<210> SEQ ID NO 60
<211> LENGTH: 10
<212> TYPE: PRT
<213> ORGANISM: Artificial Sequence
<220> FEATURE:
<223> OTHER INFORMATION: conserved motif

<400> SEQUENCE: 60

Leu Ala Ala Ser Cys Ile Leu Phe Val Arg
 1               5                  10

<210> SEQ ID NO 61
<211> LENGTH: 17
<212> TYPE: PRT
<213> ORGANISM: Artificial Sequence
<220> FEATURE:
<223> OTHER INFORMATION: conserved motif

<400> SEQUENCE: 61
```

Leu Ala Phe Phe Ala His Met Gln Gln His Val Leu Lys Arg Pro Leu
1               5                   10                  15
Ala

<210> SEQ ID NO 62
<211> LENGTH: 10
<212> TYPE: PRT
<213> ORGANISM: Artificial Sequence
<220> FEATURE:
<223> OTHER INFORMATION: conserved motif

<400> SEQUENCE: 62

Val Phe Ala Thr Leu Phe Met Cys Cys Phe
1               5                   10

<210> SEQ ID NO 63
<211> LENGTH: 10
<212> TYPE: PRT
<213> ORGANISM: Artificial Sequence
<220> FEATURE:
<223> OTHER INFORMATION: conserved motif

<400> SEQUENCE: 63

Val Ile Ala Leu Phe Lys Asp Ile Pro Asp
1               5                   10

<210> SEQ ID NO 64
<211> LENGTH: 6
<212> TYPE: PRT
<213> ORGANISM: Artificial Sequence
<220> FEATURE:
<223> OTHER INFORMATION: conserved motif

<400> SEQUENCE: 64

Gly His Gly Leu Leu Ala
1               5

<210> SEQ ID NO 65
<211> LENGTH: 5
<212> TYPE: PRT
<213> ORGANISM: Artificial Sequence
<220> FEATURE:
<223> OTHER INFORMATION: conserved motif

<400> SEQUENCE: 65

Leu Trp Gln Arg Ala
1               5

<210> SEQ ID NO 66
<211> LENGTH: 18
<212> TYPE: PRT
<213> ORGANISM: Artificial Sequence
<220> FEATURE:
<223> OTHER INFORMATION: conserved motif

<400> SEQUENCE: 66

Phe Tyr Met Phe Ile Trp Lys Leu Phe Tyr Ala Glu Tyr Phe Leu Ile
1               5                   10                  15
Pro Phe

<210> SEQ ID NO 67
<211> LENGTH: 23
<212> TYPE: DNA
<213> ORGANISM: Artificial Sequence
<220> FEATURE:

```
<223> OTHER INFORMATION: PCR primer

<400> SEQUENCE: 67
cgtaaaatcg tccaggctct ttc                                         23

<210> SEQ ID NO 68
<211> LENGTH: 23
<212> TYPE: DNA
<213> ORGANISM: Artificial Sequence
<220> FEATURE:
<223> OTHER INFORMATION: PCR primer

<400> SEQUENCE: 68
gcctcgagaa atccccatat agc                                         23
```